United States Patent
Neri et al.

(12) 
(10) Patent No.: US 6,194,149 B1
(45) Date of Patent: Feb. 27, 2001

(54) TARGET-DEPENDENT REACTIONS USING STRUCTURE-BRIDGING OLIGONUCLEOTIDES

(75) Inventors: Bruce Neri; Fang Dong; Victor Lyamichev; Mary Ann D. Brow, all of Madison, WI (US); Lance Fors, Monrovia, CA (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

(21) Appl. No.: 09/034,205

(22) Filed: Mar. 3, 1998

(51) Int. Cl.[7] .............................. C12Q 1/68; C07H 21/02; C07H 21/04
(52) U.S. Cl. ........................ 435/6; 536/23.1; 536/24.3
(58) Field of Search .................. 435/6; 536/23.1, 536/24.3; 935/76, 77, 78

(56) References Cited

U.S. PATENT DOCUMENTS

| | | | |
|---|---|---|---|
| 4,775,619 | * 10/1988 | Urdea ........................ | 435/6 |
| 5,202,231 | 4/1993 | Drmanac et al. ............. | 435/6 |
| 5,422,253 | 6/1995 | Dahlberg et al. ............. | 435/91.53 |
| 5,427,930 | 6/1995 | Birkenmeyer et al. ........ | 435/91.52 |
| 5,429,807 | 7/1995 | Matson et al. ............... | 422/131 |
| 5,436,327 | 7/1995 | Southern et al. ............. | 536/25.34 |
| 5,472,840 | * 12/1995 | Stefano ....................... | 435/6 |
| 5,492,806 | 2/1996 | Drmanac et al. ............. | 435/5 |
| 5,494,810 | 2/1996 | Barany et al. ............... | 435/91.52 |
| 5,510,270 | 4/1996 | Fodor et al. ................. | 436/518 |
| 5,589,332 | * 12/1996 | Shih et al. ................... | 435/6 |
| 5,599,695 | 2/1997 | Pease et al. ................. | 435/91.1 |
| 5,656,744 | 8/1997 | Arnold, Jr. et al. ........... | 536/25.3 |
| 5,759,773 | * 6/1998 | Tyagi et al. ................. | 435/6 |
| 5,871,911 | * 2/1999 | Dahlberg et al. ............. | 435/6 |

FOREIGN PATENT DOCUMENTS

| | | |
|---|---|---|
| 5-015399 | * 1/1993 | (JP) . |
| WO 95/15267 | 6/1995 | (WO) . |
| WO 96/04374 | 2/1996 | (WO) . |
| WO 97/27214 | 7/1997 | (WO) . |
| WO 98/23774 | 4/1998 | (WO) . |

OTHER PUBLICATIONS

Brow et al., J. of Clinical Microbiology 34(12) : 3129–3137 (1996).*
Dimmock et al., Intoduction to Modern Virology (4th Edition, 1994) Blackwell Sciences, Inc., pp. 340–362, Cambridge, MA.*

(List continued on next page.)

*Primary Examiner*—Ethan Whisenant
(74) *Attorney, Agent, or Firm*—Medlen & Carroll, LLP

(57) ABSTRACT

The present invention relates to methods and compositions for analyzing nucleic acids. In particular, the present invention provides methods and compositions for the detection and characterization of nucleic acid sequences and sequence changes. The methods of the present invention permit the detection and/or identification of genetic polymorphism such as those associated with human disease and permit the identification of pathogens (e.g., viral and bacterial strain identification).

13 Claims, 50 Drawing Sheets

OTHER PUBLICATIONS

Matthews et al., Analytical Biochemistry 169 : 1–25 (1988).*

Abrams et al., "Comprehensive Detection of Single Base Changes in Human Genomic DNA Using Denaturing Gradient Gel Electrophoresis and a GC Clamp," *Genomics* 7:463–475 [1990].

Altamirano et al., "Identification of Hepatitis C Virus Genotypes among Hospitalized Patients in British Columbia, Canada," *J. Infect. Dis.* 171:1034–1038 [1995].

Bains and Smith, "A Novel Method for Nucleic Acid Sequence Determination," *J. Theor. Biol.* 135:303–307 [1988].

Banerjee et al., "inhA, a Gene Encoding a Target for Isoniazid and Ethionamide in *Mycobacterium tuberculosis*," *Science* 263:227–230 [1994].

Barany, "The Ligase Chain Reaction in a PCR World," *PCR Meth. App.* 1:5–16 [1991].

Barlow and Lehrach, "Genetics by gel electrophoresis: the impact of pulsed field gel electrophoresis on mammalian genetics," *Trends Genet.* 3:167–171 [1987].

Bidou et al.,"In vivo HIV–1 frameshifting efficiency is directly related to the stability of the stem–loop stimulatory signal," *RNA* 3:1153–1158 [1997].

Borrensen et al., "Constant denaturant gel electrophoresis as a rapid screening technique for p53 mutations," *Proc. Natl. Acad. Sci. USA* 88:8405–8409 [1991].

Brow et al., "Differentiation of Bacterial 16S rRNA Genes and Intergenic Regions and *Mycobacterium tuberculosis* katG Genes by Structure–Specific Endonuclease Cleavage," *J. Clin. Microbiol.* 34:3129–3137 [1996].

Chee et al., "Accessing Genetic Information with High–Density DNA Arrays," *Science* 274:610–614 [1996].

Cload and Schepartz, "Polyether Tethered Oligonucleotide Probes," *J. Am. Chem. Soc.* 113:6324–6326 [1991].

Cockerill, III et al., "Rapid Identification of a Point Mutation of the *Mycobacterium tuberculosis* Catalase–Peroxidase (katG) Gene Associated with Isoniazid Resistance," *J. Infect. Dis.* 171:240–245 [1995].

Compton in *PCR Protocols*, Innis et al. (Eds.), [1990], pp. 39–45.

Conner, "Detection of sickle cell $\beta^S$–globin allele by hybridization with synthetic oligonucleotides," *Proc. Natl. Acad. Sci.* 80:278–282 [1983].

Donnabella et al., "Isolation of the Gene for the β Subunit of RNA Polymerase from Rifampicin–resistant *Mycobacterium tuberculosis* and Indentification of New Mutations," *Am. J. Respir. Dis.* 11:639–643 [1994].

Doty et al., "Strand Separation and Specific Recombination in Deoxyribonucleic Acids: Physical Chemical Studies," *Proc. Natl. Acad. Sci. USA* 46:461 [1960].

Drmanac et al., "Sequencing of Megabase Plus DNA by Hybridization: Theory of the Method," *Genomics* 4:114–128 [1989].

Duckett et al., "The Structure of the Holliday Junction, and Its Resolution," *Cell* 55:79–89 [1988].

Eckstein and Lilley (eds.), *Nucleic Acids and Molecular Biology*, vol. 2, Springer–Verlag, Heidelberg [1988]. (This publication is not provided but is available upon request of the Examiner).

Fedorova et al., "The Influence of the Target Structure on the Efficiency of Alkylation of Single–Stranded DNA with the Reactive Derivatives of Antisense Oligonucleotides," *FEBS Lett.* 302:47–50 [1992].

Fodor et al., "Light–Directed, Spatially Addressable Parallel Chemical Synthesis," *Science* 251:767–773 [1991].

Fodor et al., "Multiplexed biochemical assays with biological chips," *Nature* 364:555–556 [1993].

Francois et al., "Recognition and Cleavage of Hairpin Structures in Nucleic Acids by Oligodeoxynucleotides," *Nucleic Acids Research* 22(19):343–3950 [1994].

Frieden et al., "The Emergence of Drug–Resistant Tuberculosis in New York City," *New Engl. J. Med.* 328:521–526 [1993].

Gamper et al., "Solution Hybridization of Crosslinkable DNA Oligonucleotides to Bacteriophage M13 DNA Oligonucleotides to Bacteriophage M13 DNA: Effect of Secondary Structure on Hybridization Kinetics and Equilibria," *J. Mol. Biol.* 197:349–362 [1987].

Gaspin and Westhof, "An Interactive Framework for RNA Secondary Structure Prediction with a Dynamical Treatment of Constrains," *J. Mol. Biol.* 254:163 [1995].

Gesteland and Atkins (eds.), *The RNA World*, Cold Spring Harbor Laboratory Press, Cold Spring Harbor, NY [1993]. (This publication is not provided but is available upon request of the Examiner).

Girelli et al., "Hereditary Hyperferritinemia–Cataract Syndrome Caused by a 29–Base Pair Deletion in the Iron Responsive Element of Ferritin L–subunit Gene," *Blood* 90:2084 [1997].

Godard et al., "Photochemically and Chemically Activatable Antisense Oligonucleotides: Comparison of Their Reactivities Towards DNA and RNA Targets," *Nuc. Acids Res.* 22:4789–4795 [1994].

Gogos et al., "Detection of single base mismatches of thymine and cytosine residues by potassium permanganate and hydroxylamine in the presence of tetralkylammonium salts," *Nucl. Acids Res.* 18:6807–6817 [1990].

Hanke et al., "Repetitive Alu Elements form a Cruciform Structure that Regulates the Function of the Human CD8α T Cell–specific Enhancer," *J. Mol. Biol.* 246:63 [1995].

Harrington and Lieber, "Functional domains within FEN–1 and RAD2 define a family of structure–specific endonucleases: implications for nucleotide excision repair," *Genes and Develop.* 3:1344–1355 [1994].

Hayashi, "PCR–SSCP: A Simple and Sensitive Method for Detection of Mutations in the Genomic DNA," *PCR Meth. Appl.* 1:34–38 [1991].

Heym et al., "Implications of multidrug resistance for the future of short0–course chemotherapy of tuberculosis: a molecular study," *Lancet* 344:293–298 [1994].

Hirao et al., "Most Compact Hairpin–Turn Structure Exerted by a Short DNA Fragment, d(GCGAAGC) in Solution: An Extraordinarily Stable Structure Resistant to Nucleases and Heat," *Nucleic Acids Res.* 22(4):576–582 [1994].

Howe and Ares, "Intron self–complementarity enforces exon inclusion in a yeast pre–mRNA," *Proc. Natl. Acad. Sci. USA* 94:1246712472 [1997].

Hughes, "The resurgence of tuberculosis," *Scrip Magazine*, pp. 46–48 [May 1994].

Jacobs, Jr. et al., "Rapid Assessment of Drug Susceptibilities of *Mycobacterium tuberculosis* by Means of Luciferase Reporter Phages," *Science* 260:819–822 [1993].

Jacobs, Jr., "Multiple–Drug–Resistant Tuberculosis," *Clin. Infect. Dis.* 19:1–8 [1994].

Jaeger et al., "Improved predictions of secondary structures for RNA," *Proc. Natl. Acad. Sci. USA* 86:7706–7710 [1989].

Jaeger et al., "Predicting Optimal and Suboptimal Secondary Structure for RNA," *Meth. Enzymol.* 183:281–306 [1990].

Kaczorowski and Szybalski, "Co–Operativity of hexamer ligation," *Gene* 179:189–193 [1996].

Kanai et al., "HCV genotypes in chronic hepatitis C and response to interferon," *Lancet* 339:1543 [1992].

Kwok et al., "Effects of Primer—Template Mismatches on the Polymerase Chain Reaction: Human Immunodeficiency Virus Type 1 Model Studies," *Nucl. Acids. Res.* 18:999–1005 [1990].

Lerman and Silverstein, "Computational Simulation of DNA Melting and Its Application to Denaturing Gradient Gel Electrophoresis," *Meth. Enzymol.* 155:482–501 [1987].

Lima et al., "Implication of RNA Structure on Antisense Oligonucleotide Hybridization Kinetics," *Biochem.* 31:12055–12061 [1992].

Liu and Sommer, "Parameters Affecting the Sensitivities of Dideoxy Fingerprinting and SSCP," *PCR Methods Appli.*, 4:97–108 [1994].

Lowman and Draper, "On the Recognition of Helical RNa by Cobra Venom $V_1$ Nuclease," *J. Biol. Chem.*, 261:5396–5403 [1986].

Lyamichev et al., "Structure–Specific Endonucleolytic Cleavage of Nucleic Acids by Eubacterial DNA Polymerase," *Science* 260: 778–7322 [1993].

Mangada and Igarishi, "Sequences of Terminal Non–Coding Regions from Four Dengue–2 Viruses Isolated from Patients Exhibiting Different Disease Severities," *Virus Genes* 14:5–12 [1997].

Marmur and Lane, "Strand Separation and Specific Recombination in Deoxyribonucleic Acids: Biological Studies," *Proc. Natl. Acad. Sci. USA* 46:453–461 [1960].

Maskos and Southern, "Parallel analysis of oligodeoxyribonucleotide (oligonucleotide) interactions. I. Analysis of factors influencing oligonucleotide duplex formation," *Nucleic Acids Res* 20(7):1675–1678 [1992].

Miller, et al., "Multiple Biological Roles Associates with the Rous Sarcoma Virus 5' Untranslated RNa U5–IR Stem and Looe," *J Virol.*, 71:7648–765 [1997].

Morris et al., "Molecular Mechanisms of Multiple Drug Resistance in Clinical Isolates of *Mycobacterium tuberculosis*," *J. Infect. Dis.* 171:954–960 [1995].

Murante, R.S., et al., "The Calf 5'– to 3'Exonuclease Is Also an Endonuclease with Both Activities Dependent on Primers Annealed Upstream of the Point of Cleavage," *J. Biol. Chem.* 269:1191–1196 [1994].

Myers et al., "Reverse Transcription and DNA Amplification by a *Thermus thermophilus* DNA Polymerase," *Biochem.* 30:7661–7666 [1991].

Myers et al., "Detection of Single Base Substitutions by Ribonuclease Cleavage at Mismatches in RNA:DNA Duplexes," *Science* 230:1242–1246 [1985].

Okamoto et al. "Typing hepatitis C virus by polymerase chain reaction with type–specific primers: application to clinical surveys and tracing infectious sources," *J. Gen. Virol.* 73:673–679 [1992].

Orita et al., "Rapid and Sensitive Detection of Point Mutations and DNA Polymorphisms Using the Polymerase Chain Reaction," *Genomics* 5:874–879 [1989].

Parkhurst and Parkhurst, "Kinetic Studies by Fluorescence Resonance Energy Transfer Employing a Double–Labeled Oligonucleotide: Hybridization to the Oligonucleotide Complement and to Single–Stranded DNA," *Biochem.* 34:285–292 [1995].

Patel et al., "Formation of Chimeric DNA Primer Extension Products by Template Switching Onto An Annealed Downstream Oligonucleotide," *Proc. Natl. Acad. Sci. USA* 93:2969–2974 [1996].

Perlman and Butow, "Mobile Introns and Intron–Encoded Proteins," *Science* 246:1106–1109 [1989].

Proutski et al., "Secondary structure of the 3'–untranslated region of yellow fever virus: implications for virulence, attenuation and vaccine development," *J Gen Virol.*, 78:1543–1549 [1997].

Richardson and Schepartz, "Tethered Oligonucleotide Probes. A Strategy for the Recognition of Structured RNA," *J. Am. Chem. Soc.* 113:5109–5111 [1991].

Sambrook et al, *Molecular Cloning: A Laboratory Manual*, 2nd ed. Cold Spring Harbor Laboratory Press, Cold Spring Harbor, NY [1989]. (This publication is not provided but is available upon request of the Examiner).

Scholz, et al., "Rapid screening for Tp53 mutations by temperature gradient gel electrophoresis: a comparison with SSCP analysis," *Hum. Mol. Genet.* 2:2155–2158 [1993].

Schwille et al., "Quantitative Hybridization Kinetics of DNA Probes to RNA in Solution Followed by Diffusional Fluorescence Correlation Analysis," *Biochem.* 35:10182–10193 [1996].

Serano and Cohen, "A Small Predicted Stem–Loop Structure Mediates Oocyte Localization of Drosophila K10 mRNA," *Development* 121:3809–3818 [1995].

Sheffield et al., "Attachment of a 40–base–pair G+C–rich sequence (GC–clamp) to genomic DNA fragments by the polymerase chain reaction results in improved detection of single–base changes," *Proc. Natl. Acad. Sci.* 86:232–236 [1989].

Shibata in *PCR: The Polymerase Chain Reaction*, "Preparation of Nucleic Acids for Archival Material," (eds., Mullis et al.) Boston, pp. 47–54 [1994].

Shinnick and Jones in *Tuberculosis: Pathogenesis, Protection and Control*, "Molecular Approaches to the Diagnosis of Tuberculosis," (ed., Bloom), American Society of Microbiology, Washington, D.C. [1994], pp. 517–530.

Smith et al., "Novel Method of Detecting Single Base Substitutions in RNA Molecules by Differential Melting Behavior in Solution," *Genomics* 3:217–223 [1988].

Southern et al., "Analyzing and Comparing Nucleic Acid Sequences by Hybridization to Arrays of Oligonucleotides: Evaluation Using Experimental Models," *Genomics* 13:1008–1017 [1992].

Thompson et al., "Microsatellite deletions in the c–myb transcriptional attenuator region associated with over–expression in colon tumour cell lines," *Oncogene* 14:1715 [1997].

Veyrune et al, "c–fos mRNA instability determinants present within both the coding and the 3' non coding region link the degradation of this mRNA to its translation," *Oncogene* 11:2127 [1995].

Wallace et al., "Hybridization of Synthetic Oligodeoxyribonucleotides to $\Phi_x 174$ DNA: The Effect of Single Base Pair Mismatch," *Nucl. Acids Res.* 6:3543–3557 [1979].

Ward, et al., "Changes in the NS Gene of Neurovirulent Strains of Influenza Affect Splicing," *Virus Genes* 10:91–94 [1995].

Wartell et al., "Detecting base pair substitutions in DNA fragments by temperature–gradient gel electrophoresis," *Nucl. Acids Res.* 18:2699–2701 [1990].

Winter et al., "A method to detect and characterize point mutations in transcribed genes: Amplification and overexpression of the mutant c–Ki–ras allele in human tumor cells," *Proc. Natl. Acad. Sci. USA* 82:7575–7579 [1985].

Woese, "Bacterial Evolution," *Microbiological Reviews* 51(2):221–271 [1987].

Yang and Millar, "Conformational Flexibility of Three–Way DNA Junctions Containing Unpaired Nucleotides," *Biochemistry* 35:7959–7967 [1996].

Yoshioka et al., "Detection of Hepatitis C Virus by Polymerase Chain Reaction and Response to Interferon–α Therapy: Relationship to Genotypes of Hepatitis C Virus," *Hepatology* 16:293–299 [1992].

Youil, et al., "Detection of 81 of 81 Known Mouse β–Globin Promotor Mutations with T4 Endonuclease VII—The EMC Method," *Genomics*, 32:431 [1996].

Yule, "Amplification–Based Diagnostics Target TB," *Bio/Technology* 12:1335–1337 [1994].

Zarrinkar and Williamson, "Kinetic Intermediates in RNA Folding," *Science* 265:918–924 [1994].

Zarrinkar and Williamson, "The kinetic folding pathway of the Tetrahymena ribozyme reveals possible similarities between RNA and protein folding," *Nat. Struct. Biol.* 3:432–438 [1996].

Zhong et al., "Effect of T–T Base Mismatches on Three–Arm DNA Junctions," *Biochemistry* 32:6898–6907 [1993].

Zucker, "On Finding All Suboptimal Foldings of an RNA Molecule," *Science* 244:48–52 [1989].

Zuker and Jacobson, "'Well–Determined' Regions in RNA Secondary Structure Prediction: Analysis of Small Subunit Ribosomal RNA," *Nucleic Acids Research* 23(14):2791–2798 [1995].

Azhayeve et al., "Looped Oligonucleotides Form Stable Hybrid Complexes with a Single–Stranded DNA," *Nucl. Acids Res.* 23(7):1170–1176 [1995].

Blume et al., "Divalent Transition Metal Cations Counteract Potassium–Induced Quadruplex Assembly of Oligo(dG) Sequences," *Nucl. Acids Res.* 25(3):617–625 [1997].

Brossalina and Toulme, "A DNA Hairpin as a Target for Antisense Oligonucleotides," *J. Am. Chem. Soc.* 115:796–797 [1993].

Butorin et al., "Comparison of the Hydrolysis Patterns of Several tRNAs by Cobra Venom Ribonuclease in Different Steps of the Aminoacylation Reaction," *Eur. J. Biochem.* 121:587–595 [1982].

Cech, "Structure and Mechanism of the Large Catalytic RNAs: Group I and Group II Introns and Ribonuclease P," Chapter 11 in *The RNA World,* Cold Spring Harbor Laboratory Press, New York, pp. 239–269 [1993].

Clark, "DNA Synthesis on Discontinuous Templates by DNA Polymerase I of *Escherichia coli,*" *Gene* 104:75–80 [1991].

Cload et al., "Kinetic and Thermodynamic Analysis of RNA Binding by Tethered Oligonucleotide Probes: Alternative Structures and Conformational Changes," *J. Am. Chem. Soc.* 115(12):5005–5014 [1993].

Delihas et al., "Natural Antisense RNA/Target RNA Interactions: Possible Models for Antisense Oligonucleotide Drug Design," *Nature Biotech.* 15:751–753 [1997].

DeRisi et al., "Use of a cDNA Microarray to Analyse Gene Expression Patterns in Human Cancer," *Nature Genetics* 14:457–460 [1996].

Derrick and Horowitz, "Probing Structural Differences Between Native and In Vitro Transcribed *Escherichia coli* Valine Transfer RNA: Evidence For Stable Base Modification–Dependent Conformers," *Nucl. Acids Res.* 21(21):4948–4953 [1993].

Frischer et al., "Differential sensitivity of 16S rRNA targeted oligonucleotide probes used for fluorescence in situ hybridization is a result of ribosomal higher order structure," *Can. J. Microbiol* 42:1061–1071 [1996].

Guo et al., "Asymmetric Structure of a Three–Arm DNA Junction," *Biochemistry* 29:10927–10934 [1990].

Hoheisel, "Sequence–independent and linear variation of oligonucleotide DNA binding stabilities," *Nucl. Acids Res.* 24(3):430–432 [1996].

Lane et al., "The Thermodynamic Advantage of DNA Oligonucleotide 'Stacking Hybridization' Reactions: Energetics of a DNA Nick," *Nucl. Acids Res.* 25(3):611–616 [1997].

Lilley and Kemper, "Cruciform–Resolvase Interactions in Supercoiled DNA," *Cell* 26:413–422 [1984].

Lima et al., "Combinatorial Screening and Rational Optimization for Hybridization to Folded Hepatitis C Virus RNA of Oligonucleotides with Biological Antisense Activity," *J. Biol. Chem.* 272(1):626–638 [1997].

Lu et al., "Effect of Sequence on the Structure of Three–Arm DNA Junctions," *Biochemistry* 30(24):5815–5820 [1991].

Ma et al., "Three–Arm Nucleic Acid Junctions are Flexible," *Nucl. Acid Res.* 14:9745–9753 [1986].

Malygin et al.,"Hybridization of Two Oligodeoxynucleotides to Both Strands of an RNA Hairpin Structure Increases the Efficiency of RNA–DNA Duplex Formation," *FEBS Letters* 392:114–116 [1996].

Matveeva et al., "A Rapid In Vitro Method for Obtaining RNA Accessibility Patterns for Complementary DNA Probes: Correlation with an Intracellular Pattern and Known RNA Structures," *Nucl. Acids Res.* 25(24):5010–5016 [1991].

Milner et al., "Selecting Effective Antisense Reagents On Combinatorial Oligonucleotide Arrays," *Nature Biotech.* 15:537–541 [1997].

Milosavljevic et al., "DNA Sequence Recognition by Hybridization to Short Oligomers: Experimental Verification of the Method on the *E. coli* Genome," *Genomics* 37:77–86 [1996].

Mishra et al., "Targeting nucleic acid secondary structures by antisense oligonucleotides designed through in vitro selection," *Proc. Natl. Acad. Sci. USA* 93:10679–10684 [1996].

Pan et al., "Divalent Metal Ions in RNA Folding and Catalysis," Chapter 12 in *The RNA World,* Cold Spring Harbor Laboratory Press, New York, pp. 271–302 [1993].

Parinov et al., "DNA Sequencing by Hybridization to Microchip Octa– and Decanucleotides Extended by Stacked Pentanucleotides," *Nucl. Acids Res.* 24(15):2998–3004 [1996].

Parsch et al., "Site–Directed Mutations Reveal Long–Range Compensatory Interactions in the Adh gene of *Drosophila melanogaster,*" *Proc. Natl. Acad. Sci. USA* 94:928–933 [1997].

Rosen and Patel, "Structural Features of a Three–Stranded DNA Junction Containing a C–C Junctional Bulge," *Biochemistry* 32:6576–6587 [1993].

Schuster et al., "RNA Structures and Folding: From Conventional to New Issues in Structure Predictions," *Cur. Opin. in Struct. Biol.* 7:229–235 [1997].

Southern, "DNA fingerprinting by hybridization to oligonucleotide arrays," *Electrophoresis* 16(9):1539–1542 [1995].

Southern, "DNA chips: analyzing sequence by hybridization to oligonucleotides on a large scale," *TIG* 12(3):1–6 [1996].

Strobel and Doudna, "RNA Seeing Double: Close–Packing of Helices in RNA Tertiary Structure," *TIBS Reviews* 22:262–266 [1997].

Suo and Johnson, "RNA Secondary Structure Switching During DNA Synthesis Catalyzed by HIV–1 Reverse Transcriptase," *Biochemistry* 36:14778–14785 [1997].

Walter et al., "Coaxial Stacking of Helixes Enhances Binding of Oligoribonucleotides and Improves Predictions of RNA Folding," *Proc. Natl. Acad. Sci USA* 91:9218–9222 [1994].

Weiler et al., "Hybridization Based DNA Screening on Peptide Nucleic Acid (PNA) Oligomer Arrays," *Nucl. Acids Res.* 25(14):2792–2799 [1997].

Welch et al., "Structures of Bulged Three–Way DNA Junctions," *Nucl. Acids Res.* 21(19):4548–4555 [1993].

Woese and Pace, "Probing RNA Structure, Function, and History by Comparative Analysis," Chapter 4 in *The RNA World*, Cold Spring Harbor Laboratory Press, New York, pp. 91–117 [1993].

Wyatt and Tinoco, "RNA Structural Elements and RNA Function," Chapter 18 in *The RNA World*, Cold Spring Harbor Laboratory Press, New York, pp. 465–496 [1993].

Ho et al., "Mapping of RNA accessible sites for antisense experiments with oligonucleotide libraries," *Nature Biotech* 16:59–63 [1998]).

Kirby et al., "Maintenance of pre–mRNA secondary structure by epistatic selection," *Proc. Natl. Acad. Sci. USA* 92:9047–9051 [1995].

Tabernero et al., "The Posttranscriptional Control Element of the Simian Retrovirus Type 1 Forms an Extensive RNA Secondary Structure Necessary for Its Function," *J. Virol.* 70:5998–6011 [1996].

Ladbury et al., "The Thermodynamics of Formation of a Three–Strand, DNA Three–Way Junction Complex," *Biochemistry* 33:6828–6833 [1994].

Leontis et al., "Stability and structure of three–way DNA junctions containing unpaired nucleotides," *Nucl. Acids Res.* 19:759–766 [1991].

Zhong et al., "Thermodynamics of dT—dT Base Pair Mismatching in Linear DNA Duplexes and Three–Arm DNa Junctions," *Biochemistry* 36:2485 2491 [1997].

Southern, "Detection of Specific Sequences Among DNA Fragments Separated by Gel Electrophoresis," *J. Mol. Biol,* 98:503–517 [1975].

\* cited by examiner

FIGURE 2
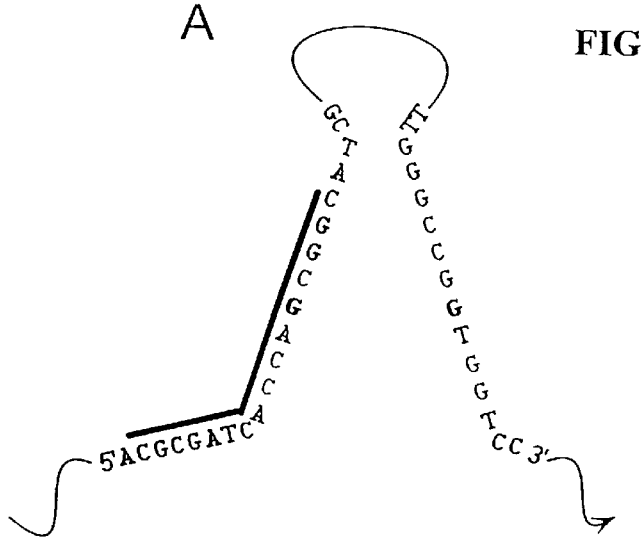
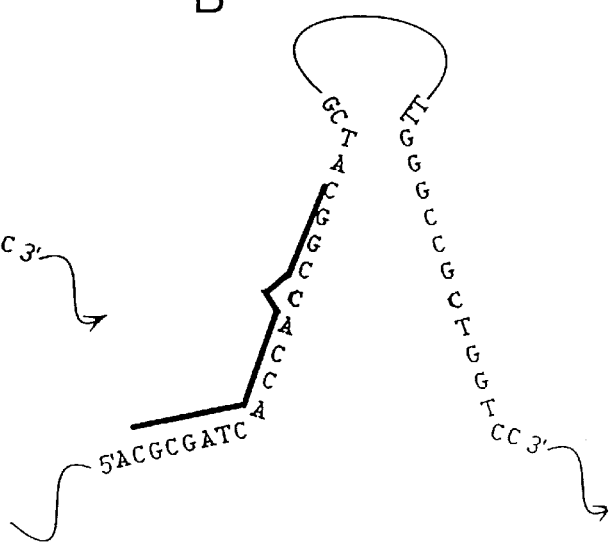
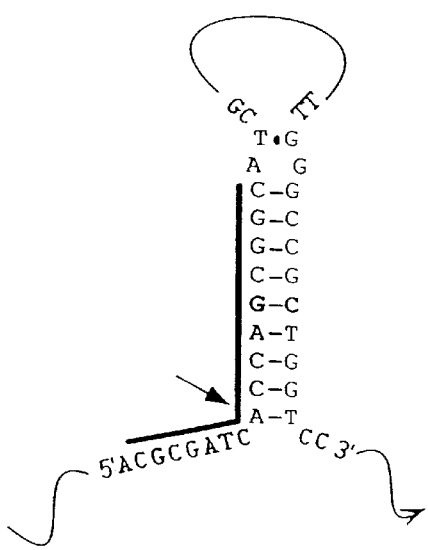
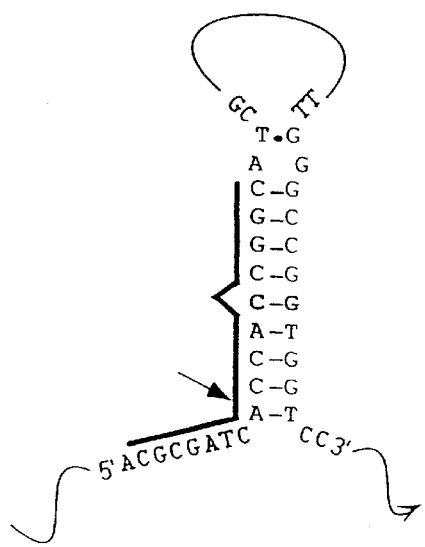

FIGURE 3
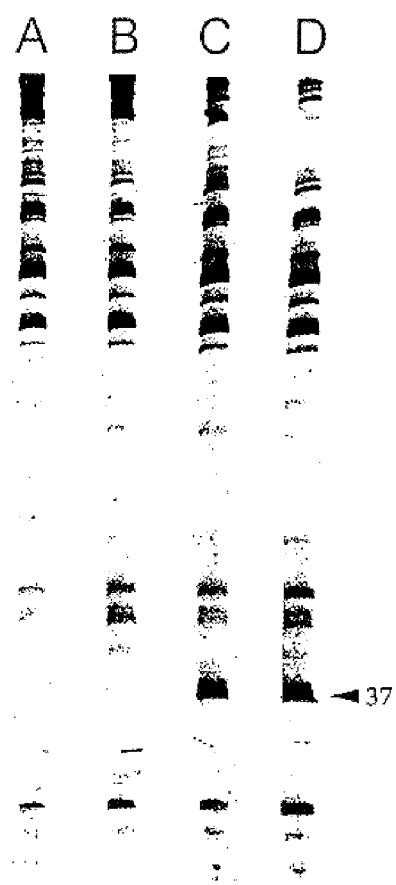
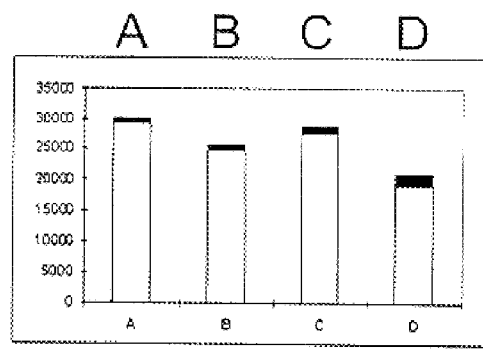
Structure  — — + +
Mismatch  — + — +

FIGURE 6

```
Consensus:GATTCTGTCT TCACGCAGAA AGCGTCTAGC CATGGCGTTA GTATGAGTGT CGTGCAGCCT
HCV 1a    ---------- ---------- ---------- ---------- ---------- ----------
HCV 1b    ---------- ---------- ---------- ---------- ---------- ----------
HCV 2c    ---------- ---------- ---------- -------C-- ---------- ----A-----
HCV 3a    ---------- ---------- ---------- ---------- ------C--- ----------

#249                   #251
          CCAGGACCCC CCCTCCCGGG AGAGCCATAG TGGTCTGCGG AACCGGTGAG TACACCGGAA
          ---------- ---------- ---------- ---------- ---------- ----------
          ---T------ ---------- ---------- ---------- ---------- ----------
          ---C------ ---------- ---------- ---A------ ---------- ----------
          ---------- ---------- ---------- ---------- ---------- ----------

#257
          TTGCCAGGAC GACCGGGTCC TTTCTTGGAT CAACCCGCTC AATGCCTGGA GATTTGGGCG
          ---------- ---------- ---------- ---------- ---------- ----------
          ---G--A--- ---T------ ---------- A-----A--- T----C--C- ----------
          -C---TG--GT ---------- ---------G ---------- ---A--CA-- -A--------
          ---------- ---------- ---------- ---------- ---------- ----------

#40       #261            #263
          TGCCCCCGCA AGACTGCTAG CCGAGTAGTG TTGGGTCGCG AAAGGCCTTG TGGTACTGCC
          ---------- ---------- ---------- ---------- ---------- ----------
          ----G----- ---------- ---------- -----C---- ---------- ----------
          ----G----- ---TCA---- ---------- -----T---- ---------- ----------
          ---------- ---------- ---------- ---------- ---------- ----------

TGATAGGGTG CTTGCGAGTG CCCCGGGAGG TCTCGTAGAC CGTGCAATC
          ---------- ---------- ---------- ---------- ---------
          ---------- ---------- ---------- ---------- ---------
          ---------- ---------- ---------- ------A--- ---------
          ---------- ---------- ---------- ---------- ---------
```

FIGURE 8A
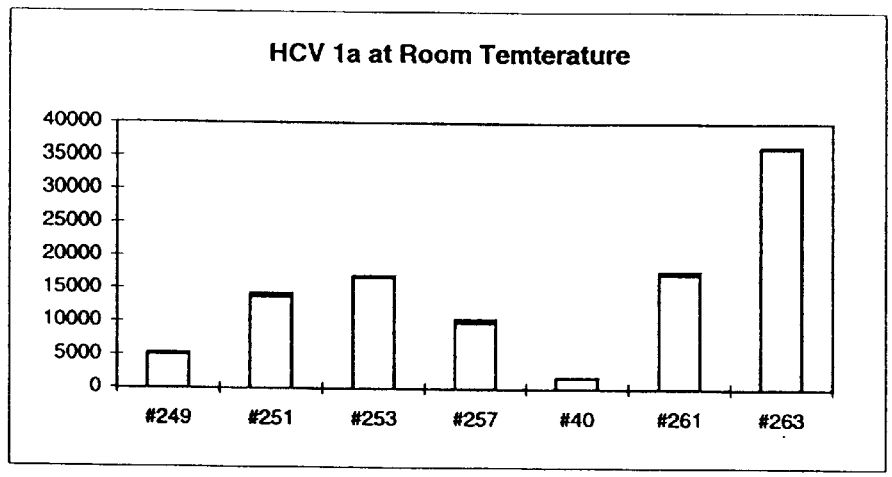
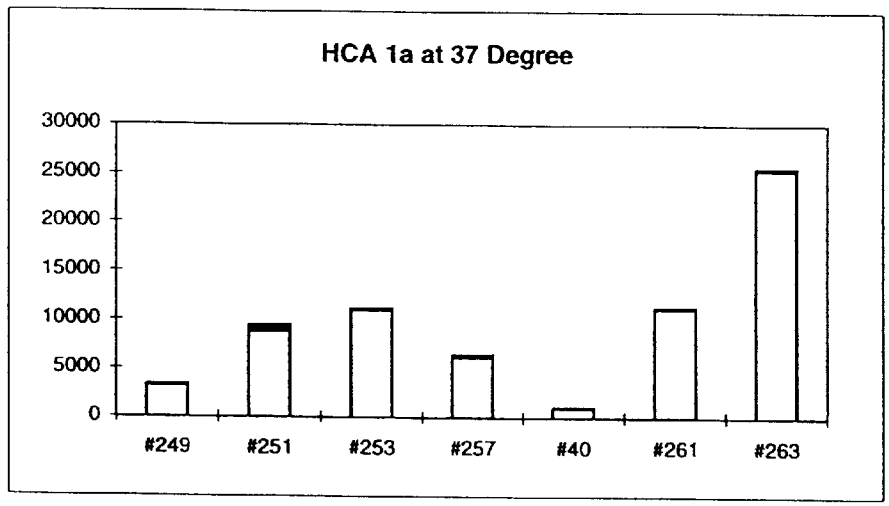
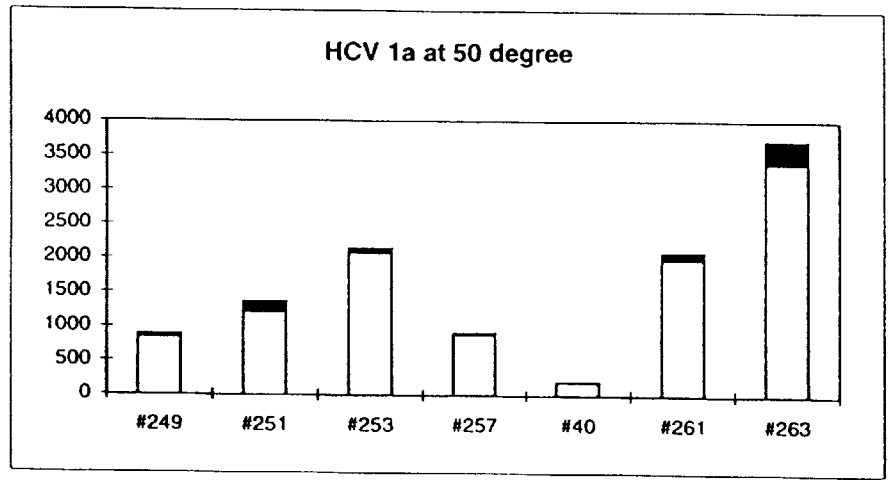

FIGURE 8B
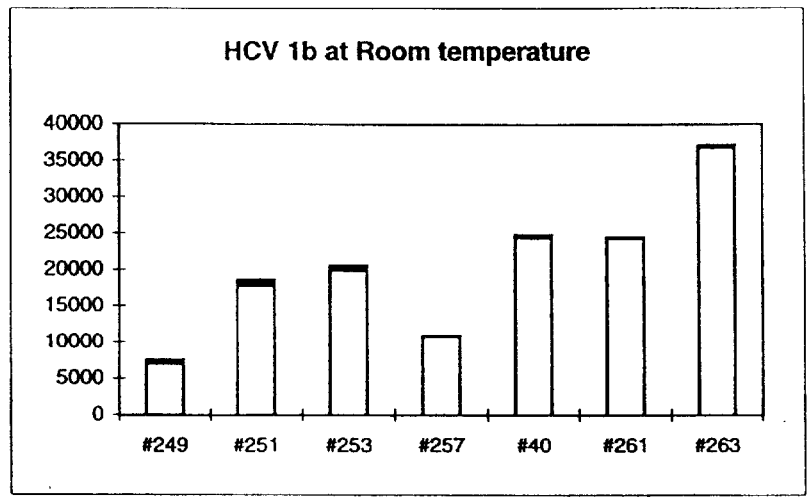
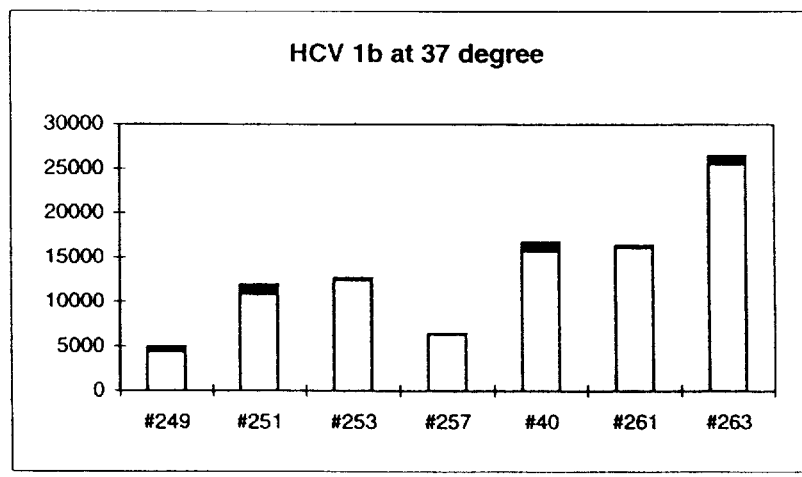
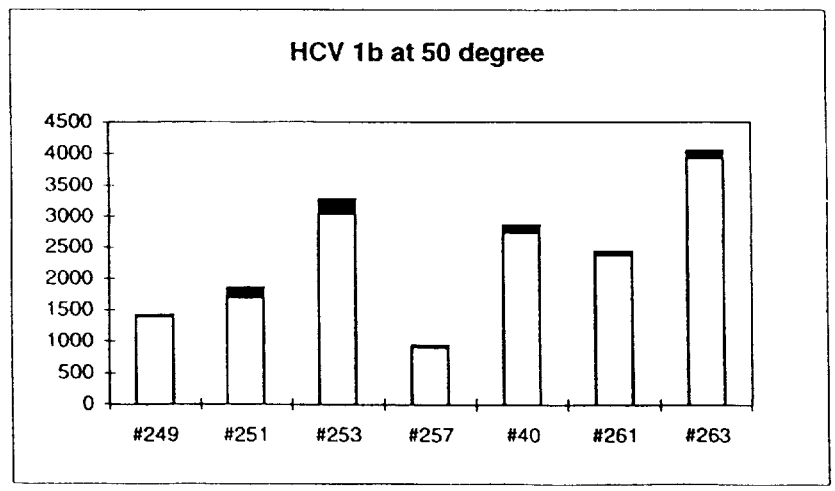

FIGURE 8C
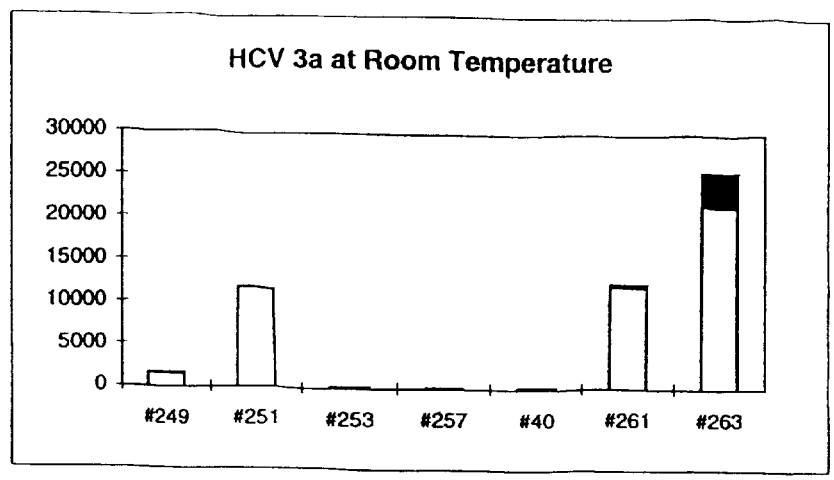
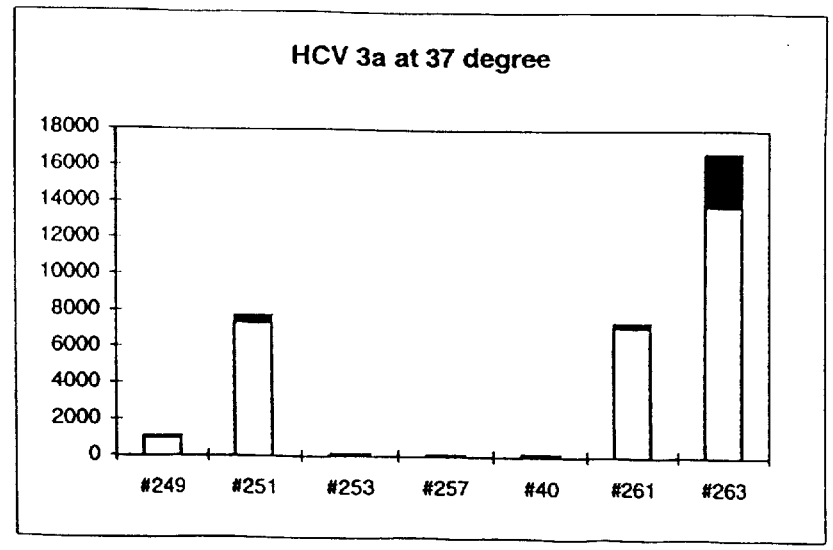
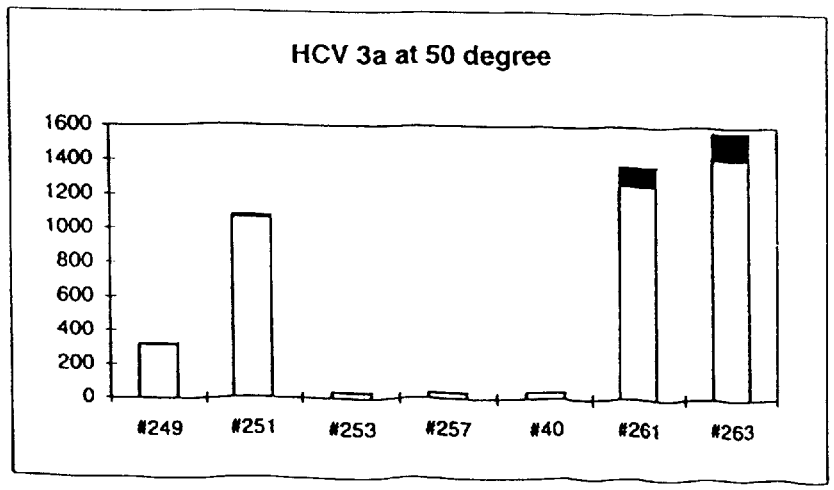

FIGURE 9D
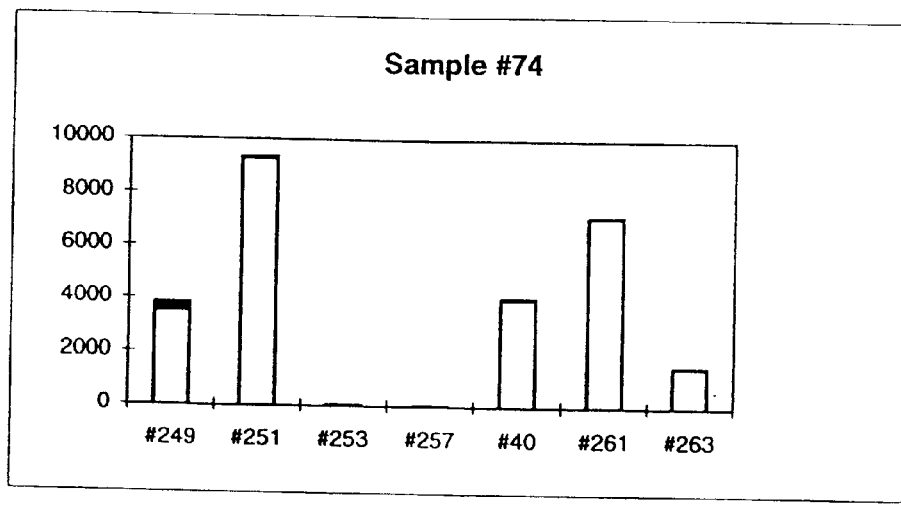
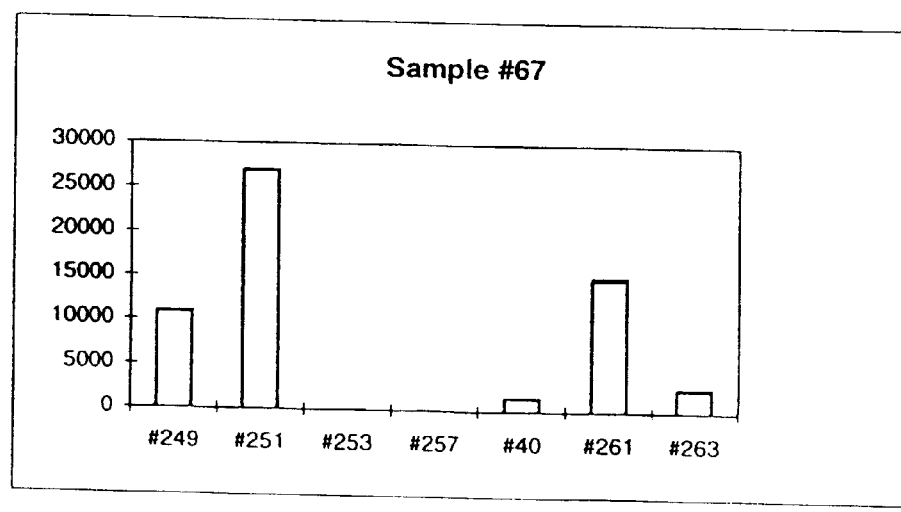

```
                     #2) 5' Biotin
                              |
                         T    A
                      C  G    A
                      A  T — A
                      G  C — G
                      A  T — A
                      C  G — C
                      A  T — A
                      G  C — G
                      C  G — C
                      G  C — G
#80) 5'-Fl-T G C T C T C T G G T    T G G T C T C T C G T A A T-3'
#FD91) 3' Biotin - C G A G A G A C C A - 5'
```

```
                         A
                      G  A
                      T — A
                      C — G
                      T — A
                      G — C
                      T — A
                      C — G
                      G — C
                      C — G
#80) 5'-Fl-T G C T C T C T G G T    T G G T C T C T C G T A A T-3'

#78) 3' - A G A C C A T T A C C A G A -Biotin 5'

#4) 3' - G A G A C C A T T A C C A G A G -Biotin 5'

#79) 3' - A G A G A C C A T T A C C A G A G A -Biotin 5'
```

```
#116) 3' - A G A G A C C A A C C A G A G A -Biotin 5'

#117) 3' - T A C C A G A G A -Biotin 5'

```
              A
           G     A
           T — A
           C — G
           T — A
           G — C
           T — A
           C — G
           G — C
           C — G
#80) 5'-Fl-TGCTCTCTGGT     TGGTCTCTCGTAAT-3'
#79) 3'-AGAGACCA—TT—ACCAGAGA-Biotin 5'

A
           G     A
           T — A
           C — G
           T — A
           G — C
           T — A
           C — G
           G — C
           C — G
#80) 5'-Fl-TGCTCTCTGGT     TGGTCTCTCGTAAT-3'

3'-AGAGACCA           ACCAGAGA-Biotin 5'
              T             T
       #115   T             T    #114
              A             A
              C             C
         A⟷C                 C⟷A
              A             A
              G             G
         C⟷A                 A⟷C
              G             G
              A             A
             /               \
       Biotin 5'              3'
```

FIGURE 14
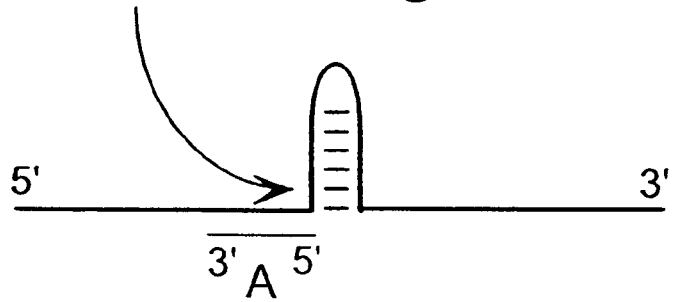
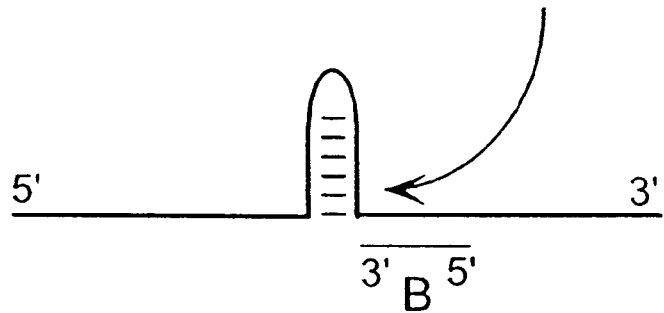
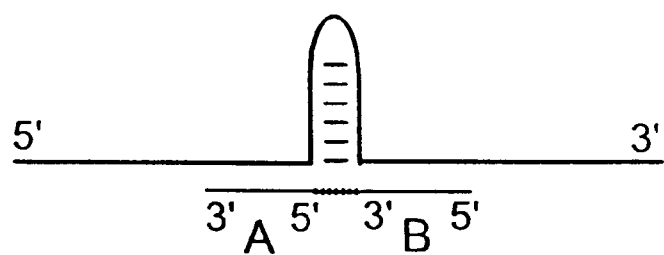

FIGURE 15

```
            1-------10--------20--------30--------40--------50--------60--------70-------80
            CTCGCAAGCACCCTATCAGGCAGTACCACAAGGCCTTTCGCGACCCAACACTACTCGGCTAGCAGTCTTGCGGGGCACG
1a
1b          ..........................................................⋮⋮............C....
2a/c        .......................................A..⋮...G............⋮⋮.................
3a          ..........................................⋮...........TGA..⋮C..................

------90-------100-------110-------120-------130-------140-------150------160
            CCCAAATCTCCAGGCATTGAGCGGGTTTATCCAAGAAAGGACCCGGTCGTCCTGGCAATTCCGGTGTACTCACCGTTCC
1a
1b          ........⋮⋮...........⋮⋮...G.................⋮⋮...........A..⋮T..⋮C..............
2a/c        .....⋮⋮.GG⋮.G...A..T..................GT........................AC..CA.⋮G.......
3a          .....T..⋮TG⋮.T.....⋮.....................

-----170-------180-------190-------200-------210-------220-------230------240
            GCAGACCACTATGGCTCTCCCGGAGGGGGGGTCCTGGAGGCTGCACGACACTCATACTAACGCCATGCTAGACGCTTTCTGC
1a
1b          ⋮....⋮⋮...............................................................
2a/c        ⋮⋮...⋮.....................G.........T.................................
3a          ⋮.....⋮....................................................G.................
```

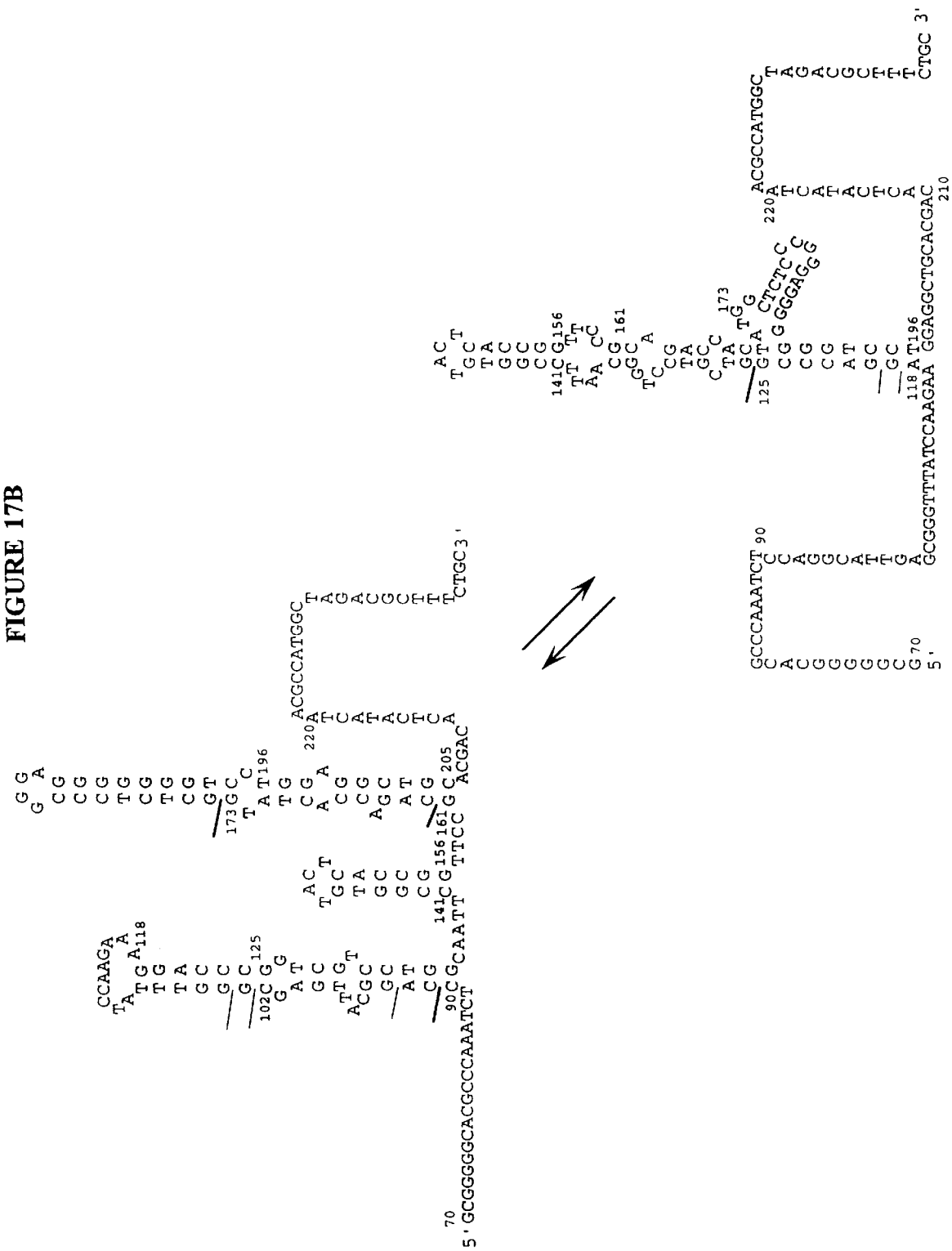

FIGURE 18C

```
       AAG
      C   A                    HCV 2a/c
     C    A118
    A  T A
     T G
      T G               G G A
      T A              G   G
      G C             C G
      G C             C G
      G C             C G
  102 T A125           T G
     G   T             C G
      A T G            T G
      G C              C G
      A T              G C
     T A T         173 G C 196
    C G C             T A T
      G C              T G
      G C              C G
      G C  A C         C G
      C G T  T          A  A
    90C G  G C          C G
      G C  T A         A C G
      G A  G C         A G C
      T A  G C         A T
         A T  C G  156 161 C G  T 205
5'———CACGCCCAA T C G     TTCC   T ACGACACT———3'
              141
```

(179-49-01) 3' GGCCAAGG $_{TT}$ TGCTGTGA 5'  b (192-72-01) 3' GGCCAAGG $_{AA}$ TGCTGTGA 5'  i (192-72-02) 3' GGCCAAGG $_{AC}$ TGCTGTGA 5'  j (192-72-03) 3' GGCCAAGG —— TGCTGTGA 5'  k (192-72-04) 3' GGCCTAGG $_{TT}$ TGCTGTGA 5'  c (192-72-05) 3' GGCCAAGG $_{TT}$ TGCAGTGA 5'  d

FIGURE 18D

HCV 3a

```
        CAAG
       C    A
       T    A
       T    A 118              G  A
       G    G              G  G
       T    G              G   G
       T    A              G    C  G
       G    C                   C  G
       G    C                   C  G
       G    C                   T  G
   102 C    G 125               C  G
       G    G                   T  G
       A    T                   C  T
       G    C                   G  C
      T T  A C              173 G  C
     A     C              T A    T 196
      T G  C                   T  G
       G    C       A C         C  G
       G  C     T    T          A  A
       T  A    G  C              C  G
    90 C  G    T  A           A  C  G
      T T  C   G  C           A G  C
       T G     G  C              A  T
       T  A    G  C              C  G
       A  T    C  G 156 161     G  C 205
5'——CACGCCCA A  T   C G   TTCC G   ACGACACT——3'
    (179-49-01) 3' GGCCAAGG TT TGCTGTGA 5'   b
    (192-72-01) 3' GGCCAAGG AA TGCTGTGA 5'   i
    (192-72-02) 3' GGCCAAGG AC TGCTGTGA 5'   j
    (192-72-03) 3' GGCCAAGG  — TGCTGTGA 5'   k
    (192-72-04) 3' GGCCTAGG TT TGCTGTGA 5'   c
    (192-72-05) 3' GGCCAAGG TT TGCAGTGA 5'   d
```

FIGURE 20A

HCV 1a

```
                    G G
                   G   A
                  C G
                  C G
                  C G
                  T G
                  C G
                  T G
                  C G
                  G T
              173 G C
                  T   C
                  A T 196
                  T G
                  C G
                  A   A
                  C G
                  C G
                  A G C
                  A T
                  C G
                  G C 205
5'—CAATTCCGGTGTACTCACCGGTTCC  C ACGACACT—3'
```

3'-<u>GGCCAAGGCGTCTGGTGA</u>—F1 5' (205-13-02)  a
3'-<u>GGCCAAGG</u>TT<u>TGCTGTGA</u>—F1 5' (179-49-01)  b
3'-<u>GGCCTAGG</u>TT<u>TGCTGTGA</u>—F1 5' (192-72-04)  c
3'-<u>GGCCAAGG</u>TT<u>TGCAGTGA</u>—F1 5' (192-72-05)  d
3'-<u>GGCCAAGG</u>—F15' (205-27-01)  e

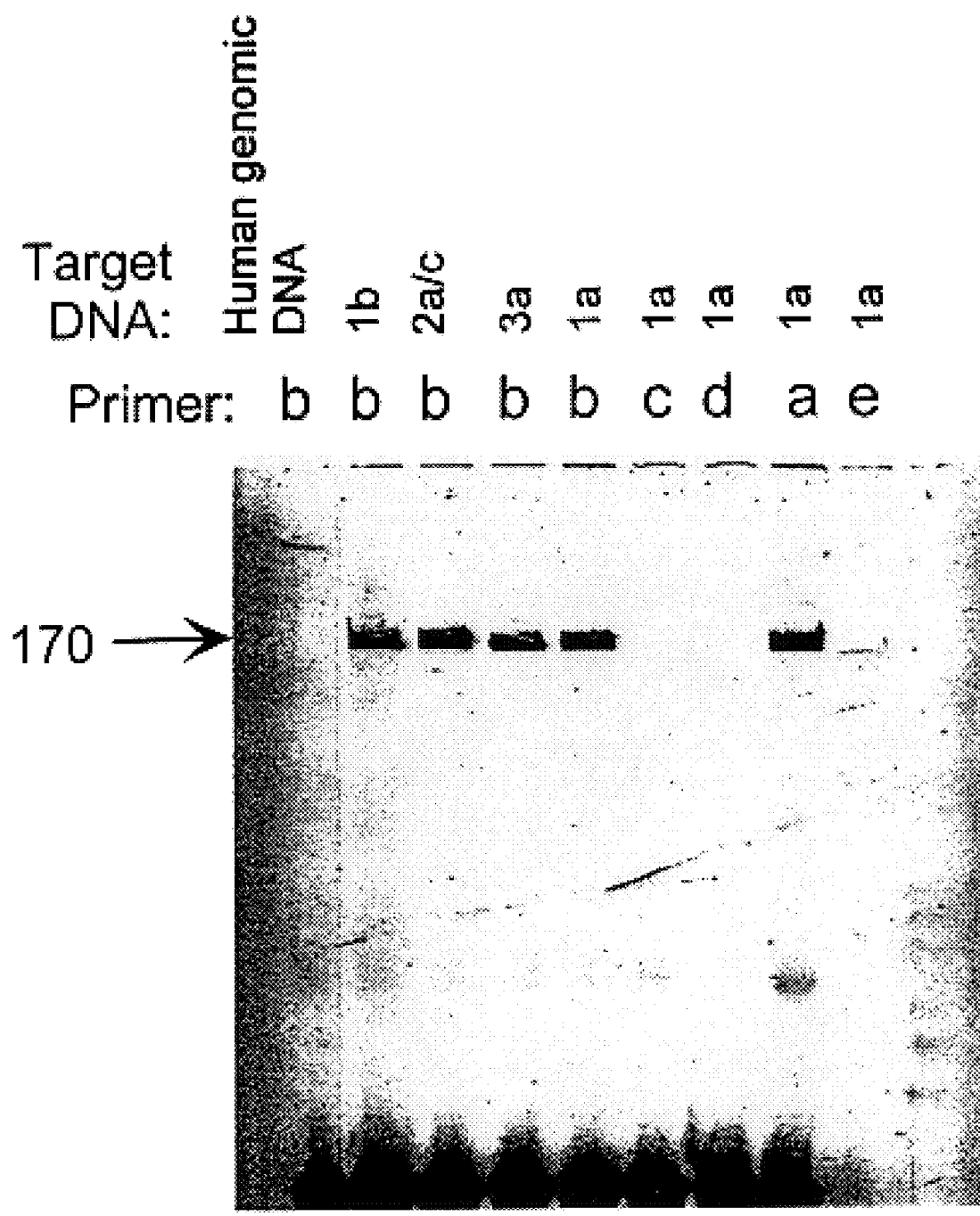

FIGURE 26

```
                    5'-ATTCCGGTGTACTCACCGGTTCCAAACGACACT-3' (205-13-01)  S.T.
f (192-96-01) 3'-TAAGGCCACATGAGT-5'
                                   3'-GGCCAAGGCGTCTGGTGA-Fl'5' (205-13-02)   a
                                                        TGCTGTGTGA
                                   3'-GGCCAAGG   TT          -Fl'5' (179-49-01)   b
                                                        TGCTGTGTGA
                                   3'-GGCCTAGG   TT          -Fl'5' (192-72-04)   c
                                                        TGCAGTGA
                                   3'-GGCCAAGG   TT          -Fl'5' (192-72-05)   d

3'-GGCCAAGG-Fl5' (205-27-01)   e
```

FIGURE 29B

```
                                                                S.T.
5'-ATTCCGGTGTACTTCACCGGTTCCAAACGACACT-3' (205-13-01)
                      3'-GGCCAAGGCGTCTGGTGA-F1'5' (205-13-02)      a
                      3'-GGCCAAGG_TT TGCTGTGA--F1'5' (179-49-01)   b
                      3'-GGCCTAGG_TT TGCTGTGA--F1'5' (192-72-04)   c
                      3'-GGCCAAGG_TT TGCAGTGA--F1'5' (192-72-05)   d
                      3'-GGCCAAGG-F15' (205-27-01)                 e
  3'-TAAGGCCACATGAGTG_T T T T--F1'5' (192-96-02)
g
```

TARGET-DEPENDENT REACTIONS USING STRUCTURE-BRIDGING OLIGONUCLEOTIDES

This invention was made with government support under Grant No. 5R44GM51704-03 awarded by the National Institutes of Health. The Government has certain rights in the invention.

FIELD OF THE INVENTION

The present invention relates to methods and compositions for analyzing nucleic acids, and in particular, methods and compositions for detection and characterization of nucleic acid sequences and sequence changes.

BACKGROUND OF THE INVENTION

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations. As nucleic acid sequence data for genes from humans and pathogenic organisms accumulates, the demand for fast, cost-effective, and easy-to-use tests for as yet unknown, as well as known, mutations within specific sequences is rapidly increasing.

A handful of methods have been devised to scan nucleic acid segments for mutations. One option is to determine the entire gene sequence of each test sample (e.g., a clinical sample suspected of containing bacterial strain). For sequences under approximately 600 nucleotides, this may be accomplished using amplified material (e.g., PCR reaction products). This avoids the time and expense associated with cloning the segment of interest. However, specialized equipment and highly trained personnel are required for DNA sequencing, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or, as noted above, the precise nucleotide sequence can be determined by partial chemical degradation or by primer extension in the presence of chain-terminating nucleotide analogs.

For detection of single-base differences between like sequences (e.g., the wild type and a mutant form of a gene), the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis). In this way, single point mutations can be detected by the creation or destruction of RFLPs.

Single-base mutations have also been identified by cleavage of RNA-RNA or RNA-DNA heteroduplexes using RNase A (Myers et al., Science 230:1242 [1985] and Winter et al., Proc. Natl. Acad. Sci. USA 82:7575 [1985]). Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817 [1990]). However, this method requires the use of osmium tetroxide and piperidine, two highly noxious chemicals which are not suited for use in a clinical laboratory. Enzymes such as the bacteriophage T4 endonuclease VII have been used in "Enzymatic Mismatch Cleavage: (EMC) (Youil, et al., Genomics, 32:431 [1996]). However, all of the mismatch cleavage methods lack sensitivity to some mismatch pairs, and all are prone to background cleavage at sites removed from the mismatch. Furthermore, the generation of purified fragments to be used in heteroduplex formation is both labor intensive and time consuming.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), *Nucleic Acids and Molecular Biology*, vol. 2, Springer-Verlag, Heidelberg [1988]). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167 [1987]). Recently, endonucleases encoded by group I introns have been discovered that might have greater than 12 base-pair specificity (Perlman and Butow, Science 246:1106 [1989]), but again, these are few in number.

If the change is not in a restriction enzyme recognition sequence, then allele-specific oligonucleotides (ASOs), can be designed to hybridize in proximity to the unknown nucleotide, such that a primer extension or ligation event can be used as the indicator of a match or a mis-match. Hybridization with radioactively labeled ASOs also has been applied to the detection of specific point mutations (Conner, Proc. Natl. Acad. Sci., 80:278 [1983]). The method is based on the differences in the melting temperature of short DNA fragments differing by a single nucleotide (Wallace et al., Nucl. Acids Res., 6:3543 [1979]). Similarly, hybridization with large arrays of short oligonucleotides is now used as a method for DNA sequencing (Bains and Smith, J. Theor. Biol., 135:303 [1988]) (Drmanac et al., Genomics 4:114 [1989]). To perform either method it is necessary to work under conditions in which the formation of mismatched duplexes is eliminated or reduced while perfect duplexes still remain stable. Such conditions are termed "high stringency" conditions. The stringency of hybridization conditions can be altered in a number of ways known in the art. In general, changes in conditions that enhance the formation of nucleic acid duplexes, such as increases in the concentration of salt, or reduction in the temperature of the solution, are considered to reduce the stringency of the hybridization conditions. Conversely, reduction of salt and elevation of temperature are considered to increase the stringency of the conditions. Because it is easy to change and control, variation of the temperature is commonly used to control the stringency of nucleic acid hybridization reactions.

Discrimination of hybridization based solely on the presence of a mismatch imposes a limit on probe length because effect of a single mismatch on the stability of a duplex is smaller for longer duplexes. For oligonucleotides designed to detect mutations in genomes of high complexity, such as human DNA, it has been shown that the optimal length for hybridization is between 16 and 22 nucleotides, and the temperature window within which the hybridization stringency will allow single base discrimination can be as large as 10° C. (Wallace [1979], supra). Usually, however, it is much narrower, and for some mismatches, such as G-T, it may be as small as 1 to 2° C. These windows may be even smaller if any other reaction conditions, such as temperature, pH, concentration of salt and the presence of destabilizing agents (e.g., urea, formamide, dimethylsulfoxide) alter the stringency. Thus, for successful detection of mutations using such high stringency hybridization methods, a tight control of all parameters affecting duplex stability is critical.

In addition to the degree of homology between the oligonucleotide probe and the target nucleic acid, efficiency of hybridization also depends on the secondary structure of the target molecule. Indeed, if the region of the target molecule that is complementary to the probe is involved in the formation of intramolecular structures with other regions of the target, this will reduce the binding efficiency of the probe. Interference with hybridization by such secondary structure is another reason why high stringency conditions are so important for sequence analysis by hybridization. High stringency conditions reduce the probability of secondary structure formation (Gamper et al., J. Mol. Biol., 197:349 [1987]). Another way to of reducing the probability of secondary structure formation is to decrease the length of target molecules, so that fewer intrastrand interactions can occur. This can be done by a number of methods, including enzymatic, chemical or thermal cleavage or degradation. Currently, it is standard practice to perform such a step in commonly used methods of sequence analysis by hybridization to fragment the target nucleic acid into short oligonucleotides (Fodor et al., Nature 364:555 [1993]).

ASOs have also been adapted to the PCR method. In this, or in any primer extension-based assay, the nucleotide to be investigated is positioned opposite the 3' end of a primer oligonucleotide. If the bases are complementary, then a DNA polymerase can extend the primer with ease; if the bases are mismatched, the extension may be blocked. Blocking of PCR by this method has had some degree of success, but not all mismatches are able to block extension. In fact, a "T" residue on the 3' end of a primer can be extended with reasonable efficiency when mis-paired with any of the non-complementary nucleotide when Taq DNA polymerase, a common PCR enzyme, is used (Kwok, et al., Nucl. Acids. Res. 18:999 [1990]). Further, if any of the enzymes having 3'-5' exonuclease "proofreading" activity (e.g., Vent DNA polymerase, New England Biolabs, Beverly Mass.) are used, the mismatch is first removed, then filled in with a matched nucleotide before further extension. This dramatically limits the scope of application of PCR in this type of direct mutation identification.

Two other methods of mutation detection rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in the melting properties of homoduplexes versus heteroduplexes differing in a single nucleotide can be used to detect the presence of mutations in the target sequences because of the corresponding changes in the electrophoretic mobilities of the hetero- and homo-duplexes. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463 [1990]). Attaching a GC clamp to one primer is critical to ensure that the amplified sequence has a low dissociation temperature (Sheffield et al., Proc. Natl. Acad. Sci., 86:232 [1989]; and Lerman and Silverstein, Meth. Enzymol., 155:482 [1987]). Modifications of the technique have been developed, using temperature gradient gels (Wartell et al., Nucl. Acids Res., 18:2699–2701 [1990]), and the method can be also applied to RNA:RNA duplexes (Smith et al., Genomics 3:217 [1988]).

Limitations on the utility of DGGE include the requirement that the denaturing conditions must be optimized for each specific nucleic acid sequence to be tested. Furthermore, the method requires specialized equipment to prepare the gels and maintain the high temperatures required during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405 [1991]). CDGE requires that gels be performed under different denaturant conditions in order to reach high efficiency for the detection of unknown mutations. Both DGGE and CDGE are unsuitable for use in clinical laboratories.

A technique analogous to DGGE, termed temperature gradient gel electrophoresis (TGGE), uses a thermal gradient rather than a chemical denaturant gradient (Scholz et al., Hum. Mol. Genet., 2:2155 [1993]). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34–38, [1991]) and is based on the observation that single strands of nucleic acid can take on characteristic conformations under non-denaturing conditions, and these conformations influence electrophoretic mobility. The complementary strands assume sufficiently different structures that the two strands may be resolved from one another. Changes in the sequence of a given fragment will also change the conformation, consequently altering the mobility and allowing this to be used as an assay for sequence variations (Orita, et al., Genomics 5:874 [1989]).

The SSCP process involves denaturing a DNA segment (e.g., a PCR product) that is usually labeled on both strands, followed by slow electrophoretic separation on a nondenaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

The dideoxy fingerprinting (ddF) technique is another technique developed to scan genes for the presence of unknown mutations (Liu and Sommer, PCR Methods Applic, 4:97 [1994]). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200–300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Another method of detecting sequence polymorphisms based on the conformation assumed by strands of nucleic acid is the Cleavase® Fragment Length Polymorphism (CFLP®) method (Brow et al., J. Clin. Microbiol., 34:3129 [1996]; PCT International Application No. PCT/US95/14673 [WO 96/15267]; co-pending Application Ser. Nos. 08/484,956 and 08/520,946). This method uses the actions of a structure specific nuclease to cleave the folded structures, thus creating a set of product fragments that can by resolved by size (e.g., by electrophoresis). This method is much less sensitive to size so that entire genes, rather than gene fragments, may be analyzed.

In many situations (e.g., in many clinical laboratories), electrophoretic separation and analysis may not be technically feasible, or may not be able to accommodate the processing of a large number of samples in a cost-effective manner. There is a clear need for a method of analyzing the characteristic conformations of nucleic acids without the need for either electrophoretic separation of conformations or fragments or for elaborate and expensive methods of visualizing gels (e.g., darkroom supplies, blotting equipment or fluorescence imagers).

In addition to the apparently fortuitous folded conformations that may be assumed by any nucleic acid segment, as noted above, the folded structures assumed by some nucleic acids are linked in a variety of ways to the function of that nucleic acid. For example, tRNA structure is critical to its proper function in protein assembly, ribosomal RNA (rRNA) structures are essential to the correct function of the ribosome, and correct folding is essential to the catalytic function of Group I self-splicing introns (See e.g., the chapters by Woese and Pace (p. 91), Noller (p. 137), and Cech (p. 239) in Gesteland and Atkins (eds.), *The RNA World*, Cold Spring Harbor Laboratory Press, Cold Spring Harbor, N.Y. [1993]). Folded structures in viral RNAs have been linked to infectivity (Proutski et al., J Gen Virol., 78(Pt 7):1543–1549 [1997], altered splicing (Ward, et al., Virus Genes 10:91 [1995]), translational frameshifting (Bidou et al., RNA 3:1153 [1997]), packaging (Miller, et al. J Virol., 71:7648 [1997]), and other functions. In both prokaryotes and eukaryotes, RNA structures are linked to post-transcriptional control of gene expression through mechanisms including attenuation of translation (Girelli et al., Blood 90:2084 [1997], alternative splicing (Howe and Ares, Proc. Natl. Acad. Sci. USA 94:12467 [1997]) and signaling for RNA degradation (Veyrune et al, Oncogene 11:2127 [1995]). Messenger RNA secondary structure has also been associated with localization of that RNA within cells (Serano and Cohen, Develop., 121:3809–3818 [1995]). In DNA it has been shown that cruciform structures have also been tied to control of gene expression (Hanke et al., J. Mol. Biol., 246:63 [1995]). It can be seen from these few examples that the use of folded structures as signals within organisms is not uncommon, nor is it limited to non-protein-encoding RNAs, such as rRNAs, or to non-protein-encoding regions of genomes or messenger RNAs.

Some mutations and polymorphisms associated with altered phenotype act by altering structures assumed by nucleic acids. Any of the functions and pathways cited above may be altered, e.g., decreased or increased in efficacy, by such a structural alteration. Such alterations in function may be associated with medically relevant effects, including but not limited to tumor growth or morphology (Thompson et al., Oncogene 14:1715 [1997]), drug resistance or virulence (Mangada and Igarishi, Virus Genes 14:5 [1997], Ward et al., supra) in pathogens. For example, the iron availability in blood in controlled by the protein ferritin, an iron storage protein. Ferritin levels are controlled post-transcriptionally by binding of iron-regulatory proteins to a structure (an iron-responsive element, or IRE) on 5' untranslated region of the ferritin mRNA, thereby blocking translation when iron levels are low. Hereditary hyperferritinemia, an iron storage disorder linked to cataract formation, had been found in some cases to be caused by mutations in the IRE that alter or delete the structure, preventing translational regulation.

It can easily be appreciated from these few examples that ability to rapidly analyze nucleic acid structure would be a useful tool for both basic and clinical research and for diagnostics. Further, accurate identification of nucleic acid structures would facilitate the design and application of therapeutic agents targeted directly at nucleic acids, such as antisense oligonucleotides, aptamers and peptide nucleic acid agents. The present invention provides methods for designing oligonucleotides that will interact with folded nucleic acids. It is contemplated that such oligonucleotides may be used for either diagnostic (i.e., detection or analysis of structure) or therapeutic (i.e., alteration of structure function) purposes. When used to detect nucleic acid structure, it is contemplated that the resulting oligonucleotide/folded nucleic acid target complexes may be detected directly (e.g., by capture), or may be detected as the result of a further catalyzed reaction that is enabled by the complex formation, including but not limited to a ligation, a primer extension, or a nuclease cleavage reaction.

It will easily be appreciated by those skilled in the art that performance of bridging oligonucleotides in these basic enzymatic reactions is indicative of their utility in assays that are based on reiterative performance of these basic reactions, including but not limited to cycle sequencing, polymerase chain reaction, ligase chain reaction, cycling probe reaction and the Invader™ invasive cleavage reaction. The present invention provides methods of using the bridging oligonucleotides in each of the basic enzymatic reaction systems, and in the Invader™ invasive cleavage system.

SUMMARY OF THE INVENTION

The present invention relates to methods and compositions for treating nucleic acid, and in particular, methods and compositions for detection and characterization of nucleic acid sequences and sequence changes. The present invention provides methods for examining the conformations assumed by single strands of nucleic acid, forming the basis of novel methods of detection of specific nucleic acid sequences. The present invention contemplates use of novel detection methods for, among other uses, clinical diagnostic purposes, including but not limited to the detection and identification of pathogenic organisms.

The present invention contemplates using the interactions between probe oligonucleotides and folded nucleic acid strands in methods for detection and characterization of nucleic acid sequences and sequence changes. In another embodiment, the present invention contemplates the use of structure based nucleic acid interactions in the analysis of particular structured regions of nucleic acids, as a determination of function or alteration of function. A complex formed by the specific interaction (i.e., reproducible and predictable under a given set of reaction conditions) of a probe with a target nucleic acid sequence is referred to herein as a "probe/folded target nucleic acid complex." The interactions contemplated may be a combination of standard hybridization of oligonucleotides to contiguous, co-linear complementary bases, or may include standard base pairing to non-contiguous regions of complementarity on a strand of nucleic acid to be analyzed. In this context, the term "standard base pairing" refers to hydrogen bonding that occurs between complementary bases, adenosine to thymidine or uracil and guanine to cytosine to form double helical structures of the A or B form. Such standard base pairing may also be referred to as Watson-Crick base pairing. It is contemplated that the interactions between the oligonucleotides of the present invention (i.e., the probes and the targets) may include non-standard nucleic acid interactions known in the art, such as triplex structures, quadraplex aggregates, and the multibase hydrogen bonding such as is observed within nucleic acid tertiary structures, such as those found in tRNAs. It is contemplated that in one embodiment, the interactions between the oligonucleotides of the present invention may consist primarily of non-standard nucleic acid interactions. In one embodiment, the specific probe/folded target nucleic acid complex uses oligonucleotides that lack unique complementarity to each other (e.g., the shorter nucleic acid probe lacks segments that are long enough to be complementary to only a single site within the longer nucleic acid or its complement).

The present invention contemplates the use of probes that are designed to interact with non-contiguous regions of complementarity. In one embodiment, such probes are constructed by incorporating within a single oligonucleotide segments that are complementary to two or more non-contiguous regions in the target nucleic acid of interest.

In another embodiment, this mixture is present in an aqueous solution. The invention is not limited by the nature of the aqueous solution employed. The aqueous solution may contain mono- and divalent ions, non-ionic detergents, buffers, stabilizers, etc.

In one embodiment, the present invention provides a method, comprising: a) providing: i) a folded target having a deoxyribonucleic acid (DNA) sequence comprising one or more double stranded regions and one or more single stranded regions; and ii) one or more oligonucleotide probes complementary to at least a portion of the folded target; and b) mixing the folded target and the one or more probes under conditions such that the probe hybridizes to the folded target to form a probe/folded target complex. The degree of complementarity between the probes and the target nucleic acids may be complete or partial (e.g., contain at least one mismatched base pair). The method is not limited by the nature of the target DNA employed to provide the folded target DNA. In one embodiment, the target DNA comprises single-stranded DNA. In another embodiment, the target DNA comprises double-stranded DNA. Folded target DNAs may be produced from either single-stranded or double-stranded target DNAs by denaturing (e.g., heating) the DNA and then permitting the DNA to form intra-strand secondary structures. The method is not limited by the manner in which the folded target DNA is generated. The target DNA may be denatured by a variety of methods known to the art including heating, exposure to alkali, etc. and then permitted to renature under conditions that favor the formation of intra-strand duplexes (e.g., cooling, diluting the DNA solution, neutralizing the pH, etc.).

The method is also not limited by the nature of the oligonucleotide probes; these probes may comprise DNA, RNA, PNA and combinations thereof as well as comprise modified nucleotides, universal bases, adducts, etc.

In a preferred embodiment, the method further comprises detecting the presence of the probe/folded target complex. When a detection step is employed either the probe or the target DNA (or both) may comprise a label (i.e., a detectable moiety); the invention is not limited by the nature of the label employed or the location of the label (i.e., 5' end, 3' end, internal to the DNA sequence). A wide variety of suitable labels are known to the art and include fluorescein, tetrachlorofluorescein, hexachlorofluorescein, Cy3, Cy5, digoxigenin, radioisotopes (e.g., $^{32}$P, $^{35}$S). In another preferred embodiment, the method further comprises quantitating the amount of probe/folded target complex formed. The method is not limited by the means used for quantification; when a labeled folded target DNA is employed (e.g., fluorescein or $^{32}$P) the art knows means for quantification (e.g., determination of the amount of fluorescence or radioactivity present in the probe/folded target complex).

In a preferred embodiment, the probe in the probe/folded target complex is hybridized to a single stranded region of the folded target. In another preferred embodiment, the probe comprises an oligonucleotide having a moiety that permits its capture by a solid support. The invention is not limited by the nature of the moiety employed to permit capture. Numerous suitable moieties are known to the art, including but not limited to, biotin, avidin and streptavidin. Further, it is known in the art that many small compounds, such as fluorescein and digoxigenin may serve as haptens for specific capture by appropriate antibodies. Protein conjugates may also be used to allow specific capture by antibodies.

In a preferred embodiment the detection of the presence of the probe/folded target complex comprises exposing the probe/folded target complex to a solid support under conditions such that the probe is captured by the solid support. As discussed in further detail below, numerous suitable solid supports are known to the art (e.g., beads, particles, dipsticks, wafers, chips, membranes or flat surfaces composed of agarose, nylon, plastics such as polystyrenes, glass or silicon) and may be employed in the present methods.

In a particularly preferred embodiment, the moiety comprises a biotin moiety and the solid support comprises a surface having a compound capable of binding to the biotin moiety, the compound selected from the group consisting of avidin and streptavidin.

In another embodiment, the folded target comprises a deoxyribonucleic acid sequence having a moiety that permits its capture by a solid support; as discussed above a number of suitable moieties are known and may be employed in the present method. In yet another embodiment, the detection of the presence of the probe/folded target complex comprises exposing the probe/folded target complex to a solid support under conditions such that the folded target is captured by the solid support. In a preferred embodiment, the moiety comprises a biotin moiety and the solid support comprises a surface having a compound capable of binding to the biotin moiety, the compound selected from the group consisting of avidin and streptavidin.

In a preferred embodiment, the probe is attached to a solid support; the probe is attached to the solid support in such a manner that the probe is available for hybridization with the folded target nucleic acid. the invention is not limited by the means employed to attach the probe to the solid support. The probe may be synthesized in situ on the solid support or the probe may be attached (post-synthesis) to the solid support via a moiety present on the probe (e.g., using a biotinylated probe and solid support comprising avidin or streptavidin). In another preferred embodiment, the folded target nucleic acid is attached to a solid support; this may be accomplished for example using moiety present on the folded target (e.g., using a biotinylated target nucleic acid and solid support comprising avidin or streptavidin).

The present invention also provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second oligonucleotide probes, the first oligonucleotide probe complementary to the first portion of the first and second folded targets and the second oligonucleotide probe complementary to the second portion of the first and second folded targets; and iv) a solid support comprising first, second, third and fourth testing zones, each zone capable of capturing and immobilizing the first and second oligonucleotide probes; b) contacting the first folded target with the first oligonucleotide probe under conditions such that the first probe binds to the first folded target to form a probe/folded target complex in a first mixture c) contacting the first folded target with the second oligonucleotide probes under conditions such that the second probe binds to the first folded target to form a probe/folded target complex in a second mixture; d) contacting the second folded target with the first oligonucleotide probe to form a third mixture; e) contacting the second folded target with the second oligonucleotide probe to form fourth mixture; and f) adding the first, second, third and fourth mixtures to the first, second, third and fourth testing zones of the solid support, respectively, under conditions such that the probes are captured and immobilized. The degree of complementarity between the probes and the target nucleic acids may be complete or partial (e.g., contain at least one mismatched base pair).

In a preferred embodiment, the first probe in step d) does not substantially hybridize to the second folded target; that is while it is not required that absolutely no formation of a first probe/second folded target complex occurs, very little of this complex is formed. In another preferred embodiment, the hybridization of the first probe in step d) to the second folded target is reduced relative to the hybridization of the first probe in step c) to the first folded target.

The method is not limited by the nature of the first and second targets. The first and second targets may comprise double- or single-stranded DNA or RNA. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA.

The present invention further provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second oligonucleotide probes, the first oligonucleotide probe complementary to the first portion of the first and second folded targets and second oligonucleotide probe complementary to the second portion of the first and second folded targets; and b) contacting the first and second folded targets with the solid support under conditions such that the first and second probes hybridize to the first folded target to form a probe/folded target complex. The invention is not limited by the nature of the first and second folded targets. The first and second targets may be derived from double- or single-stranded DNA or RNA. The probes may be completely or partially complementary to the target nucleic acids. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The invention is not limited by the nature of the solid support employed as discussed above.

In a preferred embodiment, the contacting of step b) comprises adding the first folded target to the first testing zone and adding the second folded target to the second testing zone. In another preferred embodiment, the first and second probes are immobilized in separate portions of the testing zones.

In a preferred embodiment, the first probe in the second testing zone does not substantially hybridize to the second folded target; that is while it is not required that absolutely no formation of a first probe/second folded target complex occurs, very little of this complex is formed. In another preferred embodiment, the first probe in the second testing zone hybridizes to the second folded target with a reduced efficiency compared to the hybridization of the first probe in first testing zone to the first folded target.

In one embodiment, the first and second folded targets comprise DNA. In another embodiment, the first and second folded targets comprise RNA.

The present invention also provides a method for treating nucleic acid, comprising: a) providing: i) a nucleic acid target and ii) one or more oligonucleotide probes; b) treating the nucleic acid target and the probes under conditions such that the target forms one or more folded structures and interacts with one or more probes; and c) analyzing the complexes formed between the probes and the target. In a preferred embodiment, the method further comprises providing a solid support for the capture of the target/probe complexes. Such capture may occur after the formation of the structures, or either the probe or the target my be bound to the support before complex formation.

The method is not limited by the nature of the nucleic acid target employed. In one embodiment, the nucleic acid of step (a) is substantially single-stranded. In another embodiment, the nucleic acid is RNA or DNA. It is contemplated that the nucleic acid target comprise a nucleotide analog, including but not limited to the group comprising 7-deaza-dATP, 7-deaza-dGTP and dUTP. The nucleic acid target may be double stranded. When double-stranded nucleic acid targets are employed, the treating of step (b) comprises: i) rendering the double-stranded nucleic acid substantially single-stranded; and ii) exposing the single-stranded nucleic acid to conditions such that the single-stranded nucleic acid has secondary structure. The invention is not limited by the method employed to render the double-stranded nucleic acid substantially single-stranded; a variety of means known to the art may be employed. A preferred means for rendering double stranded nucleic acid substantially single-stranded is by the use of increased temperature.

In a preferred embodiment, the method further comprises the step of detecting the one or more target/probe complexes. The invention is not limited by the methods used for the detection of the complex(es).

It is contemplated that the methods of the present invention be used for the detection and identification of microorganisms. It is contemplated that the microorganism(s) of the present invention be selected from a variety of microorganisms; it is not intended that the present invention be limited to any particular type of microorganism. Rather, it is intended that the present invention will be used with organisms including, but not limited to, bacteria, fungi, protozoa, ciliates, and viruses. It is not intended that the microorganisms be limited to a particular genus, species, strain, or serotype. Indeed, it is contemplated that the bacteria be selected from the group comprising, but not limited to members of the genera Campylobacter, Escherichia, Mycobacterium, Salmonella, Shigella, and Staphylococcus. In one preferred embodiment, the microorganism(s) comprise strains of multi-drug resistant *Mycobacterium tuberculosis*. It is also contemplated that the present invention be used with viruses, including but not limited to hepatitis C virus, human immunodeficiency virus, simian immunodeficiency virus, and influenza virus (e.g., influenza type A)

Another embodiment of the present invention contemplates a method for detecting and identifying strains of microorganisms, comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes. In one embodiment, the method further comprises the step of capturing the complexes to a solid support. In yet another embodiment, the method further comprises the step of detecting the captured complexes. In one preferred embodiment, the present invention further comprises comparing the detected from the extracted nucleic acid isolated from the sample with separated complexes derived from one or more reference microorganisms. In such a case the sequence of the nucleic acids from one or more reference microorganisms may be related but different (e.g., a wild type control for a mutant sequence or a known or previously characterized mutant sequence).

In an alternative preferred embodiment, the present invention further comprises the step of isolating a polymorphic locus from the extracted nucleic acid after the extraction step, so as to generate a nucleic acid target, wherein the target is contacted with one or more probe oligonucleotides. In one embodiment, the isolation of a polymorphic locus is accomplished by polymerase chain reaction amplification. In an alternate embodiment, the polymerase chain reaction is conducted in the presence of a nucleotide analog, including but not limited to the group comprising 7-deaza-dATP, 7-deaza-dGTP and dUTP. It is contemplated that the polymerase chain reaction amplification will employ oligonucleotide primers matching or complementary to consensus gene sequences derived from the polymorphic locus. In one embodiment, the polymorphic locus comprises a ribosomal RNA gene. In a particularly preferred embodiment, the ribosomal RNA gene is a 16S ribosomal RNA gene.

The present invention also contemplates a process for creating a record reference library of genetic fingerprints characteristic (i.e., diagnostic) of one or more alleles of the various microorganisms, comprising the steps of providing a nucleic acid target derived from microbial gene sequences; comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes; detecting the captured complexes; and maintaining a testable record reference of the captured complexes.

By the term "genetic fingerprint" it is meant that changes in the sequence of the nucleic acid (e.g., a deletion, insertion or a single point substitution) alter both the sequences detectable by standard base pairing, and alter the structures formed, thus changing the profile of interactions between the target and the probe oligonucleotides (e.g., altering the identity of the probes with which interaction occurs and/or altering the site/s or strength of the interaction). The measure of the identity of the probes bound and the strength of the interactions constitutes an informative profile that can serve as a "fingerprint" of the nucleic acid, reflecting the sequence and allowing rapid detection and identification of variants.

The methods of the present invention allow for simultaneous analysis of both strands (e.g., the sense and antisense strands) and are ideal for high-level multiplexing. The products produced are amenable to qualitative, quantitative and positional analysis. The present methods may be automated and may be practiced in solution or in the solid phase (e.g., on a solid support). The present methods are powerful in that they allow for analysis of longer fragments of nucleic acid than current methodologies.

The present invention further provides methods for determination of structure formation in nucleic acid targets, comprising the steps of: a) providing: i) a folded target having a deoxyribonucleic acid sequence comprising one or more double stranded regions, and one or more single stranded regions, and further comprising two or more non-contiguous portions, and one or more intervening regions; and ii) one or more bridging oligonucleotide probes complementary to two or more non-contiguous portions of the folded target; and b) mixing the folded target and one or more bridging oligonucleotide probes under conditions such that the bridging oligonucleotide probes hybridize to the folded target to form a probe/folded target complex.

In preferred embodiments, the one or more intervening regions of the folded targets comprise at least five nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In alternative embodiments, the method further comprises detecting the presence of the probe/folded target complex. In yet other embodiments, the method further comprises quantitating the amount of probe/folded target complex formed. In yet other embodiments of the method, the bridging oligonucleotide probe in the probe/folded target complex is hybridized to at least one single stranded region of the folded target.

The method is not limited by the nature of the target DNA employed to provide the folded target DNA, nor is the method limited by the manner in which the folded target DNA is generated. The method is also not limited by the nature of the bridging oligonucleotide probes; these probes may comprise DNA, RNA, PNA and combinations thereof as well as comprise modified nucleotides, universal bases, adducts, etc.

In a preferred embodiment, the method further comprises detecting the presence of the probe/folded target complex. When a detection step is employed either the bridging oligonucleotide probe or the target DNA (or both) may comprise a label (i.e., a detectable moiety); the invention is not limited by the nature of the label employed or the location of the label (i.e., 5' end, 3' end, internal to the DNA sequence). A wide variety of suitable labels are known to the art and include fluorescein, tetrachlorofluorescein, hexachlorofluorescein, Cy3, Cy5, digoxigenin, radioisotopes (e.g., $^{32}P$, $^{35}S$). In another preferred embodiment, the method further comprises quantitating the amount of probe/folded target complex formed. The method is not limited by the means used for quantification; when a labeled folded target DNA is employed (e.g., fluorescein or $^{32}P$), the art knows means for quantification (e.g., determination of the amount of fluorescence or radioactivity present in the probe/folded target complex).

Detection of the probe/folded target complex may also involve a catalyzed reaction on the probe that can only occur upon binding. It is contemplated that such catalyzed reaction may be mediated by an enzyme. By way of example, but not by way of limitation, the bound bridging oligonucleotide probe may be extended by a DNA polymerase, joined to another nucleic acid by the action of a ligase, or cleaved by a structure-specific nuclease. It is further contemplated that the catalytic action may be chemical, rather then enzymatic. For example, the cleavage of nucleic acid by compounds such as phenanthroline-Cu is specific for duplexed structures. It is contemplated that any chemical that can act upon nucleic acid in a manner that is responsive to the strandedness or other structural feature of the complex of the target may be used in the detection of the probe/folded target complex.

It is contemplated that any catalyzed reaction that is specifically operative on a duplex formed between a target nucleic acid and a substantially complementary probe may be configured to perform on the bridging probe/folded target complex.

In another embodiment the bound probe may participate in a reaction requiring a one or more additional nucleic acids, such as ligation reaction a polymerase chain reaction, a 5' nuclease reaction, (Lyamichev et al., Science 260: 778 [1993]; U.S. Pat. No. 5,422,253, herein incorporated by reference), or an Invader™ invasive cleavage reaction (PCT International Application No. PCT/US97/01072 [WO 97/27214]; co-pending Application Ser. Nos. 08/599,491, 08/682,853, 08/756,386, 08/759,038, and 08/823,516, all of which are herein incorporated by reference). In one embodiment, the additional nucleic acid includes another hybridized probe. In another embodiment, the additional nucleic acid included the target. In a preferred embodiment, the additional nucleic acid includes a bridging oligonucleotide probe complementary to two or more non-contiguous portions of the folded target.

It is contemplated that a nucleic acid on which the catalyzed reaction acts may be labeled. Thus detection of the complex on which the catalyzed reaction has acted may comprise detection of a labeled product or products of that reaction. The invention is not limited by the nature of the label used, including, but not limited to, labels which comprise a dye or a radionuclide (e.g., $^{32}P$), fluorescein moiety, a biotin moiety, luminogenic, fluorogenic, phosphorescent, or fluorophores in combination with moieties that can suppress emission by fluorescence resonance energy transfer (FRET). Numerous methods are available for the detection of nucleic acids containing any of the above-listed labels. For example, biotin-labeled oligonucleotide(s) may be detected using non-isotopic detection methods which employ streptavidin-alkaline phosphatase conjugates. Fluorescein-labeled oligonucleotide(s) may be detected using a fluorescein-imager. The oligonucleotides may be labeled with different labels. The different labels may be present on the probe before the catalytic reaction. In this embodiment the release of the labels from attachment to the same complex (e.g., by FRET analysis), may be used to detect formation of the probe/folded target complex. Alternatively, one or more of the labels may be added to the complex as a result of the catalytic reaction (e.g., by ligation to a labeled nucleic acid or by polymerization using labeled nucleoside triphosphates).

It is also contemplated that labeled oligonucleotides (reacted or unreacted) may be separated by means other than electrophoresis. For example, biotin-labeled oligonucleotides may be separated from nucleic acid present in the reaction mixture using para-magnetic or magnetic beads, or particles which are coated with avidin (or streptavidin). In this manner, the biotinylated oligonucleotide/avidin-magnetic bead complex can be physically separated from the other components in the mixture by exposing the complexes to a magnetic field. Additionally, the signal from the reacted oligonucleotides may be resolved from that of the unreacted oligonucleotides without physical separation. For example, a change in size as may be caused by binding to another oligonucleotide, or by cleavage, ligation or polymerase extension of at least one nucleic acid in the complex, will change the rate of rotation in solution, allowing of fluorescently labeled complexes or product molecules to be detected by fluorescence polarization analysis. However, it is not intended that the means of analysis be limited to those methods of cited above. Those skilled in the art of nucleic acid analysis will appreciate that there are numerous additional methods for the analysis of both of labeled and unlabeled nucleic acids that are readily adaptable for the detection of the probe/folded target complexes of the present invention.

In another preferred embodiment, the bridging oligonucleotide probe comprises a bridging oligonucleotide having a moiety that permits its capture by a solid support. The invention is not limited by the nature of the moiety employed to permit capture. Numerous suitable moieties are known to the art, including but not limited to, biotin, avidin and streptavidin. Further, it is known in the art that many small compounds, such as fluorescein and digoxigenin may serve as haptens for specific capture by appropriate antibodies. Protein conjugates may also be used to allow specific capture by antibodies.

In a preferred embodiment the detection of the presence of the probe/folded target complex comprises exposing the probe/folded target complex to a solid support under conditions such that the bridging oligonucleotide probe is captured by the solid support. As discussed in further detail below, numerous suitable solid supports are known to the art (e.g., beads, particles, dipsticks, wafers, chips, membranes or flat surfaces composed of agarose, nylon, plastics such as polystyrenes, glass or silicon) and may be employed in the present methods.

In a particularly preferred embodiment, the moiety comprises a biotin moiety and the solid support comprises a surface having a compound capable of binding to the biotin moiety, the compound selected from the group consisting of avidin and streptavidin.

In another embodiment, the folded target comprises a deoxyribonucleic acid sequence having a moiety that permits its capture by a solid support; as discussed above a number of suitable moieties are known and may be employed in the present method. In yet another embodiment, the detection of the presence of the probe/folded target complex comprises exposing the probe/folded target complex to a solid support under conditions such that the folded target is captured by the solid support. In a preferred embodiment, the moiety comprises a biotin moiety and the solid support comprises a surface having a compound capable of binding to the biotin moiety, the compound selected from the group consisting of avidin and streptavidin.

In a preferred embodiment, the bridging oligonucleotide probe is attached to a solid support; the probe is attached to the solid support in such a manner that the bridging oligonucleotide probe is available for hybridization with the folded target nucleic acid. The invention is not limited by the means employed to attach the bridging oligonucleotide probe to the solid support. The bridging oligonucleotide probe may be synthesized in situ on the solid support or the probe may be attached (post-synthesis) to the solid support via a moiety present on the bridging oligonucleotide probe (e.g., using a biotinylated probe and solid support comprising avidin or streptavidin). In another preferred embodiment, the folded target nucleic acid is attached to a solid support; this may be accomplished for example using a moiety present on the folded target (e.g., using a biotinylated target nucleic acid and solid support comprising avidin or streptavidin).

The present invention also provides methods for analyzing the structure of nucleic acid targets, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second bridging oligonucleotides, wherein the first bridging oligonucleotide is complementary to the first portion of the first and second folded targets and the second bridging oligonucleotide is complementary to the second portion of the first and second folded targets; and iv) a solid support comprising first, second, third and fourth testing zones, each zone capable of capturing and immobilizing the first and second bridging oligonucleotides: b) contacting the first folded target with the first bridging oligonucleotide under conditions such that the first bridging oligonucleotide binds to the first folded target to form a probe/folded target complex in a first mixture; c) contacting the first folded target with the second bridging oligonucleotide under conditions such that the second bridging oligonucleotide binds to the first folded target to form a probe/folded target complex in a second mixture; d) contacting the second folded target with the first bridging oligonucleotide to form a third mixture; e) contacting the second folded target with the second bridging oligonucleotide to form fourth mixture; and f) adding the first, second, third and fourth mixtures to the first, second, third and fourth testing zones of the solid support, respectively, under conditions such that the first and second bridging oligonucleotides are captured and immobilized.

The method is not limited by the nature of the first and second targets. The first and/or second target may comprise one or more non-contiguous regions, as well as one or more intervening regions. In preferred embodiments, the intervening regions comprise at least five nucleotides. The method is also not limited by the nature of the bridging oligonucleotide probes; these bridging oligonucleotide probes may comprise DNA, RNA, PNA and combinations thereof as well as comprise modified nucleotides, universal bases, adducts, etc. In some embodiments, the first and/or second bridging oligonucleotide probes comprise one or more intervening regions. In alternative embodiments, the intervening region of the bridging oligonucleotide probes comprises at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In a preferred embodiment, the first and second bridging oligonucleotide probes comprise DNA.

In alternative embodiments, the first bridging oligonucleotide in step d) does not substantially hybridize to the second folded target. In yet another embodiment, the hybridization of the first bridging oligonucleotide in step d) to the second folded target is reduced relative to the hybridization of the first bridging oligonucleotide in step c) to the first folded target. In further embodiments, the first and second targets comprise DNA, and/or the first and second bridging oligonucleotides comprise DNA.

The present invention also provides methods for analyzing folded nucleic acid targets, comprising: a) providing: i)

a first folded target having a nucleic acid sequence comprising first and second portions, wherein the first and second portions each comprise one or more double stranded regions and one or more single stranded regions; ii) a second folded target having a nucleic acid sequence comprising a first portion that is identical to the first portion of the first folded target, and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second bridging oligonucleotides, the first bridging oligonucleotide being complementary to the first portion of the first and second folded targets and second bridging oligonucleotide being complementary to the second portion of the first and second folded targets; and b) contacting the first and second folded targets with the solid support under conditions such that the first and second bridging oligonucleotides hybridize to the first folded target to form a probe/folded target complex.

In some embodiments, the contacting of step b) comprises adding the first folded target to the first testing zone and adding the second folded target to the second testing zone. In alternative embodiments, the first and second bridging oligonucleotides are immobilized in separate portions of the testing zones. In yet other embodiments, the first bridging oligonucleotide in the second testing zone does not substantially hybridize to the second folded target. In further embodiments, the first bridging oligonucleotide in the second testing zone hybridizes to the second folded target with a reduced efficiency compared to the hybridization of the first bridging oligonucleotide in first testing zone to the first folded target. The method is not limited by the nature of, nor the method of generating the first and second folded targets. The method is also not limited by the nature of, or the method of generating the oligonucleotide probes; these probes may comprise DNA, RNA, PNA and combinations thereof as well as comprise modified nucleotides, universal bases, adducts, etc. In some embodiments, the first and/or second folded target comprises one or more intervening region comprised of at least five nucleotides. In yet other embodiments, the first and/or second bridging oligonucleotide probe comprises one or more intervening regions comprised of at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. The invention is not limited by the nature of the solid support employed as discussed above. In some preferred embodiments of the method, the first and second folded targets comprise DNA. In alternative embodiments, the first and second folded targets comprise RNA. In yet other embodiments, the first and second bridging oligonucleotides comprise DNA.

The present invention provides methods for detection of structured nucleic acid targets, comprising the steps of: a) providing: i) a folded target having a nucleic acid sequence comprising one or more double stranded regions, and one or more single stranded regions, and further comprising two or more non-contiguous portions, and one or more intervening regions; ii) at least one bridging oligonucleotide probe capable of binding to two or more non-contiguous portions of said folded target; and iii) a reactant; b) mixing said folded target and said probe under conditions such that said probe hybridizes to said folded target to form a probe/folded target complex; and c) treating said probe/folded target complex with said reactant to produce at least one modified probe. In one embodiment the method further provides for the detection of said modified probe.

The present invention further provides a method, comprising: a) providing target nucleic acid comprising first and second non-contiguous single-stranded regions separated by an intervening region comprising a double-stranded portion; a bridging oligonucleotide capable of binding to said first and second non-contiguous single-stranded regions; and a reactant selected from the group consisting of polymerases and ligases; and mixing said target nucleic acid, said bridging oligonucleotide and said reactant under conditions such that said bridging oligonucleotide is modified to produce a modified oligonucleotide.

In some embodiments of the methods, the reactant is a polymerase, while in yet other embodiments, the modified oligonucleotide comprises an extended oligonucleotide. In still other embodiments, the reactant is a polymerase and the modified oligonucleotide comprises extended oligonucleotide. In yet other embodiments, the reactant is a ligase, while in yet other embodiments, the modified oligonucleotide comprises a ligated oligonucleotide. In still other embodiments, the reactant is a ligase and the modified oligonucleotide comprises a ligated oligonucleotide.

In yet other embodiments of the method, the bridging oligonucleotide is capable of binding to fewer than ten nucleotides of each of said first and second non-contiguous single-stranded regions. In still other embodiments, the bridging oligonucleotide is capable of binding to eight or fewer nucleotides of each of said first and second non-contiguous single-stranded regions.

In further embodiments of the method the target nucleic acid is DNA, while in some preferred embodiments, the DNA is viral DNA. In yet other preferred embodiments, the virus is selected from the group consisting of Parvoviridae, Papovaviridae, Adenoviridae, Hepadnaviridae, Herpesviridae, Iridoviridae, and Poxviridae. For example, it is intended that the present invention encompass methods for the detection of any DNA-containing virus, including, but not limited to parvoviruses, dependoviruses, papillomaviruses, polyomaviruses, mastadenoviruses, aviadenoviruses, hepadnaviruses, simplexviruses [such as herpes simplex virus 1 and 2], varicelloviruses, cytomegaloviruses, muromegaloviruses, lymphocryptoviruses, thetalymphocryptoviruses, rhadinoviruses, iridoviruses, ranaviruses, pisciniviruses, orthopoxviruses, parapoxviruses, avipoxviruses, capripoxviruses, leporipoxviruses, suipoxviruses, yatapoxviruses, and mulluscipoxvirus). Thus, it is not intended that the present invention be limited to any DNA virus family.

In further embodiments of the method the target nucleic acid is RNA, while in some preferred embodiments, the RNA is viral RNA. In yet other preferred embodiments, the virus is selected from the group consisting of Picornaviridae, Caliciviridae, Reoviridae, Togaviridae, Flaviviridae, Orlhomyxoviridae, Paramyxoviridae, Arenaviridae, Rhabdoviridae, Coronaviridae, Bunyaviridae, and Retroviridae. For example, it is intended that the present invention encompass methods for the detection of RNA-containing virus, including, but not limited to enteroviruses (e.g., polioviruses, Coxsackieviruses, echoviruses, enteroviruses, hepatitis A virus, encephalomyocarditis virus, mengovirus, rhinoviruses, and aphthoviruses), caliciviruses, reoviruses, orbiviruses, rotaviruses, birnaviruses, alphaviruses, rubiviruses, pestiviruses, flaviviruses (e.g., hepatitis C virus, yellow fever viruses, dengue, Japanese, Murray Valley, and St. Louis encephalitis viruses, West Nile fever virus, Kyanasur Forest disease virus, Omsk hemorrhagic fever virus, European and Far Eastern tick-borne encephalitis viruses, and louping ill virus), influenzaviruses (e.g, types A, B, and C), paramyxoviruses, morbilliviruses, pneumoviruses, veisculoviruses, lyssaviruses, filoviruses, coronaviruses, bunyaviruses, phleboviruses, nairoviruses, uukuvirugeg, hantaviruses, sarcoma and leukemia viruses, oncoviruses, HTLV, spumaviruses, lentiviruses, and arenaviruses).

The present invention also provides a method, comprising: a) providing target nucleic acid comprising first and second non-contiguous single-stranded regions separated by an intervening region comprising a double-stranded region; a bridging oligonucleotide capable of binding to said first and second non-contiguous single-stranded regions; a second oligonucleotide capable of binding to a portion of said first non-contiguous single-stranded region; and a cleavage means; b) mixing said target nucleic acid, said bridging oligonucleotide, said second oligonucleotide, and said cleavage means under conditions such that either said second oligonucleotide or said bridging oligonucleotide is cleaved.

In some preferred embodiments, the cleavage means comprises a nuclease. In other preferred embodiments, the cleavage means comprises a thermostable 5' nuelease. In still other preferred embodiments, the thermostable 5' nuclease comprises an altered polymerase derived from a native polymerases of Thermus species.

In other embodiments of the method, the conditions of mixing allow for hybridization of said bridging oligonucleotide and said second oligonucleotide to said target nucleic acid so as to define a region of overlap of said oligonucleotides. In some embodiments, the region of overlap comprises one base, while in other embodiments, the region of overlap comprises more than one base.

In further embodiments of the method the target nucleic acid is DNA, while in some preferred embodiments, the DNA is viral DNA. In yet other preferred embodiments, the virus is selected from the group consisting of Parvoviridae, Papovaviridae, Adenoviridae, Hepadnaviridae, Herpesviridae, Iridoviridae, and Poxviridae. For example, it is intended that the present invention encompass methods for the detection of any DNA-containing virus, including, but not limited to parvoviruses, dependoviruses, papillomaviruses, polyomaviruses, mastadenoviruses, aviadenoviruses, hepadnaviruses, simplexviruses [such as herpes simplex virus 1 and 2], varicelloviruses, cytomegaloviruses, muromegaloviruses, lymphocryptoviruses, thetalymphocryptoviruses, rhadinoviruses, iridoviruses, ranaviruses, pisciniviruses, orthopoxviruses, parapoxviruses, avipoxviruses, capripoxviruses, leporipoxviruses, suipoxviruses, yatapoxviruses, and mulluscipoxvirus). Thus, it is not intended that the present invention be limited to any DNA virus family.

In further embodiments of the method the target nucleic acid is RNA, while in some preferred embodiments, the RNA is viral RNA. In yet other preferred embodiments, the virus is selected from the group consisting of Picornaviridae, Caliciviridae, Reoviridae, Togaviridae, Flaviviridae, Orthomyxoviridae, Paramyxoviridae, Arenaviridae, Rhabdoviridae, Coronaviridae, Bunyaviridae, and Retroviridae. For example, it is intended that the present invention encompass methods for the detection of RNA-containing virus, including, but not limited to enteroviruses (e.g., polioviruses, Coxsackieviruses, echoviruses, enteroviruses, hepatitis A virus, encephalomyocarditis virus, mengovirus, rhinoviruses, and aphthoviruses), caliciviruses, reoviruses, orbiviruses, rotaviruses, birnaviruses, alphaviruses, rubiviruses, pestiviruses, flaviviruses ([e.g., hepatitis C virus, yellow fever viruses, dengue, Japanese, Murray Valley, and St. Louis encephalitis viruses, West Nile fever virus, Kyanasur Forest disease virus, Omsk hemorrhagic fever virus, European and Far Eastern tick-borne encephalitis viruses, and louping ill virus], influenzaviruses (e.g, types A, B, and C), paramyxoviruses, morbilliviruses, pneumoviruses, veisculoviruses, lyssaviruses, filoviruses, coronaviruses, bunyaviruses, phleboviruses, nairoviruses, uukuviruses, hantaviruses, sarcoma and leukemia viruses, oncoviruses, HTLV, spumaviruses, lentiviruses, and arenaviruses).

The present invention also provides a method, comprising: a) providing target nucleic acid comprising first and second non-contiguous single-stranded regions separated by an intervening region, said intervening region comprising a first double-stranded portion and a second double-stranded portion separated by a connecting single-stranded portion; and a bridging oligonucleotide capable of binding to said first and second non-contiguous single-stranded regions; and b) mixing said target nucleic acid and said bridging oligonucleotide under conditions such that said bridging oligonucleotide hybridizes to said target to form an oligonuclcetidc/target complex.

In further embodiments of the method the target nucleic acid is DNA, while in some preferred embodiments, the DNA is viral DNA. In yet other preferred embodiments, the virus is selected from the group consisting of Parvoviridae, Papovaviridae, Adenoviridae, Hepadnaviridae, Herpesviridae, Iridoviridae, and Poxviridae. For example, it is intended that the present invention encompass methods for the detection of any DNA-containing virus, including, but not limited to parvoviruses, dependoviruses, papillomaviruses, polyomaviruses, mastadenoviruses, aviadenoviruses, hepadnaviruses, simplexviruses [such as herpes simplex virus 1 and 2], varicelloviruses, cytomegaloviruses, muromegaloviruses, lymphocryptoviruses, thetalymphocryptoyiruses, rhadinoviruses, iridoviruses, ranaviruses, pisciniviruses, orthopoxviruses, parapoxviruses, avipoxviruses, capripoxviruses, leporipoxviruses, suipoxviruses, yatapoxviruses, and mulluscipoxvirus). Thus, it is not intended that the present invention be limited to any DNA virus family.

In further embodiments of the method the target nucleic acid is RNA, while in some preferred embodiments, the RNA is viral RNA. In yet other preferred embodiments, the virus is selected from the group consisting of Pieornaviridae, Caliciviridae, Reoviridae, Togaviridae, Flaviviridae, Orthomyxoviridae, Paramyxoviridae, Arenaviridae, Rhabdoviridae, Coronaviridae, Bunyaviridae, and Retroviridae. For example, it is intended that the present invention encompass methods for the detection of RNA-containing virus, including, but not limited to enteroviruses (e.g., polioviruses, Coxsackieviruses, echoviruses, enteroviruses, hepatitis A virus, encephalomyocarditis virus, mengovirus, rhinoviruses, and aphthoviruses), caliciviruses, reoviruses, orbiviruses, rotaviruses, birnaviruses, alphaviruses, rubiviruses, pestiviruses, flaviviruses (e.g., hepatitis C virus, yellow fever viruses, dengue, Japanese, Murray Valley, and St. Louis encephalitis viruses, West Nile fever virus, Kyanasur Forest disease virus, Omsk hemorrhagic fever virus, European and Far Eastern tick-borne encephalitis viruses, and louping ill virus), influenzaviruses (e.g, types A, B, and C), paramiyxoviruses, morbilliviruses, pneumoviruses, veisculoviruses, lyssaviruses, filoviruses, coronaviruses, bunyaviruses, phleboviruses, nairoviruses, uukuviruses, hantaviruses, sarcoma and leukemia viruses, oncoviruses, HTLV, spumaviruses, lentiviruses, and arenaviruses).

DESCRIPTION OF THE FIGURES

FIGS. 2A–2D provide a schematic of representation of a segment of the katg gene from *M. tuberculosis*. Depending on the sequence, the segment of the DNA can form the stem-loop structures depicted in 2C and 2D. The arrows in 2C and 2D show the sites that are cleaved when these structures are treated by the structure specific Cleavase® I nuclease. The black bar to the left of each structure indicates the region to which the katG probe would bind, with the pointed kink in the bar indicating a site of mismatch between the probe and the katG target. FIGS. 2A–2D show portions of SEQ ID NOS:1–4 (structures 2A–2D, respectively).

FIG. 3 shows at left a fluorescence imager scan of the cleavage patterns generated using the CFLP® method on the katG substrates. The letters above the lanes indicate that these DNA fragments contain to the corresponding structures diagrammed in FIG. 2. An arrow indicates the 37 nucleotide (nt) product of cleavage at the site indicated by the arrows in FIG. 2. The graph at the right depicts the fluorescence intensity measured when each of the molecules depicted in FIG. 2 was complexed to the katG capture probe and bound to a solid support in a structure probing assay.

FIG. 4 show a graph that depicts the fluorescence intensity measured when two variants of the katG target DNA with different amounts of flanking sequence were bound to a microtiter plate using a single capture probe.

FIG. 5 shows an analysis of several types of HCV by both the CFLP® method and by DNA sequencing. The sequence lanes were resolved beside the lanes showing the products of CFLP® cleavage. This allowed precise identification of the sites cleaved, and therefore the regions of structure, in the analysis of each of the HCV genotypes. The probes selected to interact in these regions are indicated to the right (SEQ ID NOS:11–19).

FIG. 6 provides an alignment of sequences that have been determined for the HCV genotypes examined in Example 3. The sites within the HCV targets which the probes have been designed to complement are underlined and shown in bold. The numbers of the probes are indicated above each site. SEQ ID NOS:20–23 are shown in FIG. 6.

FIG. 7 shows four graphs depicting the fluorescence signal measured after the solid support capture of the indicated HCV types by the indicated probes.

FIGS. 8A, B and C show graphs depicting the fluorescence signal measured after the solid support capture of the indicated HCV types by the indicated probes, at temperatures ranging from room temperature (approximately 22° C.) to 50° C.

FIGS. 9A–9D show graphs depicting the fluorescence signal measured after the solid support capture of different HCV types from clinical samples, by the indicated probes.

FIG. 10 shows schematic representations of the folded structures that would be assumed by each of the three test molecules, #80 (SEQ ID NO:39), #81 (SEQ ID NO:40) and #82 (SEQ ID NO:41).

FIGS. 11A and 11B show schematic representations of the capture oligonucleotides used in these studies. While are were tested with all three of the test molecules depicted in FIG. 10, for convenience they are shown aligned with their complementary regions in test molecule #80 (SEQ ID NO:39).

FIGS. 12A–12D show graphs depicting the fluorescence signal measured after the support capture of the three test molecules, #80 (SEQ ID NO:39), #81 (SEQ ID NO:40), and #82 (SEQ ID NO:41) by the indicated probes. The wider fourth panel (FIG. 12D), shows the fluorescence signal from each of the first three panels re-drawn together on a single scale of fluorescence intensity, for ease of comparison.

FIGS. 13A and 13B show graphs depicting the fluorescence signal measured after the solid support capture of the three test molecules, #80 (SEQ ID NO:39), #81 (SEQ ID NO:40), and #82 (SEQ ID NO:41) by the indicated probes. The names of the probes used in each capture test are indicated above each individual panel in these Figure panels.

FIG. 14 shows a schematic diagram of the process for selecting two segments of bridging oligonucleotide based on the data from the use of 5' and 3' nucleases to cleave a folded structure. Such cleavage reactions can be used to locate regions that are either upstream and downstream of folded structures, facilitating selection of complementary sequences to compose bridging oligonucleotides.

FIG. 15 shows an alignment of four 244 nt segments of HCV, representing types 1a, 1b, 2a/c and 3a. Type 1a is shown in its entirety, while only the differences are indicated for the other types. Cleavage sites generated by CFLP® cleavage are indicated by vertical lines along the sequence, with the weakest cleavage sites shown as broken lines.

FIGS. 16A and 16B show schematic diagrams of two possible secondary structures for a 244 nt fragment derived from HCV type 1a.

FIG. 17A shows an analysis by the CFLP® method of a 244 nt fragment derived from HCV type 1a and two 205 nt truncated fragments. The sizes of the significant cleavage bands are indicated to the right of the panel.

FIG. 17B shows schematic diagrams of two of the predicted structures for a region of the 244 nt amplicon derived from HCV type 1a. The CFLP® data indicates that the target DNA assumes multiple conformations in solution, each contributing to the cleavage pattern (Brow et al., supra).

FIG. 17C shows schematic diagram of three bridging oligonucleotides designed two interact with the predicted structures for this region (SEQ ID NOS:53, 64, and 65). The regions that are complementary as aligned to the target are indicated by a black line between the strands.

FIGS. 18A–D show schematic diagrams of the predicted structures for a region of the 244 nt amplicon derived from HCV types 1a, 1b, 2a/c and 3a, respectively. In 18 B–D the bases that differ from the type 1a sequence are shown in bold. Each is aligned with bridging oligonucleotides of six different designs (SED ID NOS:53, 54, 55, 56, 57, and 58). The regions that are complementary as aligned to the target are indicated by a black line between the strands. The 3' terminal contact sequence of each probe (excepting "c") is complementary to eight contiguous target bases upstream of the right most stem, but representation of the small central stem prevents showing this alignment.

FIG. 19 shows graphs depicting the fluorescence signal measured after the solid support capture of the amplicons derived from HCV types 1a, 1b, 2a/c and 3a by the indicated probes. The letters identifying the probes used in each capture test are indicated below each bar, and the signal in arbitrary fluorescence units is shown on the left of each panel.

FIG. 20A shows a schematic diagram of a structure in the amplicon derived from HCV type 1a aligned with non-bridging probes "a" and "e" and bridging probes "b"–"d". The regions that are complementary as aligned to the target are indicated by a black line between the stands.

FIG. 21 shows a fluorescence imager scan of the products of primer extension reactions using the probes depicted in FIG. 20A and the folded target strands derived from HCV types 1a, 1b, 2a/c and 3a, or using human genomic DNA as a control, as indicated above each lane. An arrow indicates the 170 nucleotide (nt) product of extension.

FIG. 26 shows a schematic diagram of an unstructured synthetic target (SEQ ID NO:63) aligned with non-bridging probes "a" and "e" and bridging probes "b"–"d" and ligation oligonucleotide "f" (SEQ ID NOS:52, 59, 53, 57, and 58, respectively). The regions that are complementary as aligned to the target are indicated by a black line between the strands.

FIGS. 29A and 29B shows a schematic diagram of either a structure in the amplicon derived from HCV type 1a, or an unstructured synthetic target (SEQ ID NO:63) respectively, aligned with non-bridging probes "a" and "e", bridging probes "b"–"d" and invasive cleavage probe "g" (SEQ ID NOS:52, 53, 57, 59, and 58, respectively). The regions that are complementary as aligned to the targets are indicated by a black line between the strands.

DEFINITIONS

Figure 1:
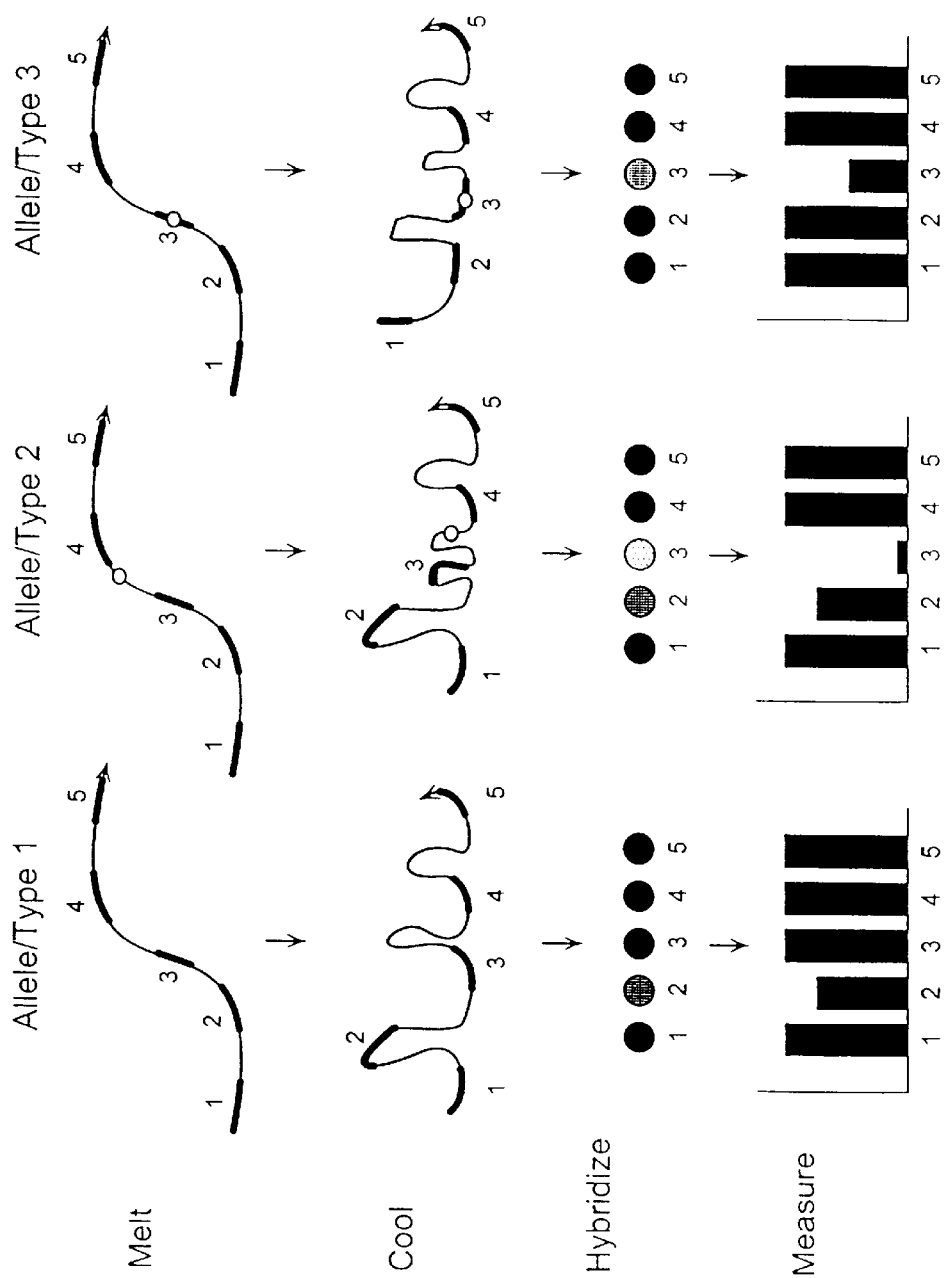
FIG. 1 provides a schematic of one embodiment of the detection methods of the present invention.

To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be the to have 5' and 3' ends.

When two different, non-oyerlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refer to the annealing of a complementary sequence to the target nucleic acid (the sequence to be detected) through base pairing interaction (Marmur and Lane, Proc. Natl. Acad. Sci. USA 46:453 [1960] and Doty et al., Proc. Natl. Acad. Sci. USA 46:461 [1960]). The terms "annealed" and "hybridized" are used interchangeably throughout, and are intended to encompass any specific and reproducible interaction between an oligonucleotide and a target nucleic acid, including binding of regions having only partial complementarity and binding interactions that make use of non-canonical interactions for stability and/or specificity.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "non-canonical" as used in reference to nucleic acids indicates interactions other than standard, or "Watson-Crick" base pairing, including but not limited to G-T and G-U base pairs, Hoogstein interactions, triplex structures, quadraplex aggregates, and multibase hydrogen bonding such as is observed within nucleic acid tertiary structures, such as those found in tRNAs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

The terms "signal probe" and "signal oligonucleotide," as used herein, are used interchangeably in reference to any oligonucleotide that is provided to permit detection of the progress or products of a reaction or interaction. A signal probe may be labeled or unlabeled, and may be modified or left unmodified by the mechanism of the reaction.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimety, gravimety, X-ray diffraction or absorption, magnetism, enzymatic activity, and the like.

The terms "target nucleic acid" and nucleic acid substrate" are used herein interchangeably and refer to a nucleic acid molecule which when denatured and allowed to renature (i.e., to fold upon itself by the formation of intra-strand hydrogen bonds), forms at least one folded structure. The nucleic acid target may comprise single- or double-stranded DNA or RNA.

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "substantially single-stranded" when used in reference to a nucleic acid target means that the target molecule exists primarily as a single strand of nucleic acid in contrast to a double-stranded target which exists as two strands of nucleic acid which are held together by inter-strand base pairing interactions.

Nucleic acids form secondary structures which depend on base-pairing for stability. When single strands of nucleic acids (single-stranded DNA, denatured double-stranded DNA or RNA) with different sequences, even closely related ones, are allowed to fold on themselves, they assume characteristic secondary structures. An alteration in the sequence of the target may cause the destruction of a duplex region(s), or an increase in stability of a thereby altering the accessibility of some regions to hybridization of the probes oligonucleotides. While not being limited to any particular theory, it is thought that individual molecules in the target population may each assume only one or a few of the structures (i.e., duplexed regions), but when the sample is analyzed as a whole, a composite pattern from the hybridization of the probes can be created. Many of the structures that can alter the binding of the probes are likely to be only a few base-pairs long and would appear to be unstable. Some of these structures may be displaced by the hybridization of a probe in that region; others may by stabilized by the hybridization of a probe nearby, such that the probe/substrate duplex can stack coaxially with the target intrastrand duplex, thereby increasing the stability of both. The formation or disruption of these structures in response to small sequence changes results in changes in the patterns of probe/target complex formation. Temperatures in the range of 20 to 55° C., with the range of 20 to 40° C. being particularly preferred, are suitable temperatures for the practice of the method of the invention.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene vary in sequence from one another A second mutant form of the structural gene may exist. This second mutant form varies in sequence from both the wild-type gene and the first mutant form of the gene. It is noted, however, that the invention does not require that a comparison be made between one or more forms of a gene to detect sequence variations. Because the method of the invention generates a characteristic and reproducible pattern of complex formation for a given nucleic acid target, a characteristic "fingerprint" may be obtained from any nucleic target without reference to a wild-type or other control. The invention contemplates the use of the method for both "fingerprinting" nucleic acids without reference to a control and identification of mutant forms of a target nucleic acid by comparison of the mutant form of the target with a wild-type or known mutant control.

The terms "structure probing signature," "hybridization signature" and "hybridization profile" are used interchangeably herein to indicate the measured level of complex formation between a folded target nucleic acid and a probe or set of probes, such measured levels being characteristic of the folded target nucleic acid when compared to levels of complex formation involving reference targets or probes.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATPF dGTP, dCTP and dTTP thus, the use of dUTP (a naturally occurring dNTP) in a PCR would comprise the use of a nucleotide analog in the PCR. A PCR product using dUTP, 7-deaza-dATP, 7-deaza-dGTP or any other nucleotide analog in the reaction mixture is the to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRS, RT-PCRs and the like. As noted above, an oligonucleotide primer need not be perfectly complementary to a target or template sequence. A primer need only have a sufficient interaction with the template that it can be extended by template-dependent synthesis.

The term "cleavage structure" as used herein, refers to a structure which is formed by the interaction of at least one probe oligonucleotide and a target nucleic acid to form at least one region of duplex, the resulting structure being cleavable by a cleavage means, including but not limited to an enzyme. The cleavage structure is a substrate for specific cleavage by the cleavage means, in contrast to a nucleic acid molecule which is a substrate for non-specific cleavage by agents such as phosphodiesterases which cleave nucleic acid molecules without regard to secondary structure (i.e., no formation of a duplexed structure is required).

The term "cleavage means" as used herein refers to any means which is capable of cleaving a cleavage structure, including but not limited to enzymes. The cleavage means may include native DNAPs having 5' nuclease activity (e.g., Taq DNA polymerase, *E. coli* DNA polymerase I) and, more specifically, modified DNAPs having 5' nuclease but lacking synthetic activity. The ability of 5' nucleases to cleave naturally occurring structures in nucleic acid templates (structure-specific cleavage) is useful to detect internal sequence differences in nucleic acids without prior knowledge of the specific sequence of the nucleic acid. In this manner, they are structure-specific enzymes. The cleavage means is not restricted to enzymes having solely 5' nuclease activity. The cleavage means may include nuclease activity provided from a variety of sources including the Cleavase® enzymes, the FEN-1 endonucleases (including RAD2 and XPG proteins), Taq DNA polymerase and *E. coli* DNA polymerase I. The cleavage means of the present invention cleave a nucleic acid molecule in response to the formation of cleavage structures; it is not necessary that the cleavage means cleave the cleavage structure at any particular location within the cleavage structure.

The term "structure-specific nucleases" or "structure-specific enzymes" refers to enzymes that recognize specific secondary structures in a nucleic molecule and cleave these structures without the regard to the specific sequences making up the structure.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule which contains a sequence which has at least partial complementarity with at least one probe oligonucleotide. The target nucleic acid may comprise single- or double-stranded DNA or RNA.

The term "probe oligonucleotide" refers to an oligonucleotide which interacts with a target nucleic acid to form a complex. The complex may also comprise a cleavage structure.

The term "non-target cleavage product" refers to a product of a cleavage reaction that is not derived from the target nucleic acid. In the methods of the present invention, cleavage of the cleavage structure may occur within the probe oligonucleotide. The fragments of the probe oligonucleotide generated by this target nucleic acid-dependent cleavage are "non-target cleavage products."

The term "invader oligonucleotide" refers to an oligonucleotide that hybridizes to a target nucleic acid such that its 3' end positions the site of structure-specific nuclease cleavage within an adjacently hybridized oligonucleotide probe. In one embodiment its 3' end has at least one nucleotide of sequence that is identical the first target-complementary nucleotide of the adjacent probe; these nucleotides will compete for hybridization to the same nucleotide in a complementary target nucleic acid. In another embodiment, the invader oligonucleotide has a single 3' mismatched nucleotide, and hybridizes to an adjacent, but not overlapping, site on the target nucleic acid.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or "multiple-drug resistant" refers to a microorganism which is resistant to more than one of the antibiotics or antimicrobial agents used in the treatment of the microorganism.

The term "non-contiguous," when used to describe regions within a target nucleic acid to be analyzed, is intended to mean that the regions are separated by intervening nucleic acid (or non-nucleic acid spacers). It is not intended that the present invention be limited by the size of the intervening nucleic acid (or the size of non-nucleic acid spacers). However, in preferred embodiments, the intervening sequence is at least five nucleotides in length.

The term "non-contiguous," when used to describe regions within a nucleic acid probe, means sequences capable of hybridizing to the non-contiguous regions of target nucleic acid. It is not intended that the present invention be limited to probes having intervening nucleic acid; that is to say, the non-contiguous regions of a probe are defined functionally, with reference to their binding to non-contiguous regions in a target, the target having intervening nucleic acid separating the non-contiguous regions. Nonetheless, the probes of the present invention may have (but need not have) intervening nucleic acid (or a non-nucleic acid spacer).

The terms "intervening nucleic acid," "intervening portion," "intervening region," "intervening nucleic acid sequence," and "intervening sequence," refer to nucleic acid (single-stranded or double-stranded), that separates two or more regions (e.g., non-contiguous regions) within a nucleic acid sequence. Where the present invention employs a probe having one or more intervening sequences, such intervening sequences are to be distinguished from mere single base mismatched nucleic acid, such that intervening sequences on the probe are at least two nucleic acids in length.

The term "bridging" when used in conjunction with a type of nucleic acid (e.g., oligonucleotide, probe, primer, etc.), refers to a nucleic acid that is made to contact non-contiguous sites on a folded target nucleic acid. For example, a bridging probe and a bridging primer may refer to oligonucleotides that hybridize across a structure for detection, or for subsequent primer extension, respectively, although "primer" and "probe" may also be used to indicate other types of interactions or reactions.

The term "non-bridging" when used in conjunction with a type of nucleic acid (e.g., oligonucleotide, probe, primer, etc.), refers to an nucleic acid that is not intended to hybridize across, a structure (i.e., it contains a region substantially complementary its hybridization partner nucleic acid).

The term "reactant" refers to any agent that can act upon either the target or non-target nucleic acids to create a detectable alteration from the original nucleic acid chemical or nucleotide composition.

The terms "catalyzed reaction" or "catalytic reaction" refers to any action on a nucleic acid that is catalyzed or enacted by a reactant other than the nucleic acid.

The terms "modified probe" and "modified oligonucleotide" refer to probes that have been altered from their original composition by the action of a reactant. Such alterations include but are not limited to cleavage as by a nuclease, elongation as by a polymerase, or joining to another entity, either through a covalent interaction, such as by ligation to another nucleic acid, or by chemical cross-linking to an entity such as a protein, a nucleic acid, a detectable moiety, or a solid support.

DESCRIPTION OF THE INVENTION

The methods of the present invention use the combined effects of mismatch and folded structure on hybridization to provide a tool for the detection of mutations and other polymorphisms in nucleic acids (e.g., DNA and RNA). The simultaneous probing of the primary (sequence), secondary (simple folded) and tertiary (interactions between secondary folds) structures of substrate molecules is referred herein simply as "structure probing." Rather than destroying secondary structures by high stringency conditions and target fragmentation, the methods of the present invention use conditions in which the formation of intramolecular structures is favored, i.e., unfragmented target strands in conditions of low stringency. Thus, the present method of probing is designed to detect variations between nucleic acids at any of these levels in a single assay.

At temperatures below the melting range of duplexed nucleic acid (i.e., below the melting temperature of long [i.e., >100 bp] nucleic acids; this is generally taken to be temperatures below about 85° C. for a nucleic acid of average G-C content), single-stranded nucleic acids undergo a complex process of intramolecular folding. The first rapid step of this process involves formation of short-range, or local stem-loops structures. Later in the folding process, formation of tertiary or global structure occurs as a result of interactions between different local domains (Zarrinkar and Williamson, Science 265:928 [1994] and Zarrinkar and Williamson, Nat. Struct. Biol., 3:432 [1996]). The effects of secondary structure of the target on probe binding is well documented for DNA and RNA molecules (Gamper et al., supra; Fedorova et al., FEBS Lett. 302:47 [1992]; Lima et al., Biochem., 31:12055 [1992]; Godard et al., Nucl. Acids Res., 22:4789 [1994]; Zarrinkar and Williamson, [1994], supra; Parkhurst and Parkhurst Biochem., 34:285 [1995]; and Schwille et al., Biochem., 35:10182 [1996]). Target sequences that form stable duplexes within intramolecular secondary structures can have probe binding constants $10^5$–$10^6$ times lower than sequences that exists as a single strands (Lima et al., supra). The reduction of the hybridization constant for structured regions is primarily due to a lower association rate constant rather than a higher dissociation rate constant (Lima et al., supra; Gamper et al., supra and Parkhurst and Parkhurst, supra), supporting the model that the structures in the target are blocking access of the probe to the complementary region within the target molecule.

Mutations in the target sequence change both local and global conformations of the molecule. It has been shown that the conformations assumed by single strands of nucleic acids can be probed using a structure-specific nuclease that cleaves in response to the structures that are formed in a number of test reaction conditions. (Brow et al., supra). Such cleavage creates a collection of product fragments that reflect those structures and which are characteristic of the particular strands. The structures that give rise to cleavage patterns are very sensitive to the precise nucleotide sequence of the strand, such that even single base differences in nucleic acids that are several hundred nucleotides long create sufficient changes in the folded conformations to be detectable in the resulting cleavage pattern (Brow et al., supra), and the changes in electrophoretic mobility in SSCP. As a result of these changes, some regions that were previously base paired may become unpaired and vice versa. By measuring probe hybridization rates it is possible to determine whether or not any region of a target molecule forms intramolecular structure. The examples below describe the use of multiple oligonucleotides to characterize DNA fragments (i.e., for structure probing). This approach is diagrammed schematically in FIG. 1.

In FIG. 1, three different, but related, target nucleic acids are analyzed using the structure probing assay of the present invention. Allele/Type 1 represents the prototypical target sequence (e.g., a wild type allele of gene X); Allele/Types 2 and 3 represent different alleles of the same target sequence (e.g., two different allelic variants of gene X). The thick regions labeled 1–5 along the three target nucleic acids represent the regions along the target that are complementary to probes 1–5. Allele/Type 2 contains a single-base variant (e.g., a point mutation) relative to Allele/Type 1 (represented by the small open circle between regions 3 and 4 of Allele/Type 2). This variant does not appear in a region where a probe binds to the Type 2 target; however, this variant alters the secondary structure of the Type 2 molecule relative to that of the Type 1 molecule such that region 3 of the Type 2 molecule is essentially unavailable for hybridization with probe 3. Allele/Type 3 also contains a single-base variant (e.g., a point mutation) relative to Allele/Type 1 (represented by the small open circle within region 3 of Allele/Type 3). The variant in this molecule is located within a probe binding region and reduces the efficiency with which probe 3 binds to the Type 3 molecule. The target nucleic acids are rendered substantially single-stranded (i.e., they are denatured, e.g., by heating) and then permitted to form secondary structures (e.g., by cooling) and then hybridized with probes 1–5. The probe/target complexes are captured onto a solid support and the amount of target that binds to each of probes 1–5 is determined for each target to generate a probe structure signature (also referred to as a hybridization signature or profile). The schematic shown in FIG. 1 is intended to illustrate that the signal variation may come from probe/target mismatch, or from the formation of local structures that block probe binding sites (i.e., regions on the target which are at least partially complementary to the probe). tertiary structure, involving interactions between sequences at some distance (even several hundred nucleotides) may also block binding, i.e., mutations at one site may influence probe binding hundreds of nucleotides away, as is seen with the katG targets employed in Example 1.

In the Examples below, the oligonucleotide probes include a biotin moiety so that the labeled target DNAs that have formed a hybridization complex with the probes can be captured by exposure to a solid support coated with streptavidin. When used for immobilization in this way, the probes are referred to herein as "capture probes." The labels on the DNA can then be detected, with the amount of captured DNA reflecting the efficiency of the probe/target hybridization, and thus the strength of a particular binding interaction.

In the Examples below, the solid support employed is a well of a 96-well microtiter plate. This format was chosen for convenience; the methods of the present invention are not limited to the use of microtiter plates or any particular support. The present invention contemplates the use of many types of solid supports, including but not limited to beads, particles, dipsticks, membranes and silicon or glass flat surfaces. It is also contemplated that the binding of the probe/target complexes to surfaces may be through interactions with the target nucleic acid (e.g., the use of biotinylated target nucleic acids), while a detectable label may be included on the probes.

In the embodiments presented herein, the affinity of the target nucleic acid (e.g., a DNA fragment of interest) for different probes is assessed by performing separate hybridization and solid support capture determinations for each probe sequence. It is envisioned that differently labeled probes, e.g., with different fluorescent dyes or other detectable moieties, may be used together in a single complex formation reaction. Use of an instrument that can detect several types of signal, such as a fluorimeter with the capacity to excite and detect at a variety of wavelengths, allows the signal contribution from each of the bound probes to be assessed.

In some typing applications, variants may have any one of several sequences (and therefore structures) and still be classed as the same type (e.g., in HCV, there are numerous sequence variants that are classed as type 1b). If it is not necessary to separately identify the subtypes within a type, a mixture of probes may be provided such that at least one type of probe will interact with each of the different known variants. If the target interacts appropriately (i.e., with the expected affinity) with any probe in the mixture it can be deduced to be of a broad type without concern about the identity of the particular subtype variant. In this way, genetic materials known to vary in sequence without affecting function or type (as do many rapidly changing pathogens) may be analyzed in a single assay without the need for a complex matrix of probes or for sequence determination.

In the following discussion, the oligonucleotide probes are discussed as capture probes. The use of this term is for convenience only, to avoid repetition of the enumeration of the possible configurations for this method, and it is intended that each of the embodiments described below may be used in combination with any of the probe/target configurations (e.g., labeled probes and captured target DNA and vice versa) described above.

The probes used in the methods of the present invention may be used without any prior analysis of the structure assumed by a target nucleic acid. In designing such an assay, one designs probes that would span the entire length of the target sequence, (i.e., they would be complementary to regions of the target that are substantially evenly spaced across the entire length of the target). Probes designed in this way may be phased to a variety of densities. For example, the probes may each shift in hybridization site by one or a few nucleotides, to give a very high resolution fingerprint of the target, or they may be designed to hybridize to adjacent but not overlapping regions, to give thorough coverage at a slightly lower resolution. Alternatively, they may be spaced at much larger intervals for a lower resolution screen. The choice of spacing will be dependent on the needs of the assay. A higher density fingerprint will have a greater likelihood of identifying any possible polymorphism, and may be more suitable for situations where certainty in identification of single base changes is required (e.g., identification of mutations associated with cancers and other diseases). When genotyping is to be performed on targets in which more variation is expected (e.g., rapidly changing viruses), a lower density array may be sufficient for accurate identification. The examples below provide such an analysis for the identification of Hepatitis C viral types. For any given case, it can be determined empirically using appropriately selected reference target molecule whether a chosen probe or array of probes can distinguish between genetic variants sufficiently for the needs of a particular assay. Once a probe or array of probes is selected, the analysis of which probes bind to a target, and how efficiently these probes bind (i.e., how much of probe/target complex can be detected) allows a hybridization signature of the conformation of the target to be created. One possible format for such a signature is as a graph of the measured amounts of a complex formed between the target and each probe, as shown in FIGS. 4, 7, 8, and 9. It is not intended that the structure probing or hybridization signature be limited to the use of the column graphs shown in these figures. It is contemplated that the signature may be stored, represented or analyzed by any of the methods commonly used for the presentation of mathematical and physical information, including but not limited to line, pie, or area graphs or 3-dimensional topographic representations. The data may also be used as a numerical matrix, or any other format that may be analyzed either visually, mathematically or by computer-assisted algorithms.

The resulting signatures of the nucleic acid structures serve as sequence-specific identifiers of the particular molecule, without requiring the determination of the actual nucleotide sequence. While specific sequences may be identified by comparison of their signature to a reference signature, the use of algorithms to deduce the actual sequence of a molecule by sequence-specific hybridization (i.e., at high stringency to eliminate the influence of secondary and tertiary structures) to a complete matrix (i.e., probes that shift by a single nucleotide position at each location of an array), is not a feature or requirement, or within the bounds of the methods of the present invention.

It is contemplated that information on the structures assumed by a target nucleic acid may be used in the design of the probes, such that regions that are known or suspected to be involved in folding may be chosen as hybridization sites. Such an approach will reduce the number of probes that are likely to be needed to distinguish between targets of interest.

There are many methods used to obtain structural information involving nucleic acids, including the use of chemicals that are sensitive to the nucleic acid structure, such as phenanthroline/copper, EDTA-$Fe^{2+}$, cisplatin, ethylnitrosourea, dimethyl pyrocarbonate, hydrazine, dimethyl sulfate, and bisulfite. Such chemical reagents may cause cleavage based on structure, or they may cause nucleotide modification that can subsequently be detected, such as by pausing or blocking of reverse transcriptase or other DNA polymerase copying, or by fingerprinting or other chromatography methods. Those skilled in the art are familiar with numerous additional methods for the detection of nucleotide modifications within a nucleic acid strand.

Enzymatic probing can be done using structure-specific nucleases from a variety of sources. Duplex-specific nucleases such as cobra venom $V_1$ nuclease have been widely used in the analysis of RNA structures (See e.g., Lowman and Draper, J. Biol. Chem., 261:5396 [1986]). In addition, suitable 5' nucleases include the Cleavase® enzymes (Third Wave Technologies, Inc., Madison, Wiss.), Taq DNA polymerase, *E. coli* DNA polymerase I, and eukaryotic structure-specific endonucleases (e.g., human, murine and Xenopus XPG enzymes, yeast RAD2 enzymes), murine FEN-1 endonucleases (Harrington and Lieber, Genes and Develop., 3:1344 [1994]) and calf thymus 5' to 3' exonuclease (Murante et al., J. Biol. Chem., 269:1191 [1994]). In addition, enzymes having 3' nuclease activity such as members of the family of DNA repair endonucleases (eg., the RrpI enzyme from *Drosophila melanogaster*, the yeast RAD1/RAD10 complex and *E. coli* Exo III), are also suitable for examining the structures of nucleic acids. In Example 3, the use of the CFLP® method for identifying regions of folding in PCR amplified segments of the HCV genome is described.

If analysis of structure as a step in probe selection is to be used for a segment of nucleic acid for which no information is available concerning regions likely to form secondary structures, the sites of structure-induced modification or cleavage must be identified. It is most convenient if the modification or cleavage can be done under partially reactive conditions (i.e., such that in the population of molecules in a test sample, each individual will receive only one or a few cuts or modifications). When the sample is analyzed as a whole, each reactive site should be represented, and all the sites may be thus identified. Using a CFLP® cleavage reaction as an example, when the partial cleavage products of an end labeled nucleic acid fragment are resolved by size (e.g., by electrophoresis), the result is a ladder of bands indicating the site of each cleavage, measured from the labeled end. Similar analysis can be done for chemical modifications that block DNA synthesis; extension of a primer on molecules that have been partially modified will yield a nested set of termination products. Determining the sites of cleavage/modification may be done with some degree of accuracy by comparing the products to size markers (e.g., commercially available fragments of DNA for size comparison) but a more accurate measure is to create a DNA sequencing ladder for the same segment of nucleic acid to resolve alongside the test sample. This allows rapid identification of the precise site of cleavage or modification.

Two approaches have commonly been applied to elucidate nucleic acid secondary structures: physical approaches, such as analysis of crystal structure or NMR, and analytical approaches, such as comparative or phylogenetic analysis. Physical analysis remains the only way to get a complete determination of a folded structure for any given nucleic acid. However, that level of analysis is impractical if the goal is to analyze a large number of molecules. By far, the most often used method of analyzing biological nucleic acids is a phylogenetic, or comparative approach. This method of analysis is based on the biological paradigm that functionally homologous sequences will adopt similar structures. Sequences are screened for sequence conservation, stem-loop conservation, and for compensatory sequence changes that preserve predicted structures. Unfortunately, such analysis can only be applied when the number of related sequences is large enough for statistical analysis.

The efficient analysis of single nucleic acids requires the use of multiple tools. Many of the available tools can give partial information on the possible structures assumed by a given molecule. As stated above, these methods include enzymatic analysis, chemical structure probing, and computer based analysis of regions of base pairing. In addition, deletion studies, in which portions of a linear molecule are deleted and the effects on the folding are analyzed by the above-cited methods, can help identify with more certainty those regions of a nucleic acid that interact with each other. None of these methods in isolation can provide sufficient physical information to identify with certainty any non-contiguous regions that will be in close enough proximity to be simultaneously contacted by a bridging oligonucleotide. For example, one of the most commonly used nucleic acid folding programs, "mfold" (Zuker, Science 244:48 [1989]; Jaeger et al., Proc. Natl. Acad. Sci. USA, 86:7706 [1989]; Jaeger et al., Meth. Enzymol. 183:281 [1990]) uses previously determined physical measurements for the effects of various secondary structure features, such as basepair combinations, loops, bulges, etc., on the stability of folded structures to predict structures that have the lowest possible free energy. This approach is referred to as an energy minimization approach (See, Gaspin and Westhof, J. Mol. Biol. 254:163 [1995] for review). While mfold and other computer-based folding algorithms can be made to present only those structures that are most likely to form (e.g., that are thermodynamically favored), when the software is permitted to show structures that are even slightly less energetically favorable, there are usually dozens of such structures predicted for any given nucleic acid strand. Even though these structures may be very stable, and may in fact be proven to exist in nature, they are referred to as "suboptimal" structures, because they are calculated to have a less favorable free energy based on the software parameters. Using information derived from the other methods (e.g., analyzing folded structures or by physical methods), allows the number of structures to be pared down dramatically, from many, many possible structures, to a few probable ones.

One additional software-based approach involves tallying the number of pairing partners available for each base within a collection of suboptimal structures predicted for a given nucleic acid strand (Zuker and Jacobson. Nucl. Acids Res. 23:2791 [1995]). The pairing number, or "p-num" for each base gives a quantitative measure of the fidelity of pairing, i.e., the number of possible pairing partners of each base position. It has been observed that predicted structures containing bases with p-nums that are lower than those of surrounding regions have a stronger correlation with structures that have been verified by physical or phylogenetic conservation data. Therefore using mfold and p-num together can help simplify the task of identifying structures that may be assumed by a nucleic acid strand. Both p-num and mfold are available commercially (Genetics Computer Group, Madison, Wisc.).

A significant limitation of the energy minimization programs for nucleic acids folding is that all of them, including mfold, use greatly simplified thermodynamic models that include energy parameters that are not well defined. The result is that the predicted optimal structures may not correspond to the actual conformation of the nucleic acid in solution. A partial solution to this is to extend the number of computed structures to include those that have suboptimal energies, thereby increasing the chances that one of them has better correlation with a real one. This step may produce an large number of possible structures, and identification of actual structures may be difficult without other analytical tools. For example, the mfold predictions done for the HCV type 1a amplicon, as described in Example 8, resulted in 32 predicted structures.

Efficient screening of the suboptimal structures can be accomplished by incorporating constraints derived from experimental data or phylogenetic analysis into the computer algorithm. The use of structure specific nucleases having well characterized specificity have an advantage that the site of cleavage can convey additional information based on the structural requirements for cleavage. This is illustrated here by discussion of information potentially gained by cleavage with a 5' nuclease, Cleavase® I nuclease, but the same deductive approach is equally applicable and useful for other structure-specific cleavage agents for which a substrate structure is well defined (i.e., it is known where in the structure the cleavage can occur). The specificity of Cleavase® enzymes is such that cleavage occurs at the 5' ends of hairpin duplexes, after the first base pair (Lyamichev et al., supra). This means that any cleavage site identifies both a base that must be paired in the structure, and that the base to which it pairs must be downstream in the strand. This can expressed as follows: if there is a cleavage site at position i, then nucleotide i is base paired with nucleotide j where j>i. This allows the use of existing constraint parameters without modification of the folding algorithm to predict only those structures that correlate with the cleavage data. If cleavage occurs at position i, then a series of structures can be calculated to explain it using the following constraints, 'f i 0 1' (nucleotide i is forced to be base paired) and 'p 1 0 i-1' (prohibiting nucleotides from 1 to i-1 to be base paired). For example, to generate structures that could be responsible for a major cleavage site at position 90 of HCV1a DNA, folding of 244 nt DNA fragment of HCV1a (FIG. 15) was done using mfold version 2.3 (http://www.ibc.wustl.edu/~zuker) with constraints 'f 90 0 1' and 'p 1 0 89' predicting structure shown in FIG. 16A. It is important that this structure not only predicts a cleavage site at position 90, but also explains cleavages at positions 102–103, 161 and 173, making it a good candidate to represent actual base pairing in the DNA molecule. The structure shown in FIG. 16A does not explain cleavage sites at positions 118–119 and 173. To reveal corresponding structures, the folding was done using constraints 'f 118 0 1' and 'p 1 0 117' (nucleotides 1–117 are not base paired and nucleotide 118 is base paired) with one of resulting structures shown in FIG. 16B. Again this structure not only reasonably predicts cleavage site at position 117–118 but also shows how cleavage at position 123 may happen. The same two structures were identified in the development of the experiments described in Example 8, using manual comparison of the cleavage sites and the 32 suboptimal folds. By either method, the knowledge of the structure specificity of the 5' nuclease made it possible to eliminate from consideration, all predicted structures that would require the cleavage sites to vary from the known substrate structure. This reduced the field of possible structures from 32 to 2. Use of additional enzymes, such as 3' nucleases, or duplex specific chemical agents, that can identify other positions that must be base-paired within a structure can further narrow the field.

In addition to the structural mapping methods described above, there are several methods based on the actions of polymerizing enzymes that may be used to gain structural information. It has long been observed that reverse transcriptases can have difficulty polymerizing through RNA secondary structures. For this reason, reverse transcriptases that can be used at high temperatures have been sought (Myers et al., Biochem., 30:7661 [1991]), in order to facilitate full-length reverse transcription before cloning or PCR amplification. By intentionally using polymerases that produce such pausing effects, structures formed in a template strand may be mapped by the location of the pause sites (e.g., by extension of a labeled primer).

Another approach based on the use of DNA polymerases takes advantage of the observation that some DNA polymerases, upon encountering a fold in the template strand, will apparently polymerize across a structure by a mechanism that has been termed "strand switching," thereby deleting the complement of the structured intermediate sequence. Though an understanding of the mechanism of strand switching is not necessary in order to practice the present invention, it is believed that strand switching involves some degree of displacement synthesis, such that a small portion of a sequence (even to the level of one base), is duplicated, followed by a branch migration that pairs the 3' end of the elongated strand with sequences on the far side of the template structure (Patel et al, Proc. Natl. Acad. Sci. USA 93:2969 [1996]). This mechanism can conceivably be used for structure mapping in at least two ways. For example, if the 3' side of a structure has been mapped using a 3' nuclease in a CFLP® reaction, as discussed above, a primer may be designed such that the 3' end of the primer is poised to polymerize either along or across the structure-forming region. In addition to its template complementary sequence, the primer may be supplied with one or a few degenerate nucleotides (e.g., two or more nucleotides at the same position on different copies of the primer) on the 3' end, to provide opportunity for strand switching, regardless of the downstream sequence. The primer may then be extended under conditions favoring strand switching (Patel et al., supra). The isolation (e.g., by cloning and sequencing) of such sites should identify the sequences that are coming together to form the folded structures, thus facilitating bridge oligonucleotide design. A second approach is similar, but without the use of primers adjacent to any particular putative structure. In this embodiment, a strand to be analyzed is primed using a normal primer, and synthesis is carried out in the same or similar strand switch favoring conditions. The use of conditions that favor base misincorporation (e.g., by the use of manganese in the synthesis reactions), and therefore promote pausing of the polymerase, would provide additional opportunity for branch migration and strand switching. The analysis of the junction sites would then follow as with the first approach. By these methods, both sides of a cleavage structure could be identified. It is also expected that alternative pairing partners for various sequences would be represented in the collection of molecules created.

To distinguish between related nucleic acids, the regions that show different sites of cleavage or modification have the highest probability of having secondary structures that will respond differently to probes in the methods of the present invention. This is for two reasons. First, the cleavage or modification is physical evidence that a structure may form at a given site under the conditions of the cleavage or modification assay. Second, the structures that are detected by the CFLP® method have been found to be predominantly local (i.e., formed from sequences that are close to each other along the nucleic acid strand, Brow et al., supra), so that changes observed are likely to be caused by base changes near the altered cleavage site. By designing oligonucleotide probes to hybridize or complex with the regions showing different sites of cleavage or modification there is a higher probability of finding either a base change (primary structure variation) or a folding change (secondary structure variation) that will affect the complexing of the probe to that site, thus facilitating the distinction between the comparison targets. Because of the complex nature of the folded structure formation as described above and because any given probe may interact with the target in a number of ways, choosing a probe in this way is not a guarantee that any particular probe will provide a diagnostic distinction. This is offered as a guide to increase the probability that it will. When working with an uncharacterized target or set of targets, the use of a multiplicity of such probes will give the most distinctive signature of probe/target complex formation.

In one embodiment, it is preferred that the probes used in the methods of the present invention be short enough to provide distinctive hybridization signatures for variants of a target. Probes longer than about 20 nt (e.g., 20 to 40 nt) can interact with target nucleic acids in a specific manner at elevated temperatures (e.g., higher than about 40° C.) and thus are suitable for use in the present methods. However, probes in this size range may interact with multiple sites on the target if the reaction is performed below about 40° C., reducing the distinction between variants. If this is the case, higher reaction temperatures or more stringent solution conditions (e.g., lower salt, the inclusion of helix-destabilizing agents such as dimethyl sulfoxide or formamide) may prove useful in enhancing the distinction between targets. In a particularly preferred embodiment, the method of the present invention is performed at ambient temperatures (e.g., 20 to 25° C.). When the assay is performed at room temperature, small probes with $T_m$s of 40°

C. or less (e.g., 10 to 20 nt) can provide the discrimination necessary, as shown in the examples below. Probes in this size range are also less likely to fold on themselves under the reaction conditions, an effect that would reduce the binding efficacy of a probe without regard to the structure of the target.

As stated above, the capture probe may interact with the target in any number of ways. For example, in another embodiment, the capture probes may contact more than one region of the target nucleic acid. When the target nucleic acid is folded as described, two or more of the regions that remain single stranded may be sufficiently proximal to allow contact with a single capture probe. The capture oligonucleotide in such a configuration is referred to herein as a "bridge" or "bridging" oligonucleotide, to reflect the fact that it may interact with distal regions within the target nucleic acid. The use of the terms "bridge" and "bridging" is not intended to limit these distal interactions to any particular type of interaction. It is contemplated that these interactions may include non-canonical nucleic acid interactions known in the art, such as G-T base pairs, Hoogstein interactions, triplex structures, quadraplex aggregates, and the multibase hydrogen bonding such as is observed within nucleic acid tertiary structures, such as those found in tRNAs. The terms are also not intended to indicate any particular spatial orientation of the regions of interaction on the target strand, i.e., it is not intended that the order of the contact regions in a bridge oligonucleotide be required to be in the same sequential order as the corresponding contact regions in the target strand. The order may be inverted or otherwise shuffled.

It is known that synthetic oligonucleotides can be hybridized to non-contiguous sequences in both RNA and DNA strands, in a manner that either causes the intervening sequence to loop out, or that bridges the base of an internal folded structure (Richardson et al., J. Am. Chem. Soc., 113:5109 [1991]; Francois et al., Nucl. Acid. Res., 22: 3943 [1994]). However, these references do not suggest the design or use of bridging oligonucleotides that can distinguish between the different folded structures, or that bind with significantly reduced efficiency when the intervening sequence is unstructured. The present invention provides methods for the use and design of bridge capture probes with minimally stable regions of complementarity to make these bridge probes sensitive to changes in the target strand structure. Minimal stability (i.e., with a very low melting temperature), may be created in a number of ways, including by the use of short lengths of complementarity, low G-C basepair content, and/or the use of base analogs or mismatches to reduce the melting temperature. To test the effects of variations in the target structure on the efficiency of capture with different lengths of bridge probes, three test molecules were created; these are shown in schematic representation in FIG. 10. Test molecule #80 (SEQ ID NO:39) has a long segment of self complementarity and when folded as shown, the 8 basepair hairpin formed by this oligonucleotide is further stabilized by a "tri-loop" sequence in the loop end (i.e., three nucleotideg form the loop portion of the hairpin) (Hiraro et al., Nucleic Acids Res. 22(4):576 [1994]). In test molecule #81 (SEQ ID NO:40), the stem is interrupted by 2 mismatches to form a less stable structure, and the region of self-complementarity is entirely removed in test molecule #82 (SEQ ID NO:41). All three of these molecules have identical target regions for the binding of the capture oligonucleotides, and an examination of their use is described in Example 6.

When a bridging oligonucleotide contacts sequences on either side of a basepaired stem, the structure formed is termed a three-way or three-arm junction. Such junctions have been studied extensively to determine their physical structure and to assess the differences that occur in the physical structure when additional nucleotides are included in these structures. When extra nucleotides are included at the junction site, where the three strands come together (i.e., when a 'bulged' structure is formed), it has been shown that the structure is more flexible and that some degree of coaxial stacking between the arms stabilized the structure compared to the unbulged structure (See e.g., Zhong et al., Biochem., 32:6898 [1993]; and Yang et al, Biochem., 35:7959 [1996]). The inclusion of two thymidine nucleotides in the portion of the probe that forms the junction is particularly preferred.

There are a number of approaches that may be used in the design or selection of bridging capture probes. As noted above, the term "capture probes" is not intended to limit the application of the bridging probes of the present invention to the capture of a target strand onto a solid support. Additional applications of the bridging probes are described in the Experimental Examples, below. Furthermore, for simplicity of discussion and to avoid repetition, this section describes one embodiment of the present invention, namely a process for creating bridge oligonucleotides that interact with only two regions of a target nucleic acid. It is not intended, however, that the invention be limited to the use of oligonucleotides that have only two sites of interaction. It is contemplated that bridge oligonucleotides may be created that can interact with many sites on a folded target molecule.

Bridge oligonucleotides may be created by the joining two or more short oligonucleotide sequences. The creation of bridge oligonucleotides may be based upon observations that these sequences have been determined to interact with a given folded target when used in isolation, without limitation to any particular nature of interaction, or they may be deduced to be capable of such interaction by virtue of sequence composition, complementarity, or like analysis. For convenience, such sequences are termed herein "contact sequences," to reflect the putative ability of such a sequence to contact the target molecule. The designation of a particular sequence as a contact sequence is not intended to imply that the sequence is in contact, or is required to contact a target in any particular embodiment.

In alternative embodiments, contact sequences may be joined by synthesizing or otherwise creating a new oligonucleotide that incorporates both sequences into a single molecule. In one embodiment, the sequences are joined contiguously within the bridge oligonucleotide (i.e., without any intervening nucleotides or other space-filling material). In another embodiment, the contact sequences are non-contiguous, with the spacing provided by additional nucleotides. In a preferred embodiment, the contact sequences are bridged by two thymidine nucleotides, as depicted in several of the bridging probes in FIG. 11A. In another preferred embodiment, the contact sequences in the bridging oligonucleotide are connected by a segment of nucleic acid containing a region of self-complementarity, such that the bridging oligonucleotide itself contains a folded structure. A stem-loop folded structure within the bridge oligonucleotide, if situated opposite a stem in the target nucleic acid, would permit the formation of a four-way Holliday structure, which is stabilized by coaxial stacking of the arms (Duckett et al., Cell 55:79 [1988]).

Alternatively, the bridge oligonucleotide may be created by linking the individual sequences with non-nucleotide spacers such as those commonly known in the art, such as d-spacers (Glen Research Corp. (Sterling, Va.), or other chemical chains, such as polyethers (Cload and Shephartz, J. Am. Chem. Soc., 113:6324 [1991]).

Contact sequences may also be linked to form the bridge probes post synthetically, by enzymatic (e.g., ligation) or by chemical interaction to produce either covalent (e.g., cross-linked) or non-covalent bonds (e.g., affinity bonds such as formed in an antigen-antibody interaction).

The formation of the complexes between the probes and the targets may be performed using a wide variety of solution conditions. Conditions considered to be "low stringency" have been well defined in the areas of hybridization to filters and membranes (Sambrook et al, *Molecular Cloning: A Laboratory Manual*, 2nd ed. Cold Spring Harbor Laboratory Press, Cold Spring Harbor, N.Y. [1989]) and to other solid supports, such as silicon or glass wafers, chips or slides (Maskos and Southern, Nucl. Acids Res., 20:1675 [1992]). It is contemplated that the formation of the complexes may be done in solution, before the binding of either the target or the probe to a solid support, or it may be done after one of the molecules has been bound to the support. It is recognized, and considered to be within the scope of the invention, that the kinetics and mechanics of complex formation may differ depending on whether complex formation is performed in solution or on a solid support. The identity of the support would also be expected to influence the complex formation. However, as long as complexes can be made to form at detectable levels, a set of conditions is considered appropriate for use in the present methods.

It is further contemplated that the complexes may be formed on nucleic acids that have not been isolated from a sample source, such as in live cells (in vivo) or in tissue samples (in situ). It is also contemplated that a nucleic acid found within a cell may be native to that cell, or may be transferred into the cell (e.g., by viral infection, by laboratory-induced transfection, or by in vivo transcription from an introduced nucleic acid). The methods of the present invention as applied to nucleic acids within cells are not limited to nucleic acids of any particular origin or cell type.

A number of solid supports known in the art are contemplated for use with the methods of the present invention. In the examples below, a 96-well microtiter plate is used as a support medium. The method may also be applied to other supports nucleic acid commonly used for nucleic acid analyses, including but not limited to beads, particles, membranes, filters, dipsticks, slides, plates and microchips. Such supports may be composed of a number of materials known to be compatible with nucleic acids analyses, including but not limited to agarose, styrene, nylon, glass and silicon.

Individual complex formation (i.e., assessing a single target with a single probe) may be sufficiently informative for some applications. In other applications, it may be desirable to use a number of probes against a single target. For a large number of probes, it may be useful to use an array format, in which a large number of probes are bound to a surface in an ordered pattern. Means for creating such arrays on surfaces such as glass slides and microchips are known in the art (Southern et al., Genomics 13:1008 [1992]; Chee et al., Science 274:610 [1996]; and Foder et al., Science 251:767 [1991]; and U.S. Pat. No. 5,436,327 to Southern et al., U.S. Pat. No. 5,429,807 to Matson et al. and U.S. Pat. No. 5,599,695 to Pease et al., all of which are herein incorporated by reference).

A. Use of Bridging Oligonucleotides in Catalyzed Reactions

As discussed above, it is contemplated that any catalyzed reaction that is specifically operative on a duplex formed between a target nucleic acid and a substantially complementary probe may be configured to perform on the bridging probe/folded target complex. Examples demonstrating the use of bridging probes in primer extension, ligation and structure-specific nuclease cleavage are provided below. Primer extension reactions and ligation reactions are well known in the art and the basic method for performing these reaction are published (See e.g., Sambrook et al., supra), as well as often being provided by the manufactures of the enzymes. The Invader™ invasive cleavage reaction is based on the use of a structure-specific nuclease that is used to cleave oligonucleotide probes once they hybridize to a target nucleic acid. The nature of the reaction allows the cleavage of many copies of the probe oligonucleotide for each copy of the target nucleic acid. Complete descriptions of the technology and its variables are included in PCT International Application No. PCT/US97/01072 (WO 97/27214) and co-pending Application Ser. Nos. 08/599,491, 08/682, 853, 08/756,386, 08/759,038, and 08/823,516, all of which are herein incorporated by reference. Briefly, The Invader™ assay is a method for detecting a specific target sequence within a nucleic acid mixture. The assay depends on the coordinate actions of at least two synthetic oligonueleotides, together constituting a probe system, and a structure-specific nuclease. The oligonucleotides of the probe system may be referred to as the signal oligonucleotide and the Invader™ oligonucleotide. By the extent of their substantial complementarity to the target strand, each of these oligonucleotides defines a specific region of the target strand. These regions must be oriented such that when the probe system is hybridized to the target strand, the Invader™ oligonucleotide is upstream of the signal oligonucleotide and such that the Invader™ oligonucleotide sequence either overlaps with the probe oligonucleotide sequence by at least one nucleotide (i.e., the two regions of the target nucleic acid defined by the oligonucleotides of the probe system share at least one nucleotide), or, when there is no overlap, the two target regions defined by the oligonucleotides must abut, and the 3' terminus of the Invader™ oligonucleotide must have a single additional nucleotide that is not complementary to the target strand at that site.

The nuclease recognizes the structure formed by hybridization of the probe system to the specific target nucleic acid and cleaves the signal oligonucleotide, the precise site of cleavage being dependent on the amount of its overlap with the Invader™ oligonucleotide. If the reaction is run such that the structure can partially disassemble to allow cleaved signal oligonucleotide to be replaced by intact signal oligonucleotide (e.g., performed at an elevated temperature to promote rapid dissociation and association of signal probes), then multiple probes may be cleaved for each copy of the target nucleic acid, the amount of target present then being calculable from the rate of product accumulation and the time of incubation.

The nucleases of the Invader™ assay include any nuclease capable of specifically recognizing the structure defined above, and cleaving within the signal oligonucleotide, thereby creating cleavage products. Such nucleases include, but are not limited to the 5' nucleases associated with eubacterial DNA polymerases, and the DNA repair-associated nucleases of the FEN1, RAD2 and XPG classes.

The oligonucleotides of the invader probe system may comprise DNA, RNA, PNA and combinations thereof, as well as modified nucleotides, universal bases, adducts, etc. They may be either fully or partially complementary to their cognate target sequences. In addition, they may be labeled or unlabeled.

Detection may be by analysis of cleavage products or by analysis of remaining uncleaved signal probe. Detection of the cleavage products may be through release of a label. Such labels comprise: dyes; radiolabels such as $^{32}$P; binding moieties such as biotin; haptens such as digoxgenin; luminogenic, phosphorescent or fluorogenic moieties; fluorescent dyes alone or in combination with moieties that can suppress or shift emission spectra by fluorescence resonance energy transfer (FRET).

Cleavage products may be analyzed by physical separation (e.g., by electrophoresis, hybridization or by selective binding to a support) or without physical separation (e.g., by changes in fluorescence in FRET-based analysis, or by change in rotation rate in solution in fluorescence polarization analysis).

Cleavage products can be used subsequently in any reaction or read-out method that can make use of oligonucleotides. Such reactions include enzyme dependent modification reaction, such as ligation, tailing with a template-independent nucleic acid polymerase and primer extension with a template-dependent nucleic acid polymerase. The modification of the products may serve to add one or more labels or binding moieties, to alter mass, to add specific sequences, or to otherwise facilitate specific analysis of the cleavage products.

Cleavage product may be used to complete a functional structure, such as a competent promoter for in vitro transcription or other protein binding site. The oligonucleotide product may also be used to complete a cleavage structure to enable a subsequent invasive cleavage reaction, the product of which may be detected or used by any of the methods described above, including the participation in further invasive cleavage reactions.

It is envisioned that any or all of the oligonucleotide probes used in the Invader™ assay may be made to contact non-contiguous sequences in the target strand. In the Examples below, the upstream Invader™ oligonucleotide is made to bridge a structure, thus directing the cleavage of a non-bridging probe.

Specific applications of the structure probing methods of the present invention are described below.

B. Detection and Identification of Pathogens Using the Structure Probing Method 1. Detection and Identification of Multi-Drug Resistant *M. tuberculosis*

In the past decade there has been a tremendous resurgence in the incidence of tuberculosis in this country and throughout the world. In the United States, the incidence of tuberculosis has risen steadily during past decade, accounting for 2000 deaths annually, with as many as 10 million Americans infected with the disease. The situation is critical in New York City, where the incidence has more than doubled in the past decade, accounting for 14% of all new cases in the United States in 1990 (Frieden et al., New Engl. J. Med., 328:521 [1993]).

The crisis in New York City is particularly dire because a significant proportion (as many as one-third) of the recent cases are resistant to one or more anti-tuberculosis drugs (Frieden et al, supra and Hughes, Scrip Magazine May [1994]). Multi-drug resistant tuberculosis (MDR-TB) is an iatrogenic disease that arises from incomplete treatment of a primary infection (Jacobs, Jr., Clin. Infect. Dis., 19:1 [1994]). MDR-TB appears to pose an especially serious risk to the immunocompromised, who are more likely to be infected with MDR-TB strains than are otherwise healthy individuals [Jacobs, Jr., supra]. The mortality rate of MDR-TB in immunocompromised individuals is alarmingly high, often exceeding 90%, compared to a mortality rate of <50% in otherwise uncompromised individuals (Donnabella et al., Am. J. Respir. Dis., 11:639 [1994]).

From a clinical standpoint, tuberculosis has always been difficult to diagnose because of the extremely long generation time of *Mycobacterium tuberculosis* as well as the environmental prevalence of other, faster growing mycobacterial species. The doubling time of *M. tuberculosis* is 20–24 hours, and growth by conventional methods typically requires 4 to 6 weeks to positively identify *M. tuberculosis* (Jacobs, Jr. et al., Science 260:819 [1993] and Shinnick and Jones in *Tuberculosis: Pathogenesis, Protection and Control*, Bloom, ed., American Society of Microbiology, Washington, D.C. [1994], pp. 517–530). It can take an additional 3 to 6 weeks to diagnose the drug susceptibility of a given strain (Shinnick and Jones, supra). Needless to say, the health risks to the infected individual, as well as to the public, during a protracted period in which the patient may or may not be symptomatic, but is almost certainly contagious, are considerable. Once a drug resistance profile has been elucidated and a diagnosis made, treatment of a single patient can cost up to $250,000 and require 24 months.

The recent explosion in the incidence of the disease, together with the dire risks posed by MDR strains, have combined to spur a burst of research activity and commercial development of procedures and products aimed at accelerating the detection of *M. tuberculosis* as well the elucidation of drug resistance profiles of *M. tuberculosis* clinical isolates. A number of these methods are devoted primarily to the task of determining whether a given strain is *M. tuberculosis* or a mycobacterial species other than tuberculosis. Both culture based methods and nucleic-acid based methods have been developed that allow *M. tuberculosis* to be positively identified more rapidly than by classical methods: detection times have been reduced from greater than 6 weeks to as little as two weeks (culture-based methods) or two days (nucleic acid-based methods). While culture-based methods are currently in wide-spread use in clinical laboratories, a number of rapid nucleic acid-based methods that can be applied directly to clinical samples are under development. For all of the techniques described below, it is necessary to first "decontaminate" the clinical samples, such as sputum (usually done by pretreatment with N-acetyl L-cysteine and NaOH) to reduce contamination by non-mycobacterial species (Shinnick and Jones, supra).

The polymerase chain reaction (PCR) has been applied to the detection of *M. tuberculosis* and can be used to detect its presence directly from clinical specimens within one to two days. The more sensitive techniques rely on a two-step procedure: the first step is the PCR amplification itself, the second is an analytical step such as hybridization of the amplicon to a *M. tuberculosis*-specific oligonucleotide probe, or analysis by RFLP or DNA sequencing (Shinnick and Jones, supra).

The Amplified *M. tuberculosis* Direct Test (AMTDT; Gen-Probe) relies on Transcription Mediated Amplification (TMA; essentially a self-sustained sequence reaction [3SR] amplification) to amplify target rRNA sequences directly from clinical specimens. Once the rRNA has been amplified, it is then detected by a dye-labeled assay such as the PACE2. This assay is highly subject to inhibition by substances present in clinical samples.

The Cycling Probe Reaction (CPR; ID Biomedical). This technique, which is under development as a diagnostic tool for detecting the presence of *M. tuberculosis*, measures the accumulation of signal probe molecules. The signal amplification is accomplished by hybridizing tripartite DNA-RNA-DNA probes to target nucleic acids, such as M. tuberculosis-specific sequences. Upon the addition of RNAse H, the RNA portion of the chimeric probe is degraded, releasing the DNA portions, which accumulate linearly over time to indicate that the target sequence is present (Yule, Bio/Technol., 12:1335 [1994]). The need to use of RNA probes is a drawback, particularly for use in crude clinical samples, where RNase contamination is often rampant.

The above nucleic acid-based detection and differentiation methods offer a clear time savings over the more traditional, culture-based methods. While they are beginning to enter the clinical setting, their usefulness in the routine diagnosis of M. tuberculosis is still in question, in large part because of problems with associated with cross-contamination and low-sensitivity relative to culture-based methods. In addition, many of these procedures are limited to analysis of respiratory specimens (Yule, supra).

i) Determination Of The Antibiotic Resistance Profile Of M. tuberculosis a) Culture-based methods: Once a positive identification of M. tuberculosis has been made, it is necessary to characterize the extent and nature of the strain's resistance to antibiotics. The traditional method used to determine antibiotic resistance is the direct proportion agar dilution method, in which dilutions of culture are plated on media containing antibiotics and on control media without antibiotics. This method typically adds an additional 2–6 weeks to the time required for diagnosis and characterization of an unknown clinical sample (Jacobs, Jr., supra).

The Luciferase Reporter Mycobacteriophage (LRM) assay was first described in 1993 (Jacobs, Jr. et al. [1993], supra). In this assay, a mycobacteriophage containing a cloned copy of the luciferase gene is used to infect mycobacterial cultures. In the presence of luciferin and ATP, the expressed luciferase produces photons, easily distinguishable by eye or by a luminometer, allowing a precise determination of the extent of mycobacterial growth in the presence of antibiotics. Once sufficient culture has been obtained (usually 10–14 days post-inoculation), the assay can be completed in 2 days. This method suffers from the fact that the LRM are not specific for M. tuberculosis: they also infect M smegmatis and M. bovis (e.g., BCG), thereby complicating the interpretation of positive results. Discrimination between the two species must be accomplished by growth on specialized media which does not support the growth of M. tuberculosis (e.g., NAP media). This confirmation requires another 2 to 4 days.

The above culture-based methods for determining antibiotic resistance will continue to play a role in assessing the effectiveness of putative new anti-mycobacterial agents and those drugs for which a genetic target has not yet been identified. However, recent success in elucidating the molecular basis for resistance to a number of anti-mycobacterial agents, including many of the front-line drugs, has made possible the use of much faster, more accurate and more informative DNA polymorphism-based assays.

b) DNA-based methods: Genetic loci involved in resistance to isoniazid, rifampin, streptomycin, fluoroquinolones, and ethionamide have been identified (Jacobs, Jr., supra; Heym et al., Lancet 344:293 [1994]; and Morris et al, J. Infect. Dis., 171:954 [1995]. A combination of isoniazid (inh) and rifampin (rif) along with pyrazinamide and ethambutol or streptomycin, is routinely used as the first line of attack against confirmed cases of M. tuberculosis (Banerjee et al., Science 263:227 [1994]). Consequently, resistance to one or more of these drugs can have disastrous implications for short course chemotherapy treatment. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance. The availability of amplification procedures such as PCR and SDA, which have been successful in replicating large amounts of target DNA directly from clinical specimens, makes DNA-based approaches to antibiotic profiling far more rapid than conventional, culture-based methods.

The most widely employed techniques in the genetic identification of mutations leading to drug resistance are DNA sequencing, Restriction Fragment Length Polymorphism (RFLP), PCR-Single Stranded Conformational Polymorphism (PCR-SSCP), and PCR-dideoxyfingerprinting (PCR-ddF). All of these techniques have drawbacks as discussed above. None of them offers a rapid, reproducible means of precisely and uniquely identifying individual alleles.

In contrast, the structure probing methods of the present invention provide an approach that relies on interactions of oligonucleotide probes with the target nucleic acid on the primary, secondary and tertiary structure level. This method requires a fraction of the time, skill and expense of the techniques described above, and can be performed using instrumentation commonly found in the clinical lab (e.g., a microtiter plate reader).

The application of this method to the detection of MDR-TB is illustrated herein using segments of DNA amplified from katg gene. Other genes associated with MDR-TB, including but not limited to those involved in conferring resistance to isoniazid (inhA), streptomycin (rpsL and rrs), and fluoroquinoline (gyrA), are equally well suited to the structure probing assay of the present invention.

2. Detection and Identification of Hepatitis C Virus

Hepatitis C virus (HCV) infection is the predominant cause of post-transfusion non-A, non-B (NANB) hepatitis around the world. In addition, HCV is the major etiologic agent of hepatocellular carcinoma (HCC) and chronic liver disease world wide. HCV infection is transmitted primarily to blood transfusion recipients and intravenous drug users although maternal transmission to offspring and transmission to recipients of organ transplants have been reported.

The genome of the positive-stranded RNA hepatitis C virus comprises several regions including 5' and 3' noncoding regions (i.e., 5' and 3' untranslated regions) and a polyprotein coding region which encodes the core protein (C), two envelope glycoproteins (E1 and E2/NS1) and six nonstructural glycoproteins (NS2-NS5b). Molecular biological analysis of the small (9.4 kb) RNA genome has showed that some regions of the genome are very highly conserved between isolates, while other regions are fairly rapidly changeable. The 5' noncoding region (NCR) is the most highly conserved region in the HCV. These analyses have allowed these viruses to be divided into six basic genotype groups, and then further classified into over a dozen sub-types (the nomenclature and division of HCV genotypes is evolving; See Altamirano et al., J. Infect. Dis., 171:1034 [1995]for a recent classification scheme). These viral groups are associated with different geographical areas, and accurate identification of the agent in outbreaks is important in monitoring the disease. While only Group 1 HCV has been observed in the United States, multiple HCV genotypes have been observed in both Europe and Japan.

The ability to determine the genotype of viral isolates also allows comparisons of the clinical outcomes from infection by the different types of HCV, and from infection by multiple types in a single individual. HCV type has also been associated with differential efficacy of treatment with interferon, with Group 1 infected individuals showing little response (Kanai et al., Lancet 339:1543 [1992] and Yoshioka et al., Hepatol., 16:293 [1992]). Pre-screening of infected individuals for the viral type will allow the clinician to make a more accurate diagnosis, and to avoid costly but fruitless drug treatment.

Existing methods for determining the genotype of HCV isolates include traditional serotyping, PCR amplification of segments of the HCV genome coupled with either DNA sequencing or hybridization to HCV-specific probes and RFLP analysis of PCR amplified HCV DNA. All of these methods suffer from the limitations discussed above (i.e., DNA sequencing is too labor-intensive and expensive to be practical in clinical laboratory settings; RFLP analysis suffers from low sensitivity).

Universal and genotype specific primers have been designed for the amplification of HCV sequences from RNA extracted from plasma or serum (Okamoto et al., J. Gen. Virol., 73:673 [1992]; Yoshioka et al., Hepatol., 16:293 [1992] and Altamirano et al., supra). These primers can be used to generate PCR products which serve as substrates in the structure probing assay of the present invention. As shown herein, the structure probing assay provides a rapid and accurate method of typing HCV isolates. The structure probing analysis of HCV substrates allows a distinction to be made between the major genotypes and subtypes of HCV thus providing improved methods for the genotyping of HCV isolates.

3. Detection and Identification of Bacterial Pathogens

Identification and typing of bacterial pathogens is critical in the clinical management of infectious diseases. Precise identity of a microbe is used not only to differentiate a disease state from a healthy state, but is also fundamental to determining whether and which antibiotics or other antimicrobial therapies are most suitable for treatment. Traditional methods of pathogen typing have used a variety of phenotypic features, including growth characteristics, color, cell or colony morphology, antibiotic susceptibility, staining, smell and reactivity with specific antibodies to identify bacteria. All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. In many cases the pathogens are very similar to the organisms that make up the normal flora, and may be indistinguishable from the innocuous strains by the methods cited above. In these cases, determination of the presence of the pathogenic strain may require the higher resolution afforded by more recently developed molecular typing methods.

A number of methods of examining the genetic material from organisms of interest have been developed. One way of performing this type of analysis is by hybridization of species-specific nucleic acid probes to the DNA or RNA from the organism to be tested. This is done by immobilizing the denatured nucleic acid to be tested on a membrane support, and probing with labeled nucleic acids that will bind only in the presence of the DNA or RNA from the pathogen. In this way, pathogens can be identified. Organisms can be further differentiated by using the RFLP method described above, in which the genomic DNA is digested with one or more restriction enzymes before electrophoretic separation and transfer to a nitrocellulose or nylon membrane support. Probing with the species-specific nucleic acid probes will reveal a banding pattern that, if it shows variation between isolates, can be used as a reproducible way of discriminating between strains. However, these methods are susceptible to the drawbacks outlined above: assays based on sequence-specific hybridization to complex (i.e., whole genome) targets are time-consuming and may give false or misleading results if the stringency of the hybridization is not well controlled, and RFLP identification is dependent on the presence of suitable restriction sites in the DNA to be analyzed.

To address these concerns about hybridization and RFLP as diagnostic tools, several methods of molecular analysis based on polymerase chain reaction (PCR) amplification have gained popularity. In one well-accepted method, called PCR fingerprinting, the size of a fragment generated by PCR is used as an identifier. In this type of assay, the primers are targeted to regions containing variable numbers of tandem repeated sequences (referred to as VNTRs an eukaryotes). The number of repeats, and thus the length of the PCR amplicon, can be characteristic of a given pathogen, and co-amplification of several of these loci in a single reaction can create specific and reproducible fingerprints, allowing discrimination between closely related species.

In some cases where organisms are very closely related, however, the target of the amplification does not display a size difference, and the amplified segment must be further probed to achieve more precise identification. This may be done on a solid support, in a fashion analogous to the whole-genome hybridization described above, but this has the same problem with variable stringency as that assay. Alternatively, the interior of the PCR fragment may be used as a template for a sequence-specific ligation event. As outlined above for the LCR, in this method, single stranded probes to be ligated are positioned along the sequence of interest on either side of an identifying polymorphism, so that the success or failure of the ligation will indicate the presence or absence of a specific nucleotide sequence at that site. With either hybridization or ligation methods of PCR product analysis, knowledge of the precise sequence in the area of probe binding must be obtained in advance, and differences outside the probe binding area are not detected. These methods are poorly suited to the examination and typing of new isolates that have not been fully characterized.

In the methods of the present invention, primers that recognize conserved regions of bacterial ribosomal RNA genes allow amplification of segments of these genes that include sites of variation. The variations in ribosomal gene sequences have become an accepted method not only of differentiating between similar organisms on a DNA sequence level, but their consistent rate of change allows these sequences to be used to evaluate the evolutionary relatedness of organisms. That is to say, the more similar the nucleic acid is at the sequence level, the more closely related the organisms in discussion are considered to be (Woese, Microbiol. Rev., 51:221–271 [1987]). The present invention allows the amplification products derived from these sequences to be used to create highly individual structural fingerprints (e.g., profiles of the complex formation with an array of probes), allowing the detection of sequence polymorphisms without prior knowledge of the site, character or even the presence of the polymorphisms. With appropriate selection of primers, the PCR amplification can be made to be either all-inclusive (e.g., using the most highly conserved ribosomal sequences) to generate PCR products that, when analyzed using the methods of the present invention, allow comparison of distantly related organisms, or the primers can be chosen to be very specific for a given genus, to allow examination at the species and subspecies level. While the examination of ribosomal genes is extremely useful in these characterizations, the use of the structure probing method in bacterial typing is not limited to these genes. Other genes, including but not limited to those associated with specific growth characteristics, (e.g., carbon source preference, antibiotic resistance, resistance to methicillin or antigen production), or with particular cell morphologies (such as pilus formation) are equally well suited to the structure probing assay of the present invention.

C. Extraction of Nucleic Acids From Clinical Samples

To provide nucleic acid substrates for use in the detection and identification of microorganisms in clinical samples using the structure probing assay, nucleic acid is extracted from the sample. The nucleic acid may be extracted from a variety of clinical samples (fresh or frozen tissue, suspensions of cells [e.g., blood], cerebral spinal fluid, sputum, urine, etc.) using a variety of standard techniques or commercially available kits. For example, kits which allow the isolation of RNA or DNA from tissue samples are available from Qiagen, Inc. (Chatsworth, Calif.) and Stratagene (La Jolla, Calif.). For example, the QIAamp Blood kits permit the isolation of DNA from blood (fresh, frozen or dried) as well as bone marrow, body fluids or cell suspensions. QIAamp tissue kits permit the isolation of DNA from tissues such as muscles, organs and tumors.

It has been found that crude extracts from relatively homogenous specimens (such as blood, bacterial colonies, viral plaques, or cerebral spinal fluid) are better suited to severing as templates for the amplification of unique PCR products than are more composite specimens (such as urine, sputum or feces) (Shibata in PCR: *The Polymerase Chain Reaction*, Mullis et al., eds., Birkhauser, Boston [1994], pp. 47–54). Samples which contain relatively few copies of the material to be amplified (i.e., the target nucleic acid), such as cerebral spinal fluid, can be added directly to a PCR. Blood samples have posed a special problem in PCRs due to the inhibitory properties of red blood cells. The red blood cells must be removed prior to the use of blood in a PCR; there are both classical and commercially available methods for this purpose (e.g., QIAamp Blood kits, passage through a Chelex 100 column [BioRad], etc.). Extraction of nucleic acid from sputum, the specimen of choice for the direct detection of *M. tuberculosis*, requires prior decontamination to kill or inhibit the growth of other bacterial species. This decontamination is typically accomplished by treatment of the sample with N-acetyl L-cysteine and NaOH (Shinnick and Jones, supra). This decontamination process is necessary only when the sputum specimen is to be cultured prior to analysis.

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); IVS (intervening sequence); p (plasmid); ml (microliters); ml (milliliters); mg (micrograms); pmoles (picomoles); mg (milligrams); MOPS (3-[N-Morpholino]propanesulfonic acid); M (molar); mM (milliMolar); mM (microMolar); nm (nanometers); nt (nucleotide); bp (base pair); kb (kilobase pair); kdal (kilodaltons); OD (optical density); EDTA (ethylene diamine tetra-acetic acid); FITC (fluorescein isothiocyanate); IPTG (isopropylthiogalactoside); X-Gal (5-bromo-4-chloro-3-indolyl-b-D-galactosidase); SDS (sodium dodecyl sulfate); $NaPO_4$ (sodium phosphate); Tris (tris(hydroxymethyl)-aminomethane); PMSF phenylmethyl-sulfonyifluoride); TBE (Tris-Borate-EDTA, i.e., Tris buffer titrated with boric acid rather than HCl and containing EDTA); PBS (phosphate buffered saline); Ab Peptides (Ab Peptides, St. Louis, Mo.); PPBS (phosphate buffered saline containing 1 mM PMSF); PAGE (polyacrylamide gel electrophoresis); Tween (polyoxyethylene-sorbitan); JBL (JBL, San Louis Obispo, Calif.); Boehringer Mannheim (Boehringer Mannheim, Indianapolis, Ind.); Dynal (Dynal A.S., Oslo, Norway); Epicentre (Epicentre Technologies, Madison, Wis.); MJ Research (MJ Research, Inc., Watertown, Mass.); National Biosciences (National Biosciences, Plymouth, Minn.); New England Biolabs (New England Biolabs, Beverly, Mass.); Novagen (Novagen, Inc., Madison, Wisc.); Perkin Elmer (Perkin Elmer, Norwalk, Conn.); Promega Corp. (Promega Corp., Madison, Wisc.); Stratagene (Stratagene Cloning Systems, La Jolla, Calif.); Third Wave (Third Wave Technologies, Inc., Madison, Wisc.); and USB (U.S. Biochemical, Cleveland, Ohio).

20×SSPE (sodium chloride, sodium phosphate, EDTA) contains per liter: 174 grams NaCl, 27.6 grams $NaH_2PO_4.H_2O$ and 7.4 grams EDTA; the pH is adjusted to 7.4 with NaOH. PBS (phosphate-buffered saline) contains per liter: 8 grams NaCl, 0.2 grams KCl, 1.44 grams $Na_2PO_4$ and 0.24 grams $KH_2PO_4$; the pH is adjusted to 7.4 with HCl.

EXAMPLE 1

The Presence of a Structure and a Probe Mismatch in Combination Provide More Sensitive Discrimination than does Either Effect Alone In this Example, the effects on oligonucleotide binding of either the formation of an occlusive structure, the presence of a single-base mismatch, or the presence of both at once were examined. To separate the effects on the efficiency of binding of structure from the effects of mismatches, four katG DNA target variants were chosen (SEQ ID NOS:1, 2, 3 and 4). The structures of these four targets in the region of the probe hybridization sites are shown in FIG. 2 and the existence of the large stem-loop in structures 2C and 2D (SEQ ID NOS:3 and 4, respectively) was confirmed by digestion with the structure-specific Cleavase®I nuclease (Third Wave) and the cleavage sites are indicated by the arrows on structures 2C and 2D. The dark bar on the left of each structure in FIG. 2 indicates the region to which the capture probe is expected to bind. The pointed kink in the black bar in structures 2B and 2D indicates a site of mismatch between the capture probe and the katG target.
a) CFLP® Analysis of Mutations in the katG Gene of *M. tuberculosis* i) Generation of Plasmids Containing katG Gene Sequences

Genomic DNA isolated from wild-type *M. tuberculosis* or *M. tuberculosis* strains containing mutations in the katG gene associated with isoniazid resistance were obtained from Dr. J. Uhl (Mayo Clinic, Rochester, Minn.). These strains are termed wild-type and S315T (Cockerill, III et al., J. Infect. Dis., 171:240 [1995]). Strain S315T contains a G to C mutation in codon 315 of the wild-type katG gene.

A 620 bp region of the *M. tuberculosis* katG gene was amplified using the PCR from DNA derived from the above strains. The primers used to amplify the katG gene sequences were KatG904 (5'-AGCTCGTATGGCACCGGAAC-3')(SEQ ID NO:5) and KatG1523 (5'-TTGACCTCCCACCCGACTTG-3') (SEQ ID NO:6); these primers amplify a 620 bp region of katG gene. The PCRs were conducted in a final reaction volume of 100 ml and contained the KatG904 and KatG1523 primers at 0.5 mM, 1.5 mM $MgCl_2$, 20 mM Tris-HCl, pH 8.3, 50 mM KCl, 0.05 % each Tween®20 and Nonidet® P-40 non-ionic detergents, 60 mM of all 4 dNTPs. The reaction mixtures were heated at 95° C. for 3 min, then amplification was started with addition of 5 units of Taq DNA polymerase and continued for 35 cycles at 95° C. for 1 min, 60° C. for 1 min and 72° C. for 2 min.

To clone the PCR-amplified katG fragments, 1 ml of each PCR product was used for ligation into the linear pT7Blue T-vector (Novagen, Madison, Wisc.). The ligation products were used to transform competent JM109 cells and clones containing pT7Blue T-vector with an insert were selected by white color on LB plates containing 40 mg/ml X-Gal, 40 mg/ml IPTG and 50 mg/ml ampicillin. For each of the PCR samples, four colonies were picked and grown overnight in 2 ml LB media containing 50 mg/ml carbenicillin. Plasmid DNA was isolated using an alkaline miniprep protocol (Sambrook et al., supra).

To analyze the cloned katG fragments, 1 ml of plasmid DNA from each clone was amplified by PCR using 100 ml reactions containing the KatG904 and KatG1523 primers at 0.5 mM, 1.5 mM $MgCl_2$, 20 mM Tris-HCl, pH 8.3, 50 mM KCl, 0.05 % each Tween®-20 and Nonidet® P-40 non-ionic detergents, 60 mM of all 4 dNTPs and 5 units of Taq DNA polymerase. The PCRs were cycled 35 times at 95° C. for 1 min, 60° C. for 1 min and 72° C. for 2 min. PCR products were separated by electrophoresis on a 6% native polyacrylamide gel in 0.5×TBE buffer and clones that gave rise to a 620 bp fragment were selected for further analysis.

Fragments of DNA (391 bp), labeled on the 5' end of the sense strand with tetrachlorofluorescein (TET), were created from the cloned katG genes using primers 5'-TET-AGCTCGTATGGCACCGGAACC-3' (SEQ ID NO:7) and 5'-GGACCAGC GGCCCAAGGTAT-3' (SEQ ID NO:8). When the wild type katG DNA fragment of this size is denatured by heating and allowed to fold, nucleotides A37–45 base pair with nucleotides G381-T389 (measured from the 5' end of the sense strand). The wild type sequence has a G at bp 41 (G41) which is complimentary to the C at bp 385 (C385) as shown in FIG. 2C; the S315T mutant sequence contains a C at bp 41 (C41) which is non-complimentary to C385 and disrupts the formation of the hairpin, as shown in FIG. 2B. Two additional non-wild type sequences were created by using an alternative primer at the 3', end (5'-GGACCACCGGCCCAAGGTATCT-3'; SEQ ID NO:9) which changed C385 to G385. This allowed creation of fragments with a G41 to G385 mismatch (FIG. 2A) and a C41 to G385 base pair (FIG. 2D).

The PCR reactions were performed aS follows: PCR mixtures contained 5 ng of plasmid DNA template, 1×PCR buffer, 200 mM of each dNTP, 0.5 mM of each primer, 5 units of Taq Polymerase and water to final volume of 100 ml. The PCR cycling conditions were: 95° C. for 45", 65° C. for 1'30" and 72° C. for 2' for a total of 30 cycles, followed by a 4° C. soak. The 391 bp PCR products were purified using "High Pure PCR Product Purification Kit" (Boehringer Mannheim). ThiS set of fragments (SEQ ID NOS:1–4) allowed a single probe to be used to assess the effects of mismatch, secondary structure or a combination of both on the formation of the complex between the probe and target.

ii) CFLP® Reactions

CFLP® reactions were performed on each 5'-TET labeled amplification product from the four KatG variants (2A–2D). Each CFLP® reaction contained approximately 20 fmole of the amplified product, 50 units of Cleavase® I nuclease in 10 ml of 1×CFLP® buffer (10 mM MOPS pH 7.5, 0.05% Tween® 20 and 0.05% Nonidet® P40 non-ionic detergents) with 0.2 mM $MnCl_2$. Reactions were assembled with all components except the enzyme and the $MnCl_2$, heated to 95° C. for 15 seconds, then cooled to the reaction temperature of 50° C. The cleavage reactions were started with the addition of the enzyme and the $MnCl_2$, and incubated for 5 minutes. The reactions were terminated by the addition of 4 ml of 95% formamide with 10 mM EDTA and 0.02% Methyl Violet. The products were heated at 95° C. for 30 sec, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the left panel of FIG. 3. Lanes A–D contain CFLP reaction products from reactions containing structures 2A–2D, respectively. Lanes C and D contain a product (37 nt; indicated by the arrowhead) not present in lanes A and B which indicates the presence of the large stem-loop in structures 2C and 2D shown in FIG. 2.

b) Structure Probing Analysis of *M. tuberculosis* katG Gene Targets

In these experiments, the capture probes are bound to the target DNAs in solution and then immobilized on a solid support. The 391 bp fragment of katg described above was created by PCR using a 5' -fluorescein labelled primer (SEQ ID NO:7). A hybridization mixture was assembled, containing 40 finoles of heat-denatured, 391 bp katG PCR product having one of the four sequences depicted in FIG. 2 (SEQ ID NOS:1–4), labelled on the 5' end of the sense strand, 1 pmole of the biotinylated capture probe (SEQ ID NO:10), 10 mg/ml tRNA, 0.2% acetylated BSA, 4.5×SSPE and $H_2O$ to 100 ml.

Aliquots (100 ml) of the mixture were then transferred to wells in a streptavidin-coated 96-well plate (Boehringer Mannheim) and incubated at room temperature for 30 min. The plate was then washed three times with 1×PBS, with 0.01% Tween®-20 non-ionic detergent, then treated with a solution containing 0.2% I-Block (Tropix, Bedford, Mass.) and 0.05% Tween®-20 non-ionic detergent in PBS for 30 minutes to block. After blocking, the plate was washed three times with PBS with 0.1% Tween®-20 non-ionic detergent. A 1:5000 dilution of 0.75 u/ml anti-fluorescein antibody conjugated with alkaline-phosphatase in 0.2% I-block buffer was added to the plate in 100 ml/well volumes. After ½ hour, the plate was washed three times with TBS (25 mM Tris-Cl, 0.15 M NaCl, pH 7.2). One hundred microliters of Attophos® fluorescent substrate (JBL) was added to each well and the plate was incubated at room temperature for 1 hour before fluorescence readings were taken using a Perkin-Elmer Cytofluor-4000 set to excite at 450/50 nm and to and detect emission at 580/50 nm. Each assay was performed in triplicate and the standard deviation is represented by the black bar at the top of each column in the right panel of FIG. 3. The fluorescence intensity is indicated in arbitrary fluorescence units. In FIG. 3, "A–D" indicates the use of structures 2A–2D, respectively in the structure probing assay.

The results, shown in FIG. 3, indicate that not only the mismatch between target DNA and probe, but also differences in secondary structure, leads to a better discrimination between wild type and mutant DNA.

EXAMPLE 2

Figure 4:
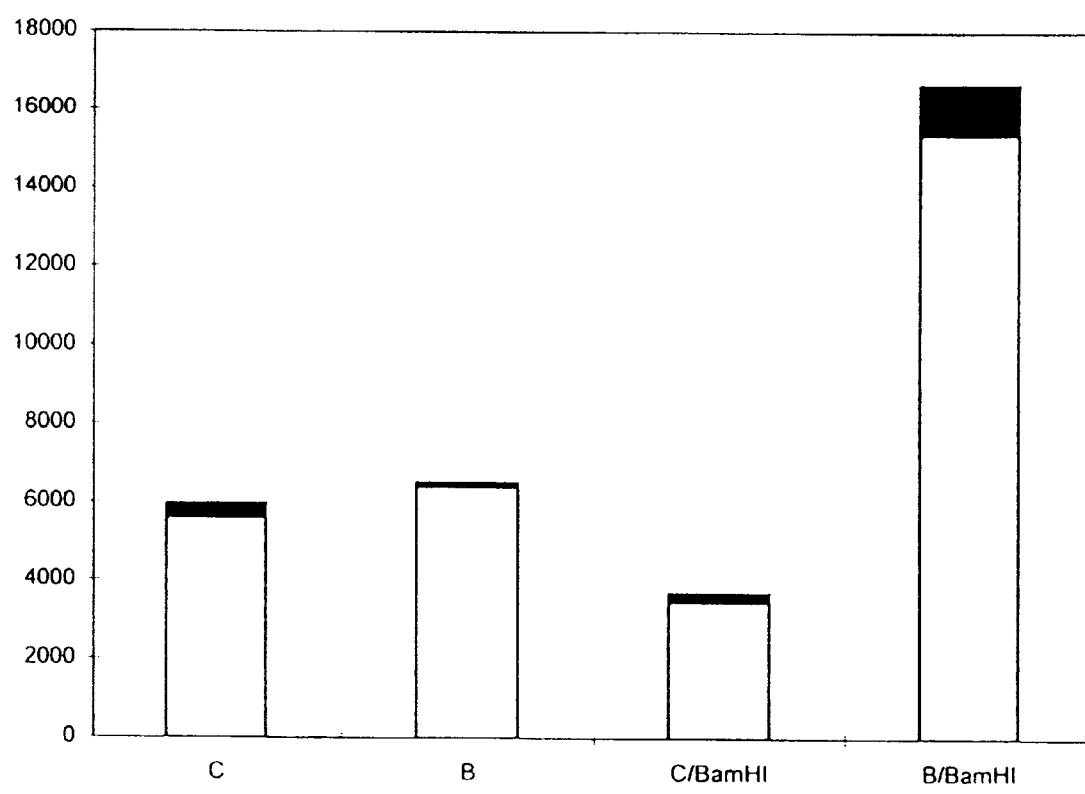

Changes in DNA Secondary Structure Leads to Different Binding Abilities Between the Target DNA and the Capture Probe The context of a target sequence (i.e., the length and identity of the flanking nucleic acid), can influence the secondary structure, and therefore the hybridization accessibility of the target segment. To illustrate this effect, a target segment of DNA was exposed, either with or without pretreatment with a restriction enzyme, to a capture probe that is complementary to a site that is unaffected by the restriction cleavage. The restriction enzyme BamHI was used to digest the 391 bp 5'-fluorescein labeled fragments of katG DNA, either wild-type (FIG. 2C) or the S315T mutant (FIG. 2B), prepared as described in Example 1. The restriction enzyme shortens the 5' labelled fragment from 391 nt to 256 nt. The capture probe is complementary to sequence located within the first 50 nt of these katG DNA targets. Equal amounts of the DNA targets were used in all the reactions. The restriction digests included 2 pmoles of 5'-Fluorescein labeled DNA, 10 ml of 10×BamHI buffer, 160 units of BamHI enzyme and $H_2O$ to a final volume of 100 ml. The reactions were incubated at 37° C. for 2 hours. After digestion, the hybridization assay was performed as described above, using the capture probe (SEQ ID NO:10). The results are shown in FIG. 4. In FIG. 4, the amount of labeled target captured (as a target/probe complex) is shown for each target/probe complex examined (shown using arbitrary fluorescence units). In FIG. 4, the following abbreviations are used: C (structure 2C); B (structure 2B); C/BamHI (BamHI-digested structure 2C); B/BamHI (BamHI-digested structure 2B).

The 2C DNA target (SEQ ID NO:3) has a site perfectly complementary to the capture probe, while the 2B DNA target (SEQ ID NO:2) has a single base mismatch near the middle of the region of complementarity with the capture probe. Despite this mismatch, discrimination between these two 391 nt DNAs (i.e., not digested with BamHI) by hybridization to this probe is very weak. As shown in FIG. 4, the difference in the binding efficiency between wild type and mutant DNA after enzyme digestion is increased. Because the segment of the katG DNA to which the probe hybridizes is not cleaved by the enzyme, it can be concluded that it is the change in the folded structure of the target DNA that accounts for the change in the hybridization pattern. This shows that, while mismatches may enhance discrimination between nucleic acid variants, they are not necessary for discrimination between DNAs by hybridization. These results also demonstrate that variables other than the degree of complementarity (e.g., complete or partial) between the probe and target (e.g., the secondary and tertiary structure of the target) may provide a better means of discriminating between related sequences.

EXAMPLE 3

Hybridization Analysis using Multiple Capture Probes for HCV Genotyping

Figure 5:
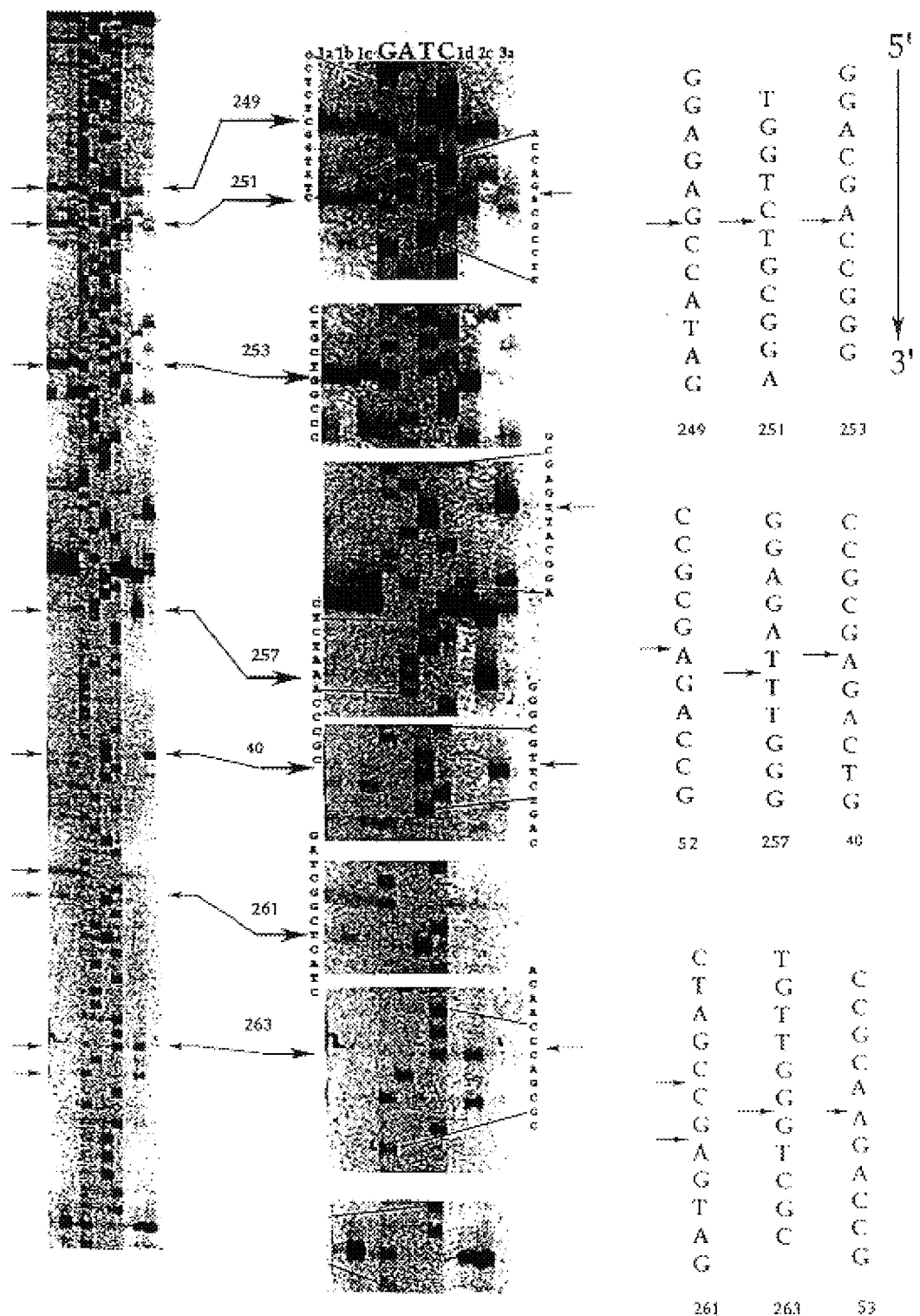

Because both mismatches and structures are used in the method of the present invention for discrimination between similar nucleic acids by hybridization, the patterns created by the use of a structure specific nuclease, e.g., Cleavase® I nuclease can be used as a way of selecting regions likely to demonstrate different binding behaviors with different variants. Because the CFLP® method indicates the presence of structure in a DNA fragment of interest, and because the variations in the structures tend to be proximal to the actual sequence changes, choosing capture probes at or near the CFLP® cleavage sites increases the probability of choosing a sequence that changes in accessibility in the different variants. FIG. 5 shows a diagram depicting this means of probe selection as applied to the comparison of fragments from the Hepatitis C virus. In FIG. 5, the left panel shows an fluoroimager scan of sequencing gel in which products of CFLP® cleavage reactions are resolved next to a sequencing ladder generated using the same target DNA employed in the CFLP® cleavage reactions. The middle panel provides an enlargement of sections of the gel shown in the left panel. The right panel provides the sequence of nine HCV probes (SEQ ID NOS:11–19); these probe were synthesized such that they contained a 5'-biotin moiety.

Five subtypes of HCV; 1a, 1b, 2b, 2c, and 3a were analyzed using both the CFLP® cleavage method, and cycle sequencing. The CFLP® reactions were performed on each 5'-fluorescein labeled amplification product from each HCV isolate as follows. Each CFLP® reaction contained approximately 20 fmole of the amplified product, 25 units of Cleavase® I nuclease in 10 ml of 1×CFLP® buffer (10 mM MOPS pH 7.5, 0.05% Tween® 20 and 0.05% Nonidet® P40 non-ionic detergents) with 0.2 mM $MnCl_2$. Reactions were assembled with all components except the enzyme and the $MnCl_2$, heated to 95° C. for 15 seconds, then cooled to the reaction temperature of 55° C. The cleavage reactions were started with the addition of the enzyme and the $MnCl_2$, and incubated for 2 minutes. The reactions were terminated by the addition of 4 ml of 95% formamide with 10 mM EDTA and 0.02% Methyl Violet. The products were heated at 85° C. for 2 min, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi).

The CFLP® patterns for these HCV subtypes are shown in FIG. 5. Different subtypes of HCV give different CFLP® patterns, which means that they also have different internal secondary structure. Probes were designed to detect structure differences between the 1a, 1b, 2c and 3a HCV subtypes. The capture probes are shown in the right panel of FIG. 5. The region to which each of these HCV capture probes can bind along the sequence of the HCV targets is shown in FIG. 6. In FIG. 6, the location of the probe binding regions are indicated using bold type, underlining and by placing the probe designation above the sequence. The consensus HCV sequence (SEQ ID NO:20), and the sequence of HCV subtypes 1a, 1b, 2c and 3a (SEQ ID NOS:20–23, respectively) are provided.

Figure 7:
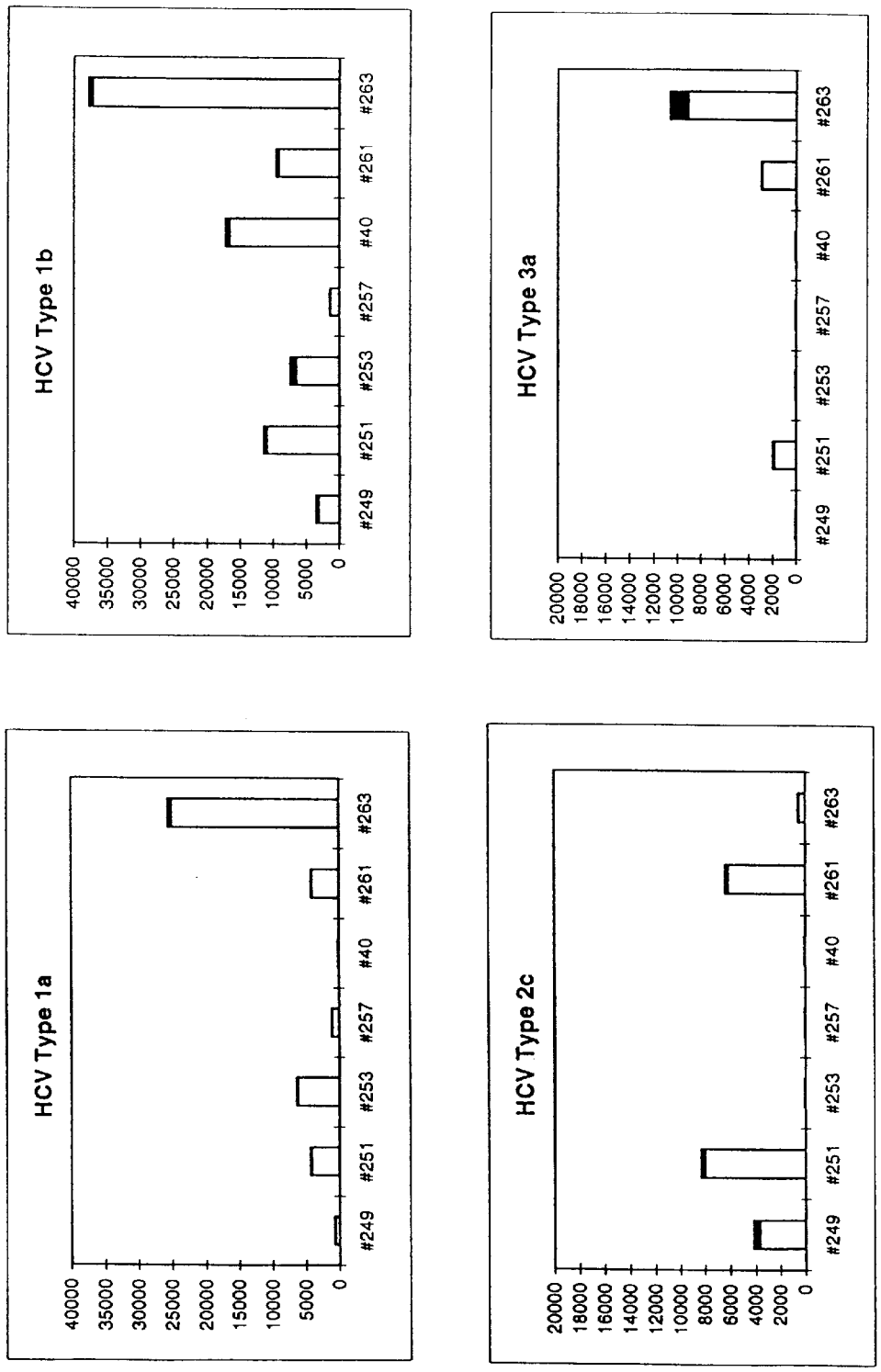

The capture probes (SEQ ID NOS:11–19) were synthetically labeled with biotin at their 5' end and purified by gel-electrophoresis. The HCV target DNA was labeled with fluorescein at the 5' end of the antisense strand by PCR using a 5'-fluorescein labeled primer. The primers employed for the amplification of HCV target DNAs were: 5' primer: 5'-Fl-CTCGCAAGCACCCTATCA (SEQ ID NO:24) and 3' primer: 5'-GCAGAAAGCGTCTAGCCATGG (SEQ ID NO:25). The PCR reactions included 5 ng of plasmid DNA template, 1×PCR buffer (Boehringer Mannheim), 200 mM of each dNTP, 0.5 mM of each primer (SEQ ID NOS:24 and 25), 5 units Taq DNA polymerase (Boehringer Mannheim) and water to a final volume of 100 ml. The PCR cycling conditions were: 95° C. for 45", 55° C. for 45", and 72° C. for 1', for 30 cycles followed by a 72° C. for 5' extension and a 4° C. soak. The resulting 244 bp PCR products (SEQ ID NOS:26–29 for types 1a, 1b, 2c and 3a, respectively) were purified using "High Pure PCR Product Purification Kit" (Boehringer Mannheim) and eluted in dH$_2$O according to the manufacturer's instructions. The same amount of DNA, based on optical absorbance, was used for each sample in the capture assay. Structure probing analysis on streptavidin-coated 96-well micro-titer plates was performed as described above. Each assay was performed in triplicate and the standard deviation is shown as a black bar at the top of each column in FIG. 7. The results are shown in FIG. 7.

The column graphs of the measured fluorescence intensity for the complexes between each probe and a given target constitute a characteristic "signature" that is distinctive for each HCV subtype. The effects of structure can be illustrated by examining the signal strengths from targets binding to probe #40 (SEQ ID NO:16). While both the 1b and 3a targets are completely complementary to probe #40, the 3a target shows nearly undetectable signal, while the type 1b target signal is very strong. The binding of probe #251 (SEQ ID NO:12) to the HCV targets shows similar signal variation even though this probe is completely complementary to all four of the HCV subtype targets.

EXAMPLE 4

Effect of Temperature on Structure Probing with Oligonucleotides

Most traditional hybridization methods have a small window of temperature (i.e., about less than 10° C.) in which to produce the expected discrimination between targets. The structure probing analysis of the four HCV subtypes (describe above) under different hybridization temperatures was performed to examine the effect of temperature on both the secondary structure of DNA and the stability of the probe/target complex. Three different temperatures were used; room temperature (approx. 20 to 25° C.), 37° C. and 50° C.

The profile of the HCV subtypes 1a, 1b and 3a are shown in FIG. 7. The profiles of the HCV subtype 1b are shown in FIG. 8B, The profiles of the HCV subtype 3a are shown in FIG. 8C. The hybridization profiles of these three HCV subtypes over a 25° C. range of temperature (~25–50° C.) are shown in FIGS. 8A–8C (the numbers below each column indicates the capture probe employed; note the change in scale for each temperature tested). The profiles for these three HCV subtypes are essentially the same over the 25° C. range of temperature tested. However, the higher the temperature employed, the less stable the probe-DNA target binding becomes, so the overall fluorescence intensity was reduced. These results show that the discrimination capability of the structure probing method is very robust, maintaining consistency over a broad range of temperature.

EXAMPLE 5

Structure Probing Analysis of HCV Clinical Isolates

Structure probing analysis of HCV clinical isolates at a room temperature hybridization temperature was performed to examine the feasibility of developing a diagnostic test for HCV genotyping. Twelve HCV amplification products generated from clinical samples were obtained (Molecular Pathology Dept, Univ. of Wisconsin Clinics, Madison, Wisc.) and employed in the structure probe assay. These targets were RT-PCR products of viral RNA from different patient samples amplified using the Amplicor HCV detection kit (Roche Molecular Systems, Alameda, Calif.). Further PCR reactions were performed on these clinical amplification products using the primer pair described in Example 4 (SEQ ID NOS:24 and 25) to create ds PCR products comprising 5' fluorescein labels on the anti-sense strands. The PCR conditions were as described in Example 4. The resulting HCV targets were employed in the structure probing assay which was carried out as described in Example 1.

The resulting profiles were sorted by type (based on the profiles determined for the HCV subtypes as described in Examples 3 and 4 and FIG. 7) and are shown in FIGS. 9A–9D (the types were independently determined by single pass DNA sequencing. The resulting partial sequences, sufficient to identify types are as follows: #67 (SEQ ID NO:30), #69 (SEQ ID NO:31), #72 (SEQ ID NO:32), #73 (SEQ ID NO:33), #74 (SEQ ID NO:34), #81 (SEQ NO:35), #85 (SEQ ID NO:36), #86 (SEQ ID NO:37) and #91 (SEQ ID NO:38).

Figure 9A:
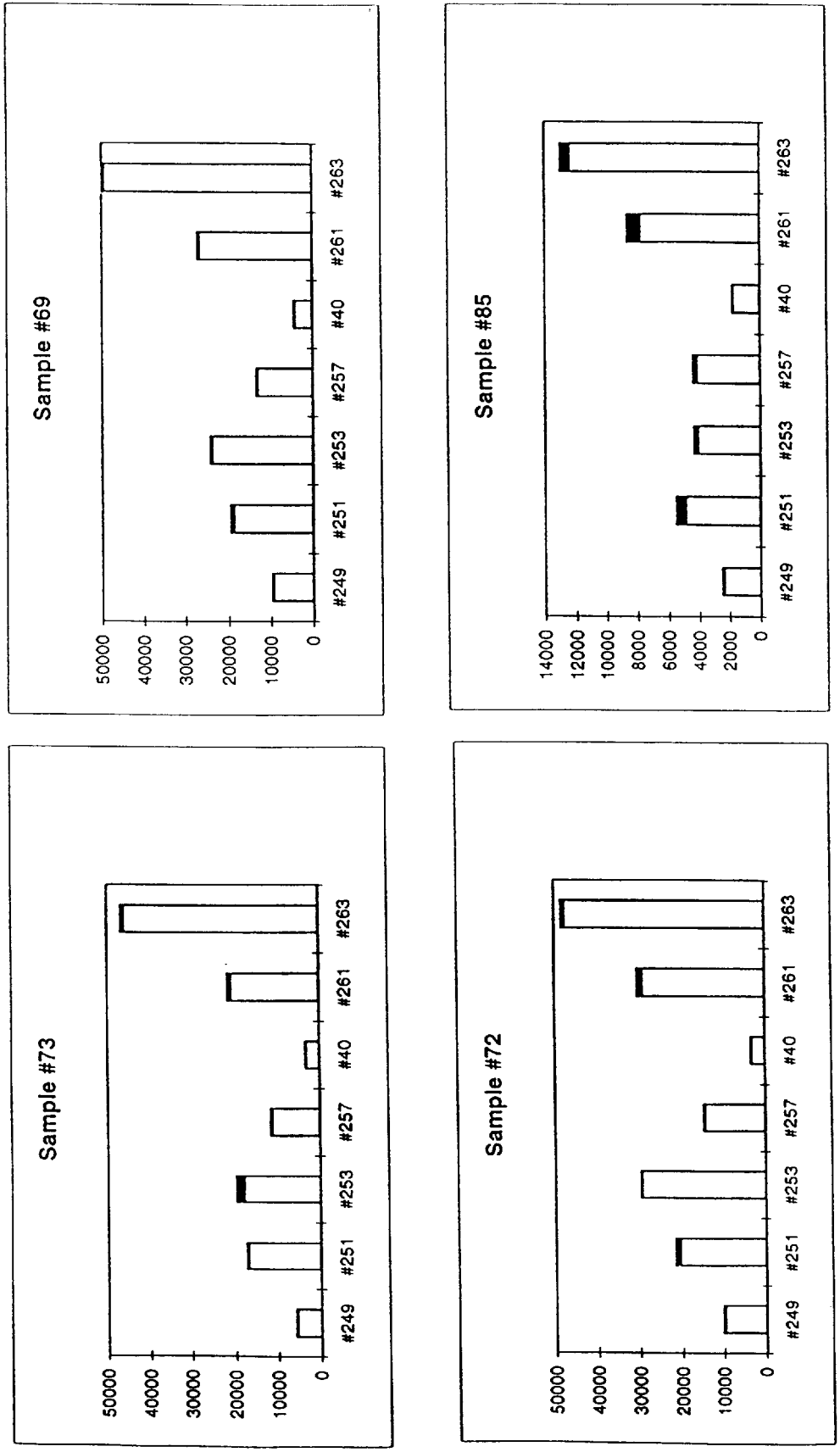
Figure 9B:
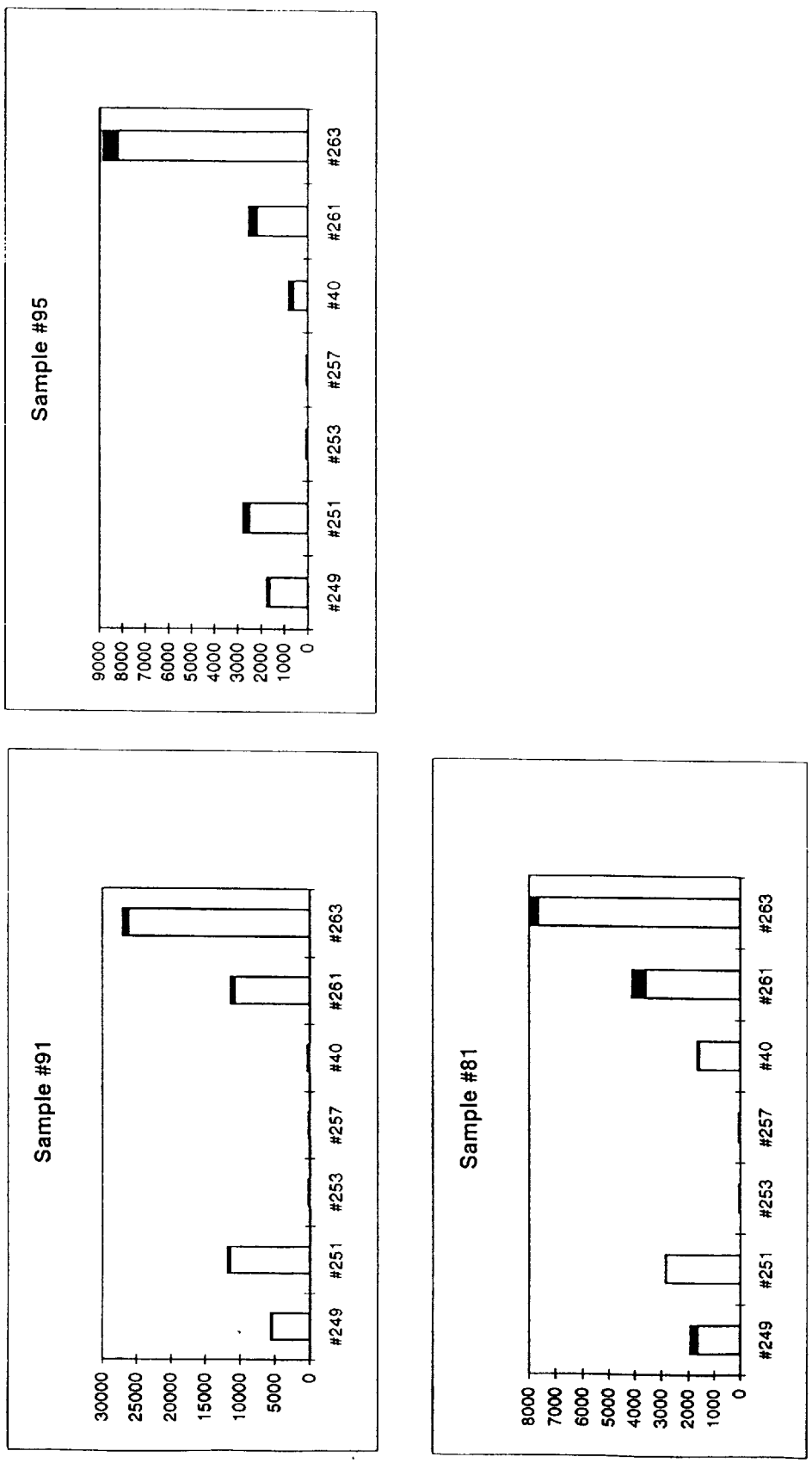
Figure 9C:
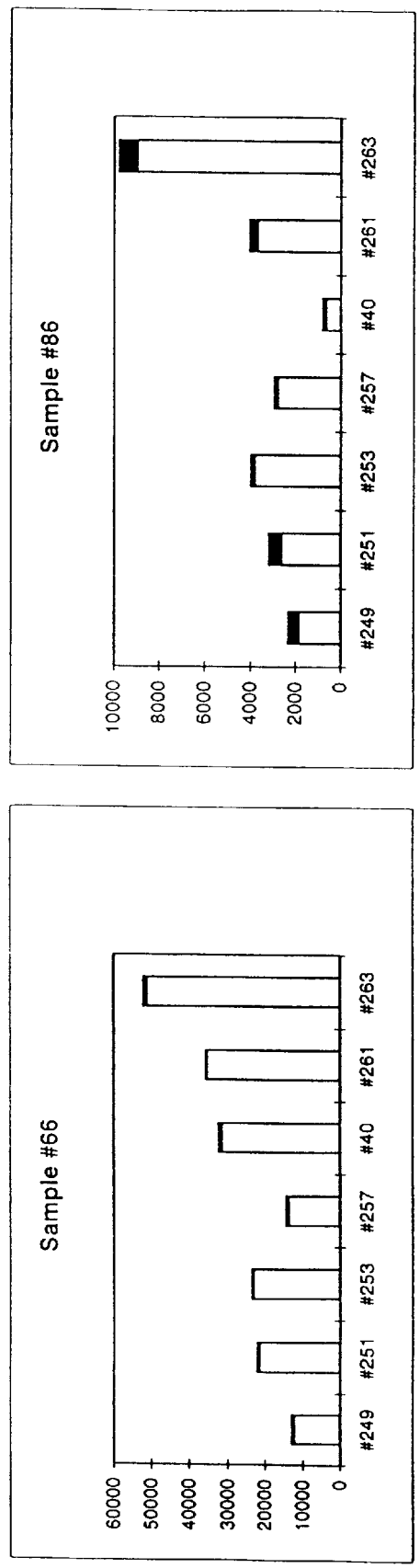

The profiles for four different amplicons of HCV type 1a are shown in FIG. 9A (#69, #72, #73 and #85) and all have a profile similar to the type 1a profile shown in FIG. 7. The profiles of three different amplicons of HCV type 3a are shown in FIG. 9B (#81, #91 and #95) and their profiles are all similar to each other and to the type 3a profile shown in FIG. 7. The profile of an amplicon of HCV type 2c (#67) and an amplicon of HCV type 2b (#74) are shown in FIG. 9D. The profiles for two amplicons of HCV 1b are shown in FIG. 9C (#66 and #86).

The profile for amplicon #86 was more similar to that of type 1rather than type 1b. Based on CFLP® analysis, amplicon #86 was classified as type 1b. However, using the probe set shown in FIG. 9C, the hybridization profile obtained in the structure probing assay appeared more similar to that of type 1a. Sequence analysis showed that there is an extra mutation in this sample, which changed its hybridization response to probe #40, creating a profile more like that of type 1a. Based on this T to C mutation in amplicon #86, an additional capture probe having a sequence completely complimentary to amplicon #86 was tested (probe #53; SEQ ID NO:19). A structure probing assay using the amplicon #86 target and capture probe #53 generated a profile similar to a more typical type 1b profile. These results demonstrate that additional information concerning the structure of the amplicon #86 target was obtained using the structure probing assay.

These data demonstrate that an unknown (i.e., uncharacterized) set of HCV isolates can be identified by HCV type through the use of the structure probing assay, with comparison of the resulting profiles to those of previously characterized isolates (i.e., reference profiles).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

Thus, the previous Examples that oligonucleotide binding is affected by the formation of an occlusive structure in the target DNA. In each of these cases, the oligonucleotides used to bind and capture the target nucleic acid were designed to be substantially complementary to a single region of the target. The following two Examples demonstrate the use of oligonucleotides that are designed to interact with multiple, non-contiguous regions of the target DNA. In some embodiments of the methods of the present invention, the oligonucleotides (i.e., bridging oligonucleotides) are designed to interact with regions that are brought into close proximity by the formation of folded structure in the target strand. By using short sections of complementarity on either side of the connecting segment, it is intended that the bridge oligonucleotides be dependent on the binding of both of the sections of complementarity, and that changes in, or the absence of, the intervening folded structure cause a significant change in the affinity between the bridge oligonucleotide and the target DNA.

EXAMPLE 6

Size of Complementary Regions Affects the Ability of Bridging Oligonucleotides to Discriminate Between Targets that Contain Identical Regions of Complementarity, but Different Folded Structures In this Example, the effect of length of complementarity on each side of the bridge oligonucleotides on the ability of the bridge oligonucleotide to distinguish between test molecule #80, 81 and 82 (SEQ ID NOS:39–41) was examined. As noted above, these oligonucleotides have identical regions of complementarity to which the bridge oligonucleotides of this Example may hybridize. The bridge oligonucleotides used in this test are shown in the lower half of FIG. 11A, arranged in the orientation in which they would hybridize to test molecule #80 (SEQ ID NO:39). Three bridging oligonucleotides, shown as #78, #4 and #79 (SEQ ID NOS:42, 43, 44), were used, and these had 6, 7 or 8 nucleotides of complementarity, respectively, to each side of the hairpin formed in target #80 (SEQ ID NO:39). The two regions of target complementarity were separated by a pair of thymidine nucleotides in each oligonucleotides to provide additional flexibility to the three-leg junction (Zhong et al., Biochem., 32:6898 [1993]; and Yang et al, Biochem., 35:7959 [1996]). All the biotinylated oligonucleotides were gel-purified after synthesis using the standard oligonucleotide purification methods.

In these hybridization analyses, the capture probes were bound to the target DNAs in solution and then immobilized on a solid support, as described in the previous Examples. For each of these tests (each of the three bridge oligonucleotides listed above was tested on each of the three test molecules), a hybridization mixture was assembled containing 20 fmols of a fluorescein-labeled test molecule as depicted in FIG. 10 (SEQ ID NOS:39–41), 1.5 pmole of one of the biotinylated capture probe 78, 4 or 79 (SEQ ID NOS:42–44), 10 mg/ml tRNA and 0.2% acetylated BSA, in 150 ml of 4.5×SSPE. The mixture was incubated at room temperature for 30 min.

Aliquots (100 ul) of the mixtures were then transferred to wells in a streptavidin-coated 96-well plate (Boehringer Mannheim) and incubated at room temperature for 20 min. The plate was then washed three times with TBS (25 mM Tris-Cl, 0.15 M NaCl, pH 7.2) with 0.01% Tween®-20 non-ionic detergent. Then, 100 µl of a 1:5000 dilution of 0.75 u/ml anti-fluorescein antibody conjugated with alkaline-phosphatase in 0.2% I-block buffer (Tropix, Bedford, Mass.) was added to each well. After 20 min at room temperature, the plate was washed three times with TBS with 0.01% Tween®-20. Then, 100 ml of Attophos fluorescent substrate (JBL, San Luis Obisbo, Calif.) were added to each well and the plate was incubated at 37° C. for 1 hour, before fluorescence readings were taken using a Perkin-Elmer Cytofluor-4000 set to excite at 450/50 nm and to and detect emission at 580/50 nm. Each assay was performed in duplicate and the standard deviation is represented by the black bar at the top of each column in the right panel of FIG. 12. In this Figure, the fluorescence intensity is indicated in arbitrary fluorescence units.

Figure 12:
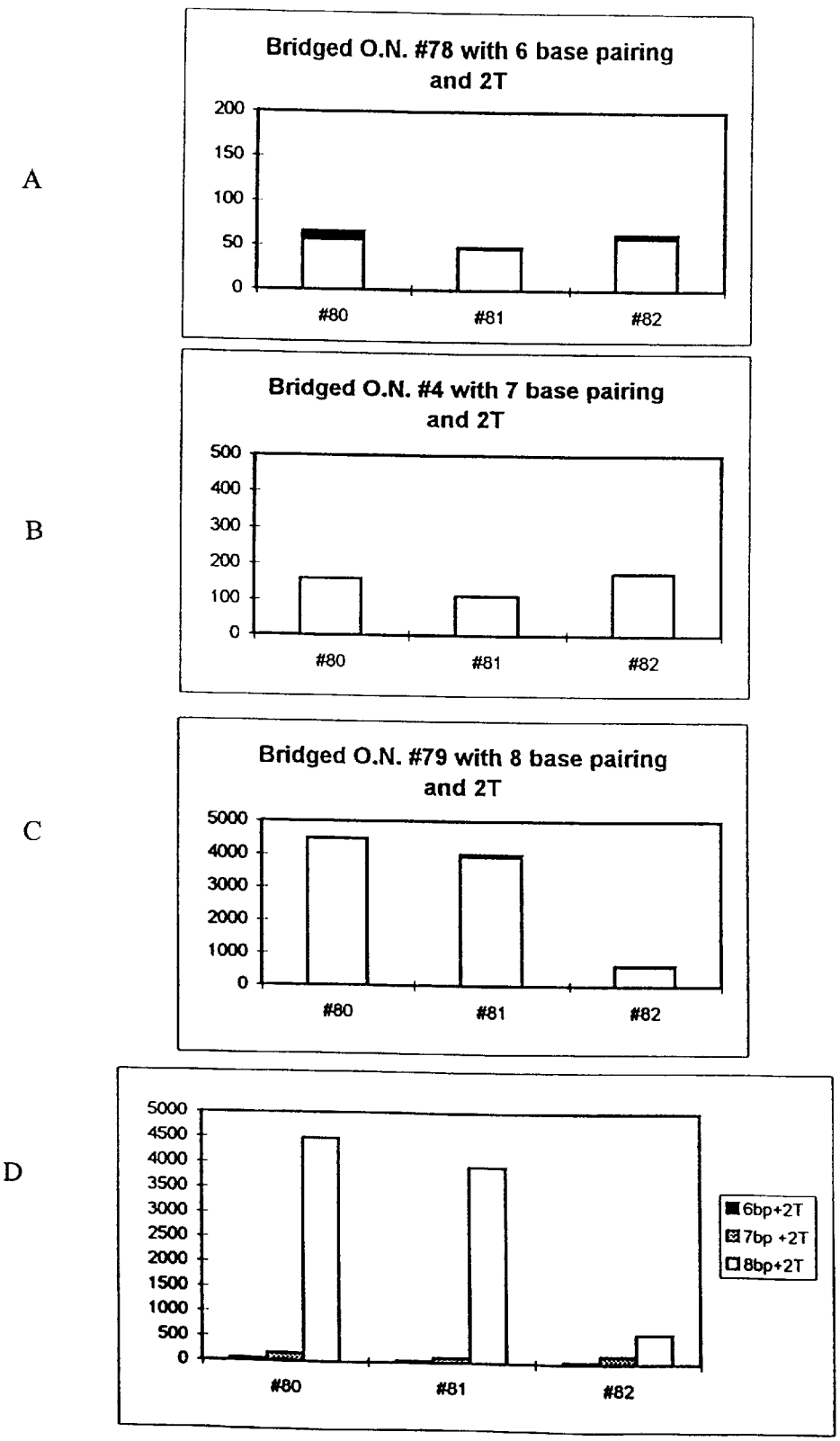

The results, shown in FIG. 12, indicate that the bridging oligonucleotide #79 (SEQ ID NO:44), having 8 bases pairing to each side of the hairpin in the DNA target, gives better binding activity to the target DNA than oligonucleotides that have 7 bases pairing (#4; SEQ ID NO:43), which is better than oligonucleotides that have only 6 bases pairing (#78; SEQ ID NO:42). Furthermore, the oligonucleotides with the shorter flanking sequences did not show any significant difference in binding to the different test molecules, indicating that the presence or absence of structure was immaterial to their binding under these test conditions. In contrast, the oligonucleotide with the 8 bp flanks had a 6 to 7 -fold higher affinity for the folded molecules #80 (SEQ ID NO:39) and #81 (SEQ ID NO:40), when compared to the unstructured #82 (SEQ ID NO:41) molecule. This demonstrated that bridge oligonucleotides are suitable for the assessment of differences in folded structure of a target molecule, in contrast to previous reports (Francois et al., Nucl. Acid. Res. 22: 3943 [1994]).

While the 8-bp flanks are clearly the preferred size in this experimental system, the absolute number of basepairs required for any particular bridge oligonucleotide system may vary other factors affecting the stability of the interaction, as discussed above, such as with the G-C content of the hybridization site, the temperature and solution conditions under which the reaction is performed, and the nature of the structure to be bridged. Thus, it is contemplated that in some systems, bridge oligonucleotides comprise any appropriate length suitable for the assay system.

EXAMPLE 7

Bridging Oligonucleotides

In this Example, two schemes were investigated in order to determine how the bridging oligonucleotide might bind to the targeted hairpin structure, as illustrated in FIG. 11B. Although an understanding of the mechanism is not necessary in order to make and use the present invention, nor is it intended that the present invention be limited to any particular mechanism, one possibility is that one bridging oligonucleotide molecule binds to one DNA target molecule, as diagrammed in the top half of the Figure. A second possibility is that two or more of the bridging oligonucleotide molecules bind to one DNA target molecule, with the apparent increase in signal resulting from the presence of two biotin moieties on the complex facilitating binding or detection, rather than successfully spanning of a structure by a single bridge oligonucleotide.

To differentiate these two possibilities, two additional oligonucleotides were synthesized (oligonucleotide #114 and #115 [SEQ ID NOS:45 and 46, respectively]), as shown in FIG. 11B. Oligonucleotide #114 (SEQ ID NO:45) is almost identical to #79 (SEQ ID NO:44), except that two mutations have been introduced in such way that it cannot hybridize to the right side of the hairpin on the target DNA. Similarly, oligonucleotide #115 (SEQ ID NO:46) is a version of #79 (SEQ ID NO:44) having two base mutations so that it can't hybridize to the left side if the hairpin on the target DNA. If the ability of oligonucleotide #79 (SEQ ID NO:44) to bind to the folded molecules is truly dependent on a single oligonucleotide bridging the structure then neither of the 'pseudo' bridge oligonucleotides, #114 or #115 (SEQ ID NOS:45 and 46, respectively), should be able to perform in this way. However, if the increased binding is in fact due to the presence of two copies of # 79 (SEQ ID NO:44), which would be arranged as depicted for #114 and #115 (SEQ ID NOS:45 and 46, respectively) in the bottom half of FIG. 11B, then #114 and #115 (SEQ ID NOS:45 and 46, respectively) used together should give the same result.

Figure 11A:

In addition to the test of the bridging function, the necessity of the spacing thymidines in the center of each bridge oligonucleotide was assessed. An oligonucleotide having the same complementary flanking sequences as oligonucleotide #79, but lacking the two T's in the middle, was created. This oligonucleotide (#116 [SEQ ID NO:47]), is depicted in the bottom half of FIG. 11A. In addition, to test the necessity of having a physical linkage between the binding halves of #79 (SEQ ID NO:44), to half molecules were created, each having complementarity to one of side of the test molecules, #117 (SEQ ID NO:48) to the right side and #118 (SEQ ID NO:49) to left side, as depicted in FIG. 11A, and each having one of the two spacer T residues. Finally, two 10-mer oligonucleotides were created, each with sufficient contiguous complementarity to bind without any bridging activity. One of these was complementary to the left flank (#FD91; SEQ ID NO:50), which is unstructured in all cases, while the other was complementary to the sequence involved in the structures of the folded test molecules (#2; SEQ ID NO:51). These are depicted in the top half of FIG. 11A.

The hybridization analyses were performed as described in Example 6, except that 15 finoles of the fluorescein labeled test molecules were used, and the amount of bridge oligonucleotide was held to a total of 1.5 pmole when #114 and #115 (SEQ ID NOS:45 and 46, respectively) were used in combination. The results are shown in FIGS. 13A and 13B.

Taking the results in reverse order: the 10-mer control oligonucleotides showed the expected profiles in binding i.e., the oligonucleotide complementary to the unstructured region, #FD91 (SEQ ID NO:50), bound with nearly equal affinity to each of the test molecules, while the oligonucleotide complementary to the portion that forms structure in molecules #80 and #81 (SEQ ID NOS:39 and 40, respectively) bound well only to unstructured test molecule #82 (SEQ ID NO:41). This further illustrates that structure alone is an important determinant in the binding of the capture probes in embodiments of the methods of the present invention.

Figure 13A:
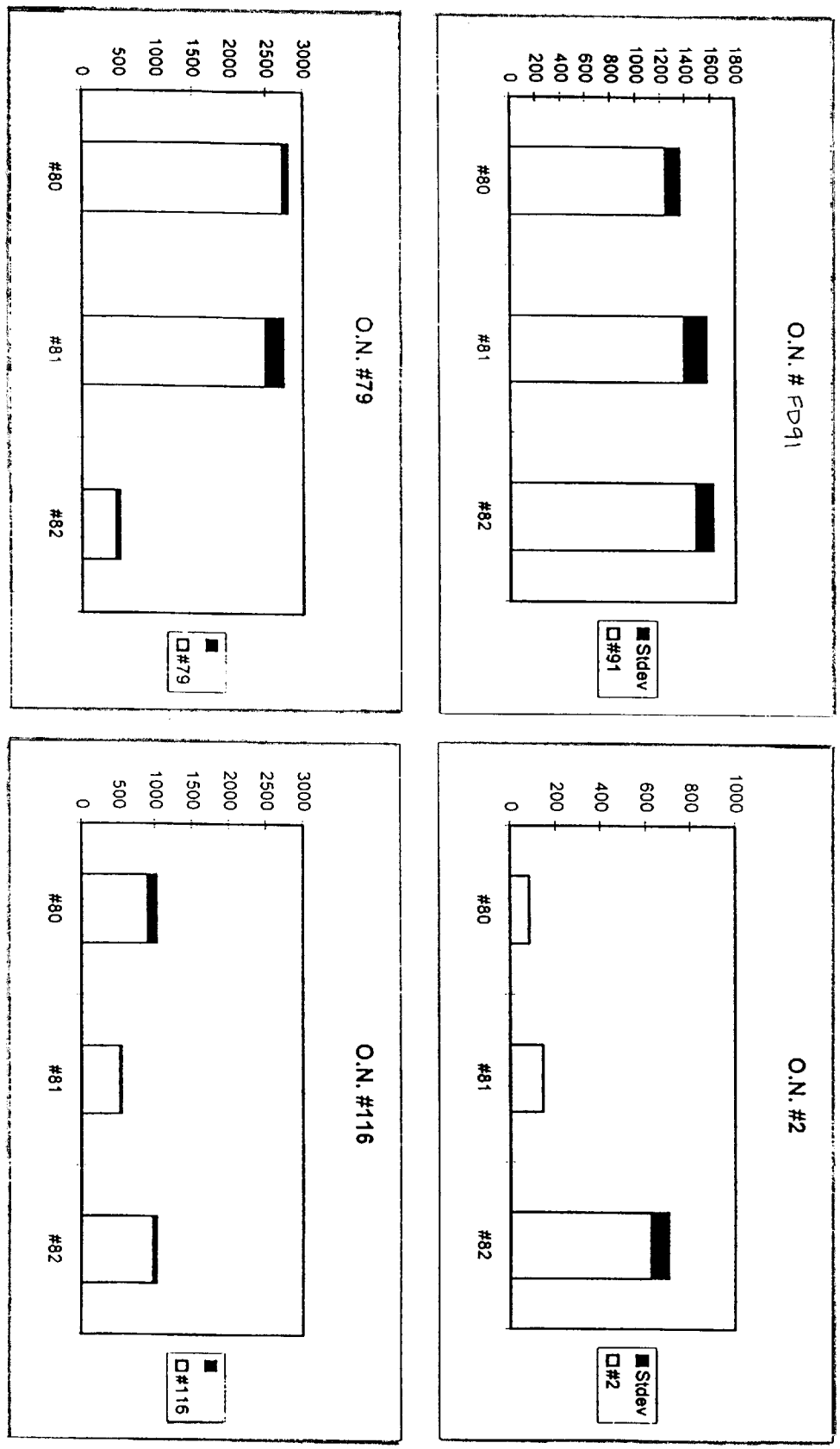

When the oligonucleotide without any spacer residues, #116 (SEQ ID NO:47), was tested for its ability to bind the test molecules, it was found that this oligonucleotide could not distinguish between the folded and unfolded molecules (See, FIG. 13A). This demonstrated that hybridization across structures is greatly enhanced by the presence of some spacing material between the segments of complementarity.

Figure 13B:
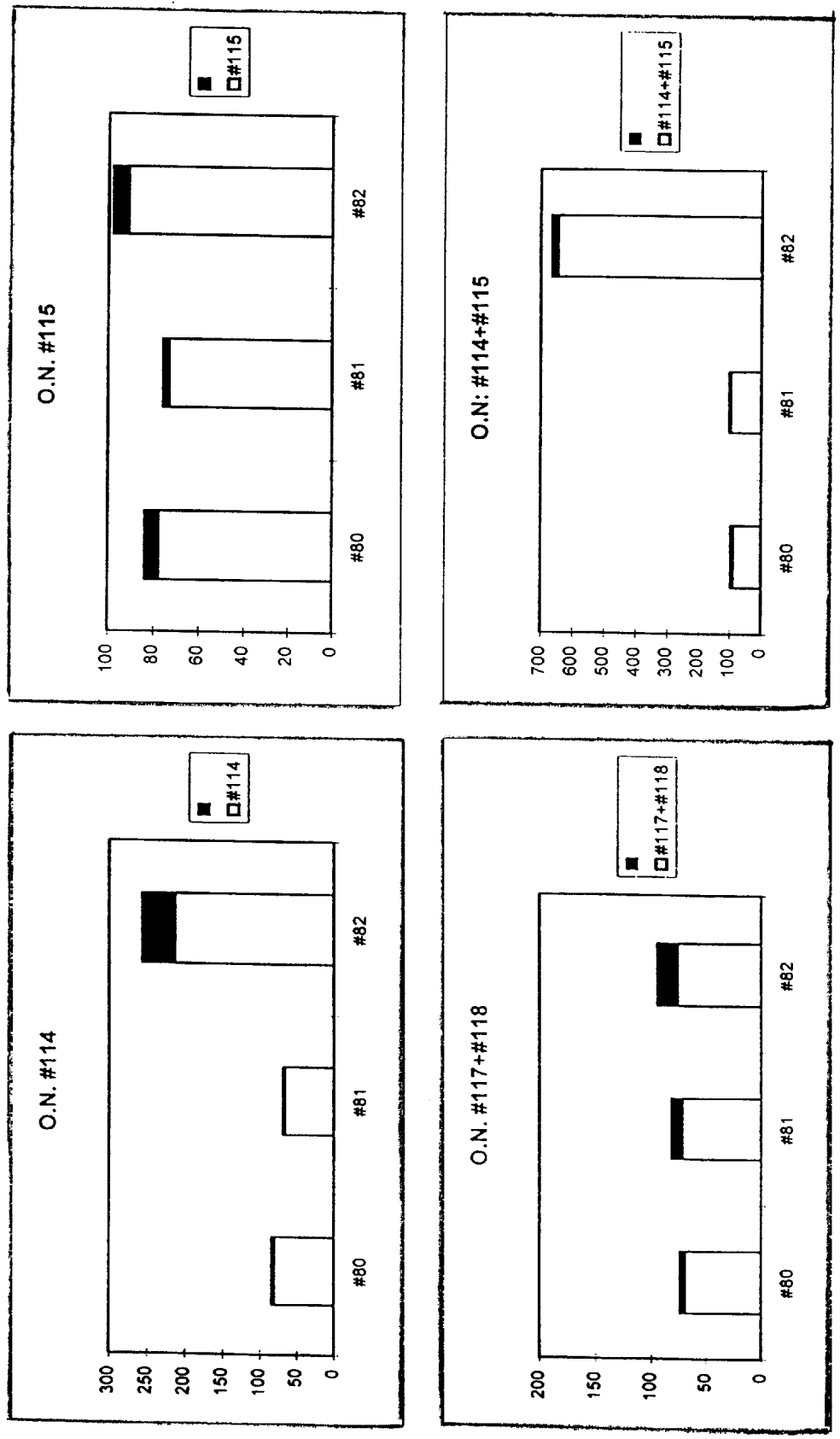

Finally, the results of testing the pseudo bridge oligonucleotides, separately and in combination, are shown in FIG. 13B. It can be seen by these data, that oligonucleotides #114 and #115 (SEQ ID NOS:45 and 46, respectively) are not capable, either alone or in combination, to duplicate the binding profile of the true bridge, #79 (SEQ ID NO:44). The enhanced binding to the unstructured test molecule #82 (SEQ ID NO:41) is possibly attributable to the accessibility of this molecule for binding both oligonucleotides. Note that the fluorescence signal seen with the combination of #s 114, 115 and molecule #82 (SEQ ID NOS: 45, 46, and 41, respectively), about 650 fluorescence units, is nearly identical to the signal seen when #79 (SEQ ID NO:44) is combined with #82 (SEQ ID NO:41). This supports the idea that two copies of #79 (SEQ ID NO:44) may be involved in creating the signal with # 82 (SEQ ID NO:41).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

The previous examples demonstrated the use of bridging oligonucleotides to capture specific target molecules through hybridization to non-contiguous complementary sequences. However, the use of bridging oligonucleotides is not limited to hybrid capture. Bridging oligonucleotides hybridizing to folded target molecules can be used in place of standard oligonucleotides in almost any application, including applications in which enzymes modify probes that have found their target complement. Such enzymatic modifications include, but are not limited to primer extension, ligation and structure-specific nuclease cleavage. It will easily be appreciated by those skilled in the art that performance of bridging oligonucleotides in these basic enzymatic reactions is indicative of their utility in assays that are based on reiterative performance of these reactions, including but not limited to cycle sequencing, polymerase chain reaction, ligase chain reaction, cycling probe reaction and the Invader™ invasive cleavage reaction. The examples below demonstrate the use of bridging oligonucleotides in each of the basic enzymatic reaction systems.

EXAMPLE 8

Analysis of Folded Structures of a Hepatitis C Virus-Derived Amplicon and Design of Bridging Oligonucleotides The process of identifying candidate structures for bridging with probes involves i) pinpointing all modification or cleavage sites; ii) predicting a set of most probable structures, and selecting those that fit with the specificity of the modification means; and iii) designing and testing probes to span the most probably structures. If desired, the information deduced at step ii) can be confirmed by deletion analysis such as PCR walking, or any equivalent method that allows the selective repression or removal of one half of a suspected basepair from interaction.

This stepwise approach is illustrated here for a 244 nt amplicon derived from HCV type 1a. The identification of the cleavage sites in all four types of HCV amplicon is described in Example 3. FIG. 15 shows sequence of 5' UTR region of HCV genotypes 1a, 1b, 2a/c and 3a with marked cleavage sites. Note that the designations 2a and 2a/c are used interchangeably throughout, and refer to the same HCV viral type, the amplicon of which is SEQ ID NO:22.

Figure 16A:
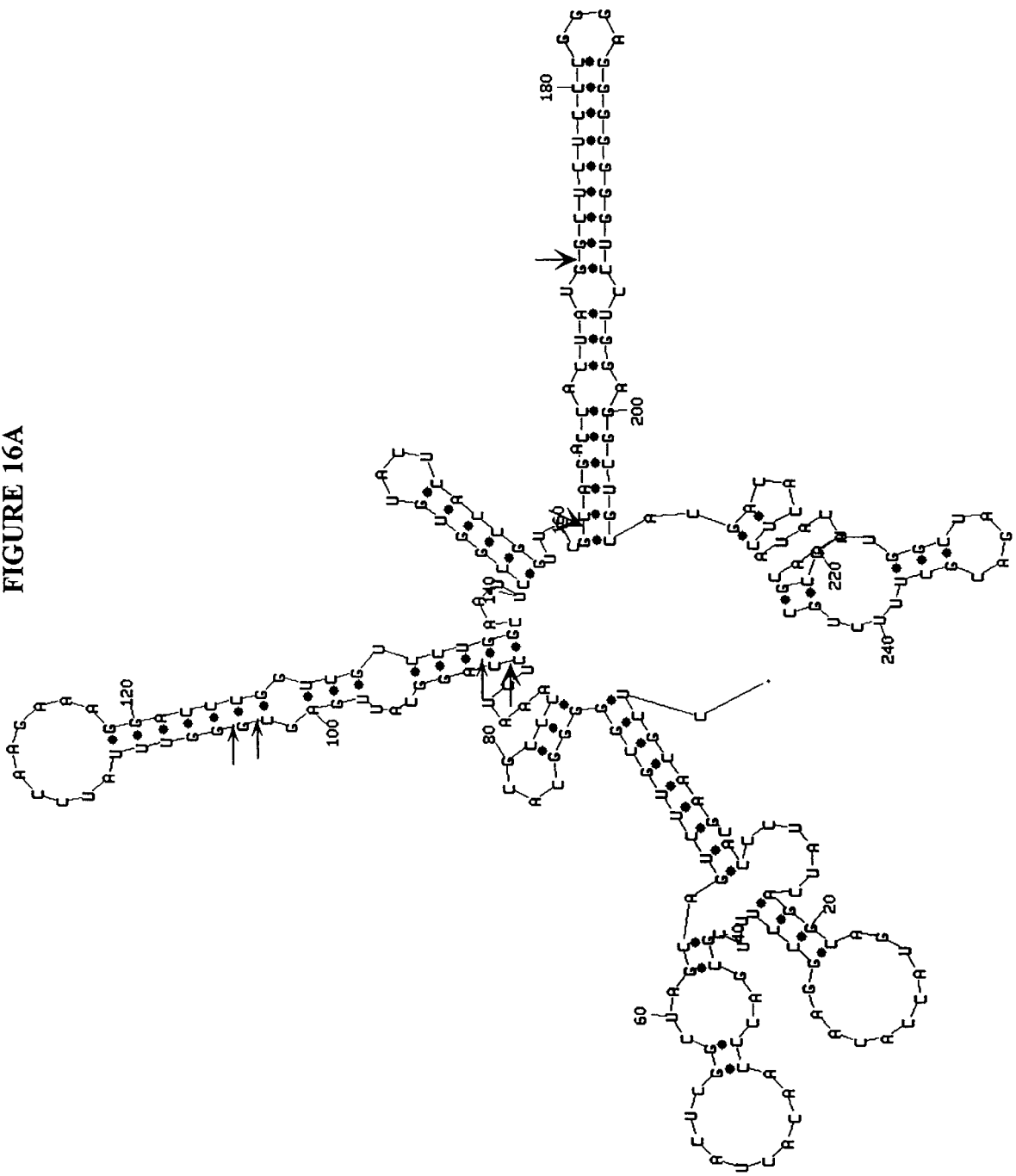
Figure 16B:
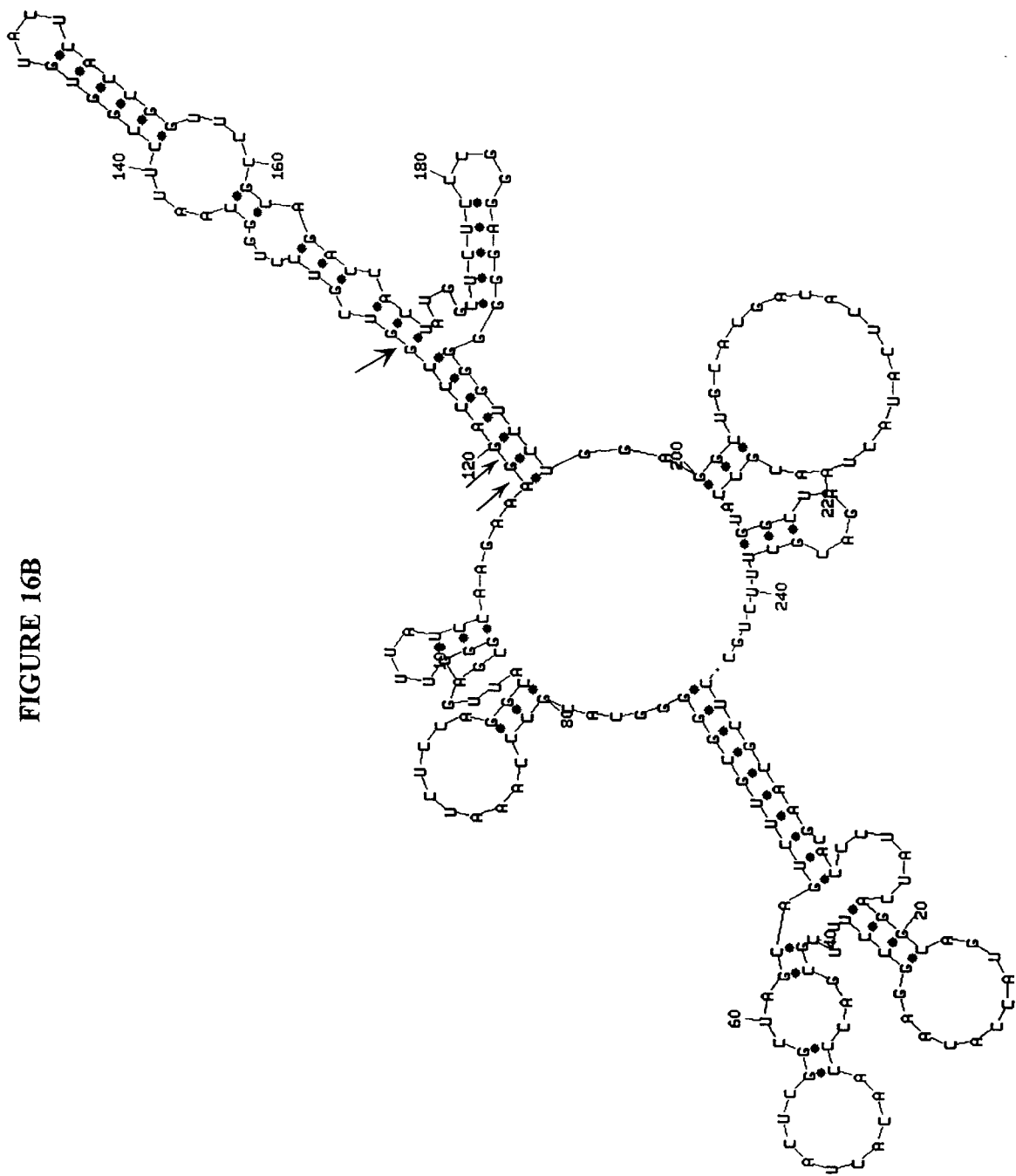

The type 1a sequence as then subjected to folding predictions using the mfold version 2.3 program, which is available either through Genetics Computer Group (Madison, Wisc.) or through public access to the authors' web site (http://www.ibc.wustl.edu/~zuker). Folding was done with using either DNA or RNA parameters with a selected folding temperature of 37° C. The output was set to include the optimal structure (lowest free energy) and any structure with a 20 percent or lower increase in calculated free energy (termed a "suboptimality of 20%"). All other program parameters used the default values. Folding with the RNA parameters generated 32 possible structures, while the DNA parameters gave 18 structures. Two of the structures predicted with the RNA parameters showed the best agreement with the cleavage data from the CFLP® analysis. These structures, the first and the thirtieth out of 32, are depicted in FIGS. 16A and 16B.

Figure 17A:
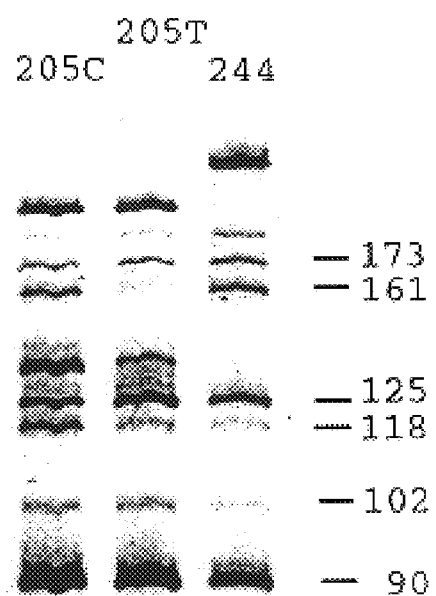

Structures predicted by the above analysis can be confirmed through the use of CFLP® analysis on fragments that delete the putative downstream pairing partner (Brow et al., supra). This approach, termed PCR walking, is illustrated here by the confirmation of the pairing partner responsible for the CFLP® cleavage at position 161 in the HCV type 1a 244 nt amplicon. The mfold program predicted a structure that paired a G at 161 with a C at position 205 (FIG. 17A, left conformer). To confirm this two deletion amplicons were made. Each amplicon was 205 nt long. One included the C205 at the 3' end, while the other substituted a T at 205 to disrupt the basepair. PCR was conducted as described in Example 3, except the downstream primers 67 and 68 were substituted for (SEQ ID NO:25) used to amplify the full length amplicons. The resulting DNAs were purified and subjected to CFLP® analysis, resolved and visualized as described in Example 3. The resulting image is shown in FIG. 17B. The identity of residue 205 in the deletion fragments is indicated above each lane, and the sizes of selected cleavage bands, as determined by comparison to a sequencing ladder in Example 3, are indicated on the right.

Focusing on the band that was the subject of this analysis, at 161 nt, it can be seen that the amplicon having the natural 205C maintained the 161 cleavage, while disruption of this base pair in the 205T fragment caused a loss of that band, thus supporting the existence of the 161/205 interaction. It should be noted that it is possible that the 205 nt base does not interact directly with the 161G, and that the C to T change caused a conformational change elsewhere, which altered the 161-containing structure as a secondary effect. While this is less likely, the possibility should always be kept in mind when analyzing the data, especially if unexpected results arise. Not surprisingly, the deletions and mutations also give rise to pattern changes elsewhere in the pattern, indicating how little change is required to be detectable by CFLP®.

Figure 17C:
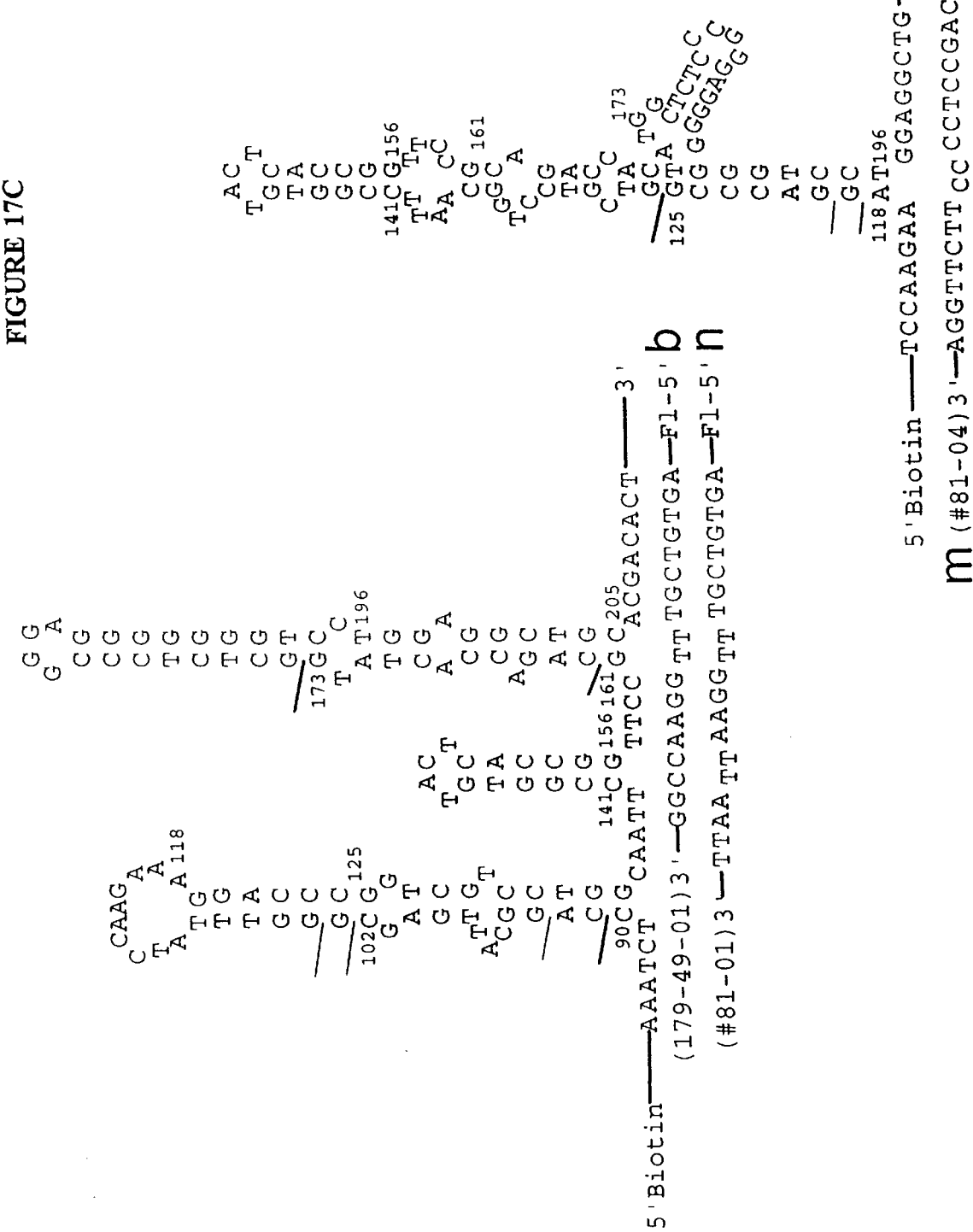

Based on the combined CFLP®, mfold, and PCR walking data, three of the most likely conformations for this region were chosen and three bridge oligonucleotides were designed to span the structures. These are shown schematically in FIG. 17C. The "b" (SEQ ID NO:53) and "n" (SEQ ID NO:65) variants address essentially the same conformation with a difference related to the small central stem. Though predicted by mfold, the presence of this structure is not predicted by the CFLP® pattern for the 244-mer (FIG. 17A, right lane). Consequently, bridge probes were designed that either spanned that structure ("n"; SEQ ID NO:65) or that complemented the 8 contiguous bases upstream of the larger stem ("b"; SEQ ID NO:53). The "m" (SEQ ID NO:64) bridge probe was designed to cross the base of the single stem of the other conformer. Each of the these probes was tested for binding to the HCV 1a amplicon as described in Example 6. While the "m" (SEQ ID NO:64) and "n" (SEQ ID NO:65) probes failed to capture significant amounts of target, the "b" (SEQ ID NO:53) probe was found to be effective, as will be illustrated in the following examples.

Figure 18A:
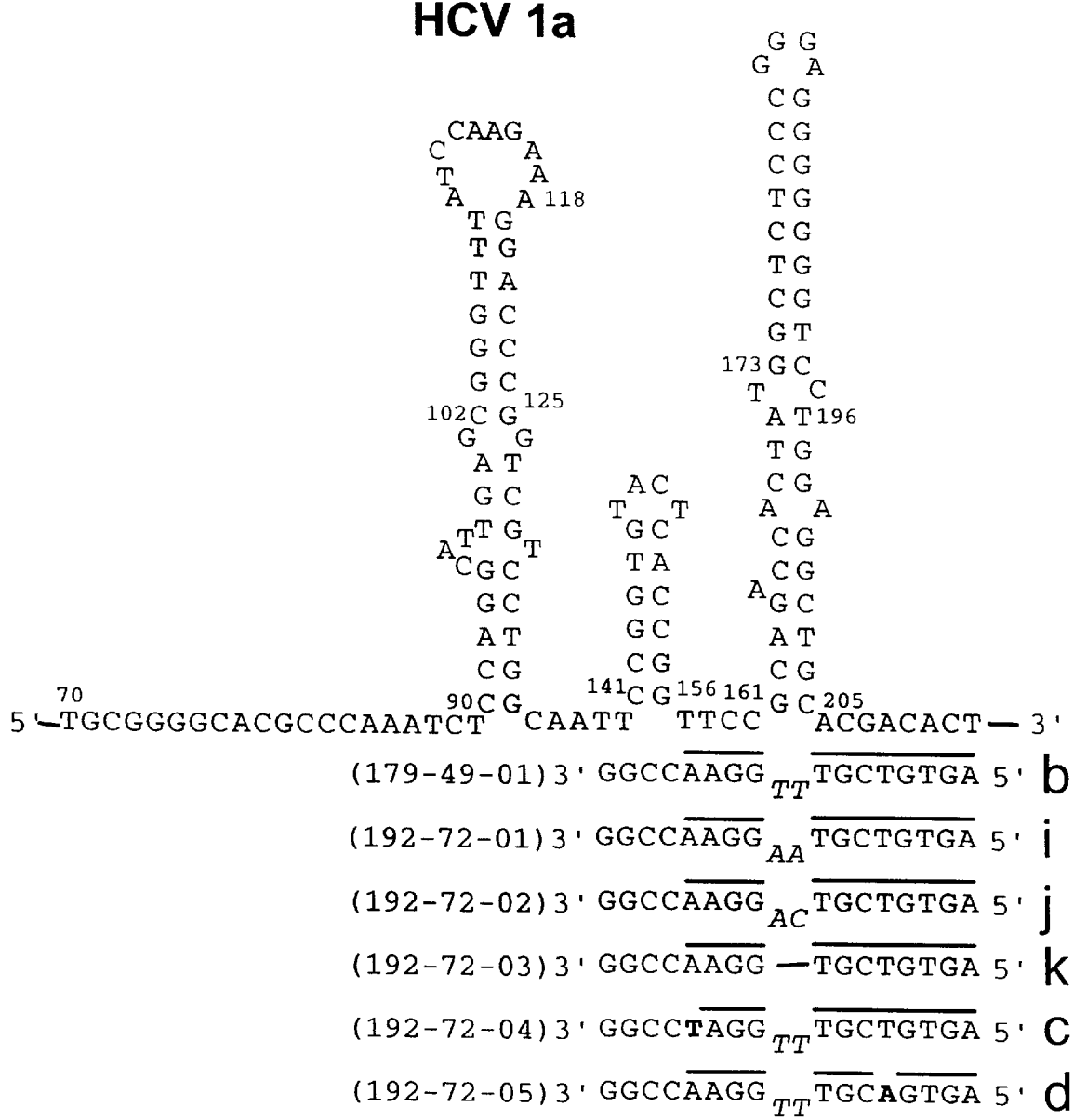
Figure 18B:
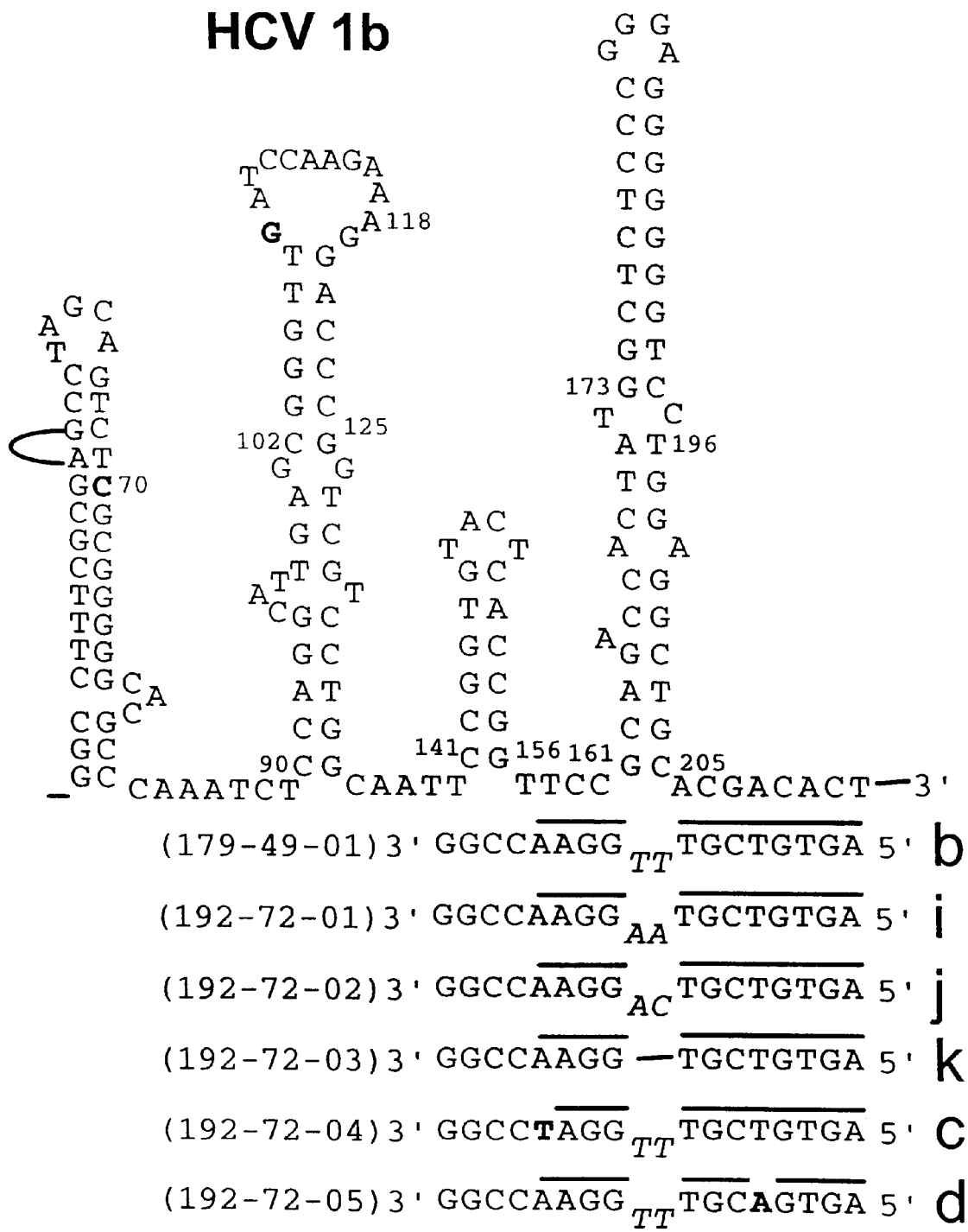

Using the "b" oligonucleotide (SEQ ID NO:53) as a model, a number of variant bridges were designed to compare the effects of different intervening sequences in the probes and on the inclusion of mismatches in either contact sequence. These bridge probes are diagrammed schematically as they would align with the HCV 1a predicted structure are shown in FIG. 18A. The connecting line in the center of the "k" probe (SEQ ID NO:56) indicates that the two portions are linked directly together without any intervening sequence. Modifications to the intervening region included the use of alternative nucleotides in to link the contact sequences and the omission of additional intervening nucleotides. A mismatch was included in the middle of either of the two contact sequences to assess whether the binding of both is necessary for capture.

Figure 19:
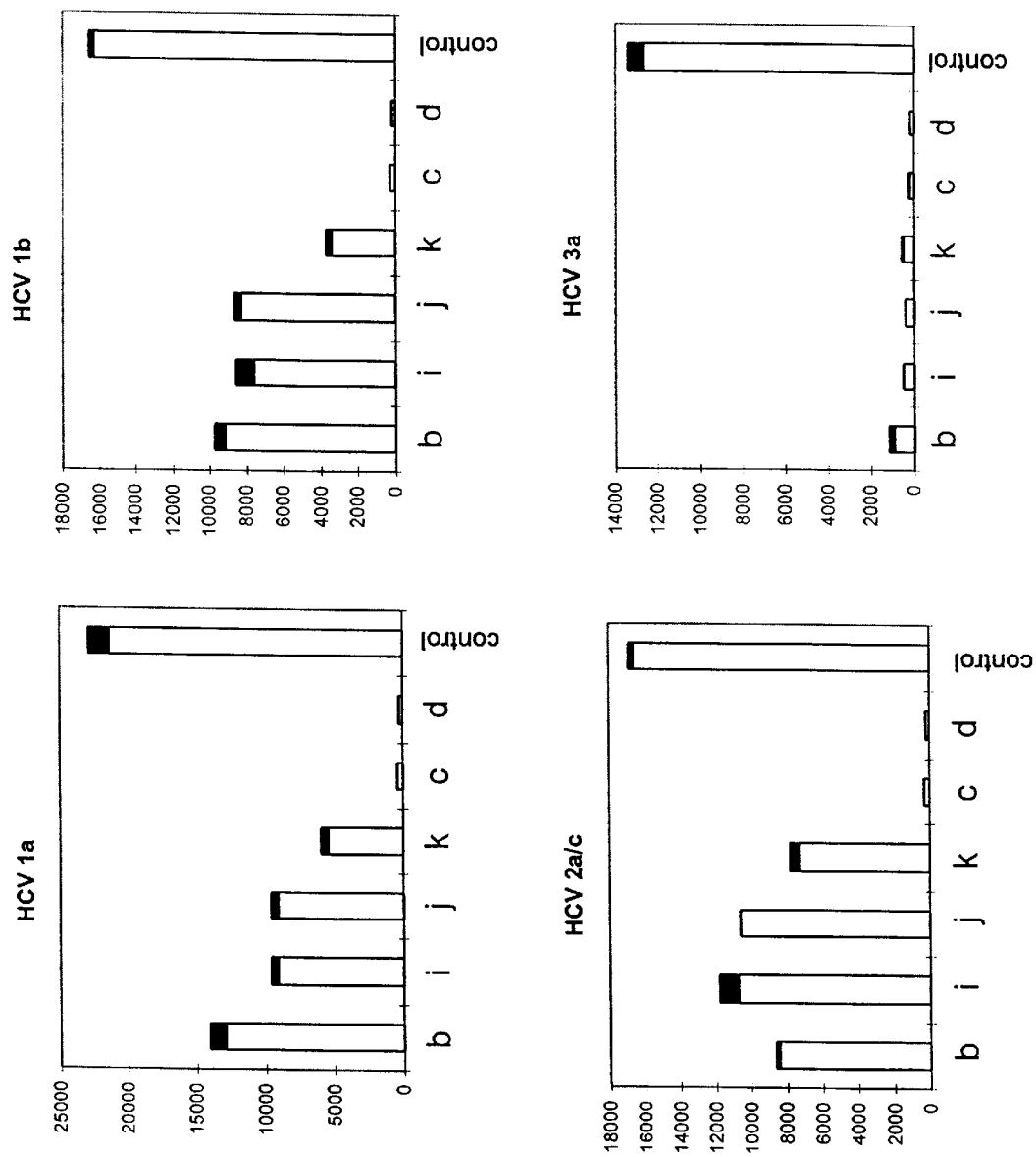

The 244 bp target DNAs were created by PCR and isolated as described in Example 3 (SEQ ID NOS:26–29 for types 1a, 1b, 2c and 3a, respectively). Each of the these probes was tested for binding to the of the HCV amplicons (as shown schematically in FIGS. 18A–18D), as described in Example 6. Each assay was performed in duplicate and the standard deviation is represented by the black bar at the top of each column in FIG. 19. The fluorescence intensity is indicated in arbitrary fluorescence units, shown on the left side of each chart panel. The probe included in each capture reaction are indicated below each graph column. A control probe not shown in the schematic diagram (49-3; 5' Fl -GCGAAAGGCCTTGTGG; SEQ ID NO:66) that hybridizes to all HCV variants was used with each target to verify the presence and amount of DNA in each reaction. The rightmost column in each panel shows the signal from the control reaction.

These data show that functional bridge oligonucleotides may be designed with different intervening sequences, or without any intervening sequence at all ("k"; SEQ ID NO:56), although those having extra nucleotides showed greater signal in most tests. The low signal seen when a mismatch is included on either side verifies that both contact sequences participate in the binding. It is interesting to note that the signal from oligonucleotide "i" (SEQ ID NO:54) is greater than "b" (SEQ ID NO:53) in the type 2a/c test. Examination of this junction in FIG. 18C shows that this type has a C to T change relative to the type 1a, a T that may interact with one of the A residues in the intervening sequence of the "i" probe (SEQ ID NO:54), thereby strengthening the interaction. It can be seen here and in later Examples, that this bridging design does not interact well with the type 3a amplicon, suggesting that this may not be a favored conformation for this particular variant. Nonetheless, these data demonstrate the flexibility available to the user in designing suitable bridging probes.

EXAMPLE 9

Primer Extension of Bridging Oligonucleotides

Figure 20B:
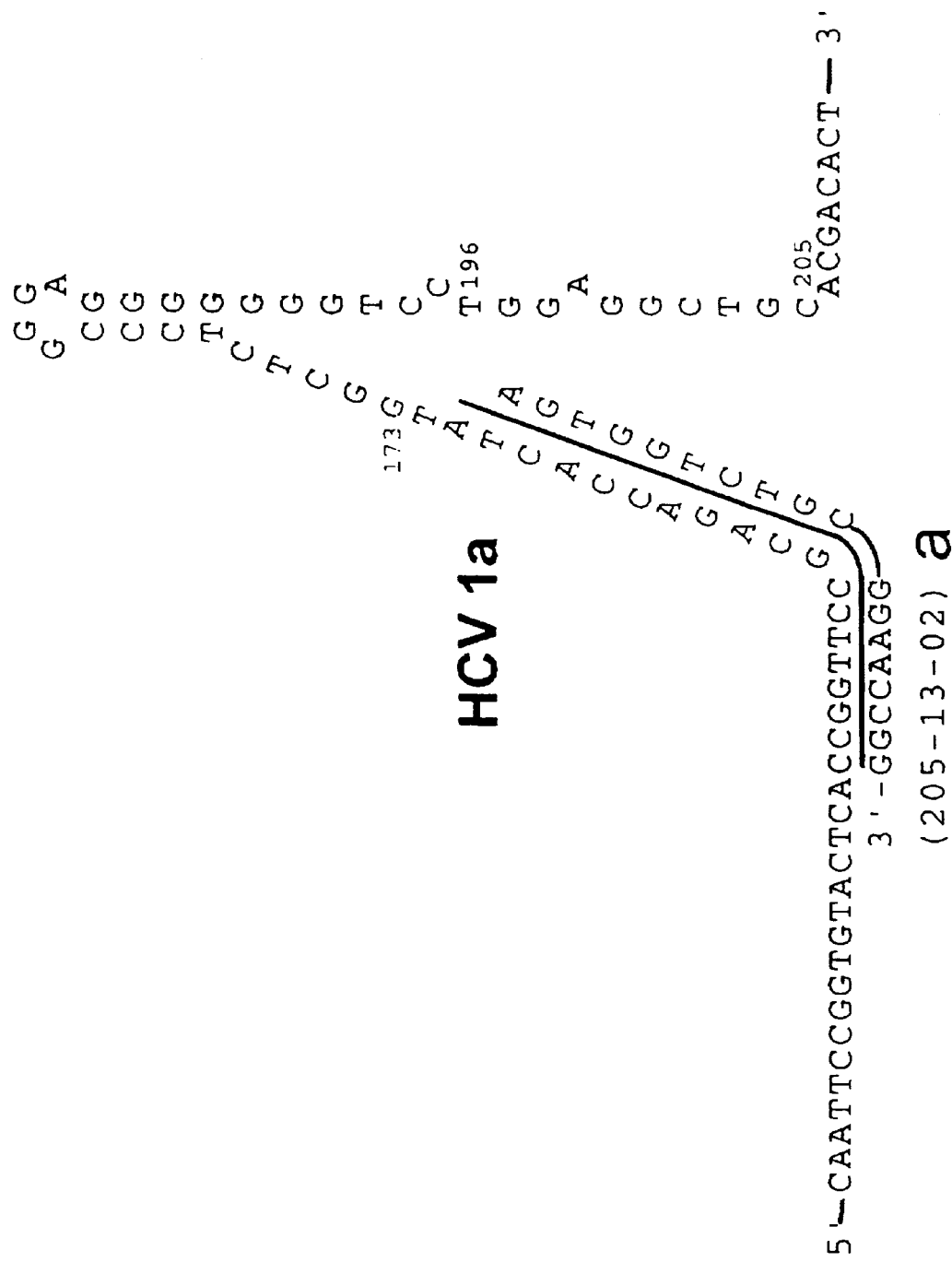
FIG. 20B shows a schematic diagram of a structure in the amplicon derived from HCV type 1a as it might be expected to pair with the fully complementary non-bridging oligonucleotide "a" (SEQ ID NO:52). The regions that are complementary as aligned to the target are indicated by a black line between the strands.

The folding of the 244 bp DNA copy of a segment of the hepatitis C viral genome is described above. The bridging oligonucleotides designed to hybridize across the deduced structures were used in a primer extension reaction to show that the presence of folded structures within the target would not prevent extension of the probe by a template-dependent DNA polymerase. The 244 bp target DNAs were created by PCR and isolated as described in Example 3 (SEQ ID NOS:26–29 for types 1a, 1b, 2c and 3a, respectively). The bridging primers (a, b, c, d, and e, SEQ ID NOS:52, 53, 57, 58, and 59, respectively) are shown in FIG. 20A as they would be expected to hybridize to a folded structure of the HCV type 1a amplicon. The oligonucleotide indicated as "a" (SEQ ID NO:52), while it may have some complementarity that suggest it may serve as a bridge in some conditions, was designed as a non-bridging primer, intended to fully-hybridize to a non-folded target. This is shown schematically in FIG. 20B.

Each primer extension reaction contained either 50 fmole of the 244 bp target DNA or 10 ng of human genomic DNA (Novagen #69237-1, Madison, Wisc.), 1 pmole of the fluorescein-labeled bridge oligonucleotide, 5 units of Klen-Taq polymerase (Ab Peptides), and 0.1 mM of each dNTP in 10 µl of 1×PCR Buffer containing $Mg^{++}$ (Boehringer Mannheim). The assembled reaction mixtures with all the components were heated to 95° C. for 2 minutes, then cooled to the 40° C. for 1 hour. The reactions were terminated by the addition of 5 µl of 95% formamide with 10 mM EDTA and 0.02% Methyl Violet. The samples were then heated at 90° C. for 1 minute, and aliquots were resolved by electrophoresis through 10% denaturing polyacrylamide (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the panel of FIG. 21.

The target DNAs and the bridging primer/probe used in each reaction are indicated. The product of primer extension is indicated by an arrow on the left of the panel as a 170 bp band. It can be seen from these data that the "b" bridging oligonucleotide (SEQ ID NO:53) is able to prime synthesis on the folded HCV target of from all viral types, generating essentially the same level of signal as the non-bridging "a" primer (SEQ ID NO:52). Examination of the first (left most) lane, in which human genomic DNA was used in place of the HCV target shows little or no non specific priming, demonstrating the specificity of the primers for the HCV folded sequence. When single base mismatches are introduced on either side of the bridge (as in "c" and "d" primers; SEQ ID NOS:57 and 58, respectively) the signal is dramatically reduced. When only the 3' portion of the bridging primer is provided ("e"; SEQ ID NO:59) the extension is also nearly non-existent. These data demonstrate: a) that both complementary portions of these bridging oligonucleotides are required for the primers extension, demonstrating that the oligonucleotide is truly bridging; and b) that bridging oligonucleotides with no more than eight contiguous nucleotides of complementarity in single region can be used to specifically recognize an HCV viral sequence by use of its folded structure.

Figure 22:
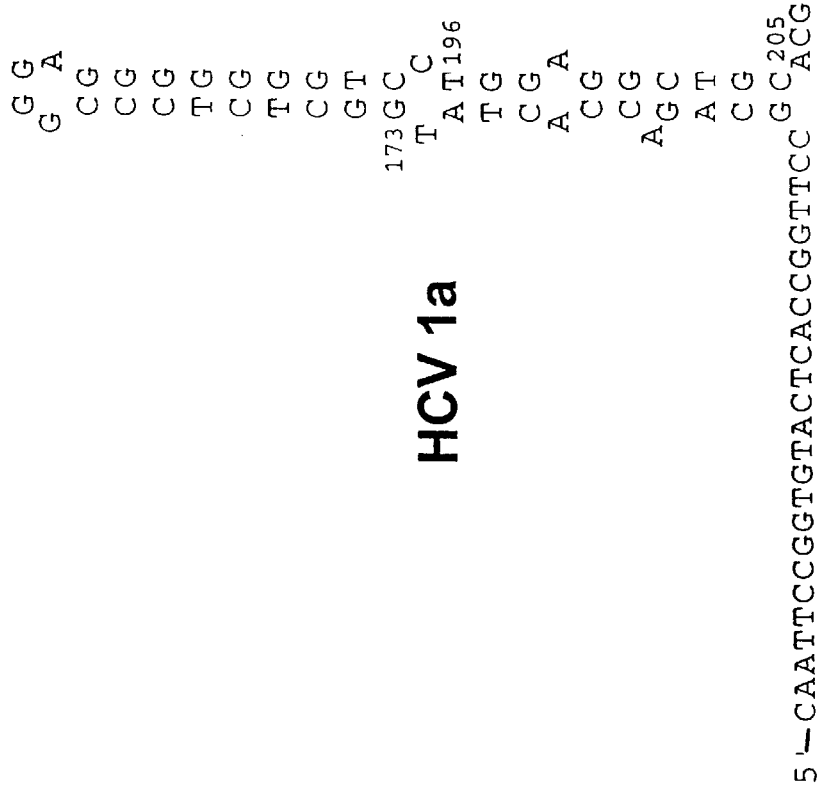
FIG. 22 shows a schematic diagram of a structure in the amplicon derived from HCV type 1a aligned with non-bridging probes "a" and "e" and bridging probe "b" (SEQ ID NOS:52, 53, and 59, respectively). The regions that are complementary as aligned to the target are indicated by a black line between the strands.

Above, the performance of a non-bridging oligonucleotide (i.e., an oligonucleotide that hybridizes to a region of contiguous, complementary bases in the target strand), was compared to the performance of the bridging oligonucleotides to assess the effect of the folded target structure on the enzyme activity. However, at elevated temperatures the folded structures may denature, reducing the binding efficiency of the bridging oligonucleotide relative to the non-bridging oligonucleotide. To demonstrate this effect, primer extension experiments were performed at a range of temperatures selected to decrease the presence of such structures as diagrammed in FIG. 22.

Figure 23:
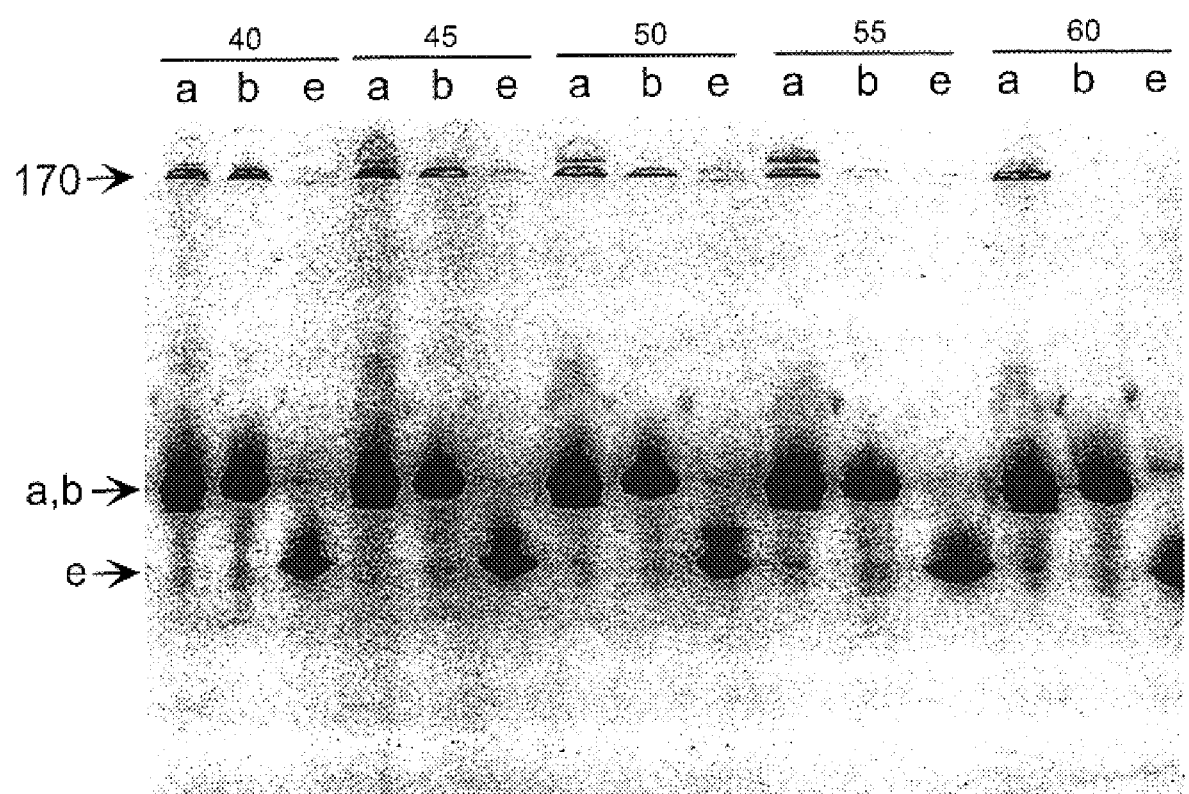
FIG. 23 shows a fluorescence imager scan of the products of primer extension reactions using the probes and target depicted in FIG. 22 in reactions performed over a range of temperatures. The temperatures of each reaction are indicated at the top of the panel, and the unreacted probes are indicated by arrows and their letters on the left. An arrow indicates the 170 nucleotide (nt) product of extension.

For this test, only the bridging, the non bridging and the half primer ("a", "b" and "e"; SEQ ID NOS:52, 53, and 59) were tested. Each primer extension reaction contained 50 fmole of the 244 bp target DNA, 1 pmole of the fluorescein-labeled bridge oligonucleotide, 5 units of KlenTaq polymerase (Ab Peptides) and 0.1 mM of each dNTP in 10 ml of 1×PCR Buffer containing Mg++ (Boehringer Mannheim). Reaction mixtures with all the components were heated to 95° C. for 2 minutes, then cooled to the various extension temperatures for 1 hour. Reactions were performed at 40° C., 45° C., 50° C., 55° C. and 60° C. The reaction terminated by the addition of 5 ml of 95% formamide with 10 mM EDTA and 0.02% Methyl Violet. The products were heated at 90° C. for 1 minute, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the panel of FIG. 23. The temperatures (° C.) and the primers used for each reaction are indicated above each lane.

The extended products are indicated by an arrow on the left side of the panel as a 170 bp band. It can be seen from these data that the non-bridging oligonucleotide ("a"; SEQ ID NO:52) can prime synthesis at each of the test temperatures. The bridging oligonucleotide ("b"; SEQ ID NO:53), however, loses its ability to prime synthesis as the temperature of the reaction rises. This further demonstrates that the bridging oligonucleotides require the presence of the fold within the target strand. This also shows that the use of target folded structure to either support bridging oligonucleotide binding, or to allow structure-based discrimination of sequences as described in previous examples, is preferably done at lower temperature that those used for non-bridging applications. The precise temperature required to maintain a given structure will vary widely depending on the size and stability of a given structure, but a simple temperature titration such as is shown here will serve to identify optimal reaction conditions.

Figure 34:
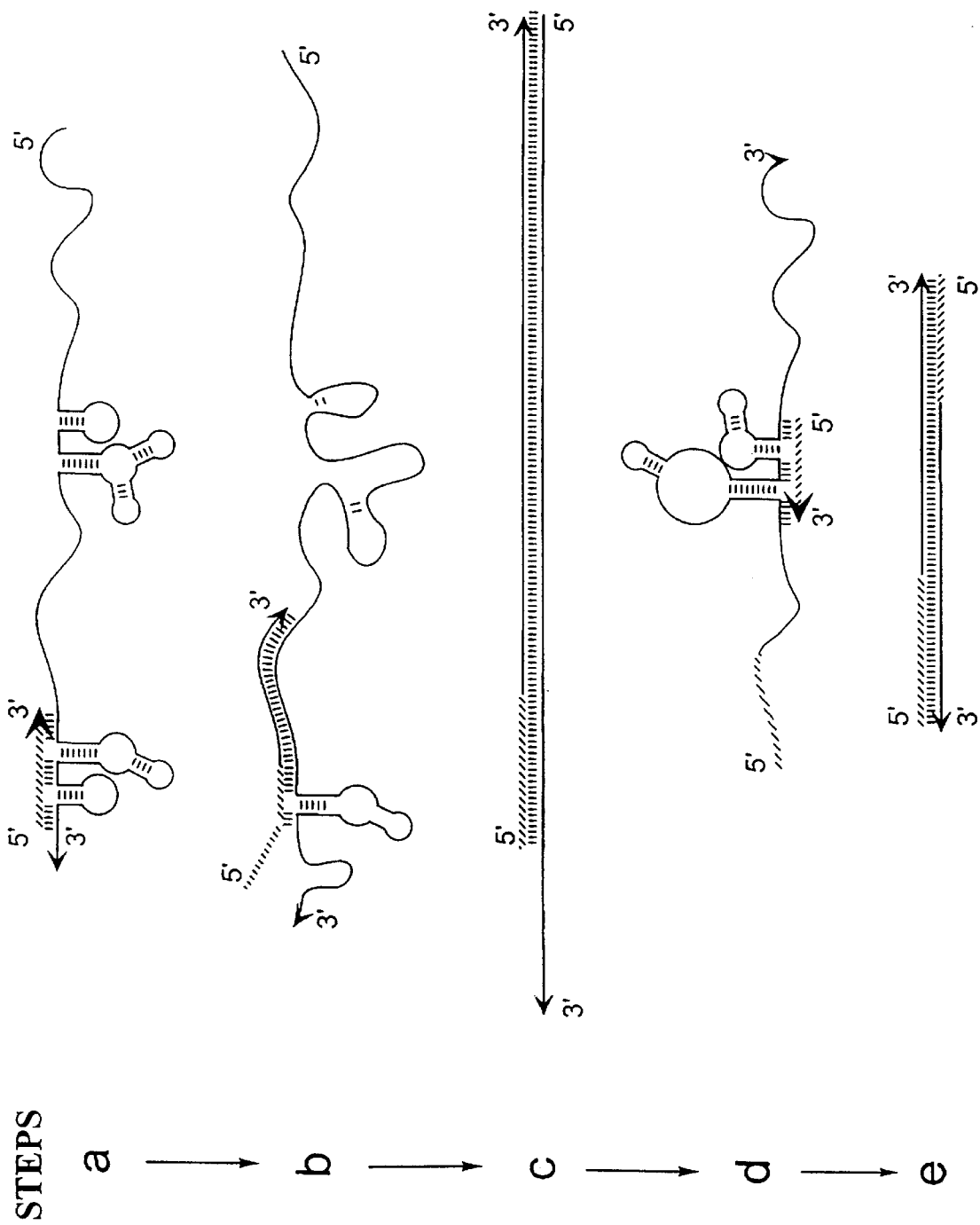
FIG. 34 is a schematic diagram showing one example of the use of bridging oligonucleotides as primers in a polymerase chain reaction. The "a–e" designations in this Figure are used to indicate the general steps in the reaction.

It will be appreciated by those skilled in the art that the target dependent extension of a bridging oligonucleotide can be adapted to the polymerase chain reaction method of target sequence amplification, using standard methods with minimal adaptation. In a PCR, either or both of the primers may be selected to perform the initial target recognition through the specific recognition of non-contiguous sequences. A schematic representation of a reaction in which both primers are thus configured in shown in FIG. 34. This is a simplified version of a PCR diagram that does not show all products at each step; the products shown are selected to demonstrate the manner in which a pair of bridging oligonucleotides may be designed. This example as described is intended as an illustrative example and not as a limitation on the mechanisms of application of the present invention. As shown in 34a, the first strand would be copied from a folded target strand as described above. The bridging oligonucleotide would anneal to the target at low temperature (relative to the temperature at which strand extension takes place). As the temperature of the reaction increases toward a chosen extension temperature (FIG. 34b), the folded structures would be disrupted, but the now partially extended primer would not disassociate due to its increased length. This would allow the polymerase to fully extend the primer, creating a double strand (FIG. 34c). In the next PCR cycle, after the strands have been denatured by heating, and the reaction has again cooled to an appropriate annealing temperature, the newly synthesized strand would likewise assume distinct folded structures, which can serve as binding sites for a second bridging primer (FIG. 34d). When the second primer is fully extended it would fill in the original bridging oligonucleotide with perfectly complementary sequence. In subsequent cycles of the PCR, the former bridge oligonucleotides would now operate as standard, fully complementary oligonucleotides, amplifying the target region between the 3' ends of the original binding sites. The resulting flanking sequences added by the bridge oligonucleotides would be unique to the bridge sequences.

The selection of conditions for using bridging primers in PCR is not dissimilar in reactions designed to use mismatched or degenerate oligonucleotides (Compton, in *PCR Protocols*, Innis et al. (Eds.), [1990], at p. 39). In the first few cycles of PCR it would be desirable to use an annealing temperature that would be permissive of the bridge contact formation. This reaction temperature could be determined empirically for any bridge oligonucleotide by a number of methods known in the art, including direct measurement (e.g., in a temperature controlled spectrophotometer), or by the use of the methods presented here, such as by plate capture, described in numerous examples above, or by temperature titration, as described in this Example. The principles of oligonucleotide design for maximum specificity are also similar to standard practices known in the art. For example, for maximum specificity of PCR oligonucleotides, it is a common practice to skew the stability such that the 5' end of the oligonucleotides has a higher local stability and the 3' end has a lower local stability. Conditions (e.g., sufficiently high annealing temperature), are then selected so that the 3' terminal sequence is unlikely to successfully bind unless the 5' end also binds. This prevents mis-priming caused by unintended hybridization of the 3' terminal residues at non-target sites.

The bridge oligonucleotides can be designed with a similar skew. In addition, it is contemplated that the bridge oligonucleotides be selected such that the 3' end is less stable (e.g., through the use of A/T base pairs or a short contact sequence) so that it is unlikely to find its target site without the successful binding of the other contact sequences, thereby increasing the discriminating power of the bride oligonucleotides in a PCR assay.

EXAMPLE 10

Hybridization Analysis of the Bridge Oligonucleotide in Combination with a Flanking Oligonucleotide Several reactions using involving standard probes require hybridization of two or more oligonucleotides in close proximity. For example, a ligation reactions to join oligonucleotide probes requires that at least two probes hybridize adjacently (i.e., without a gap), on a target or template strand. The Invader ™ reaction requires oligonucleotides to hybridize either adjacently, or with one or more nucleotides of overlap. In both of these scenarios, the binding of adjacent sites on a complementary strand means that resulting individual duplex regions are cooperatively stabilized by the coaxial stacking of the helices. In other words, each duplex will be more stable, i.e., will have a higher apparent melting temperature, in the presence of the other than it would in isolation. In the hybridization-based discrimination of genotypes based on the stability of folded target structure, the increased stability of binding of the bridge probe may reduce the ability to discriminate, absent compensating changes in the design of the probe.

Figure 24:
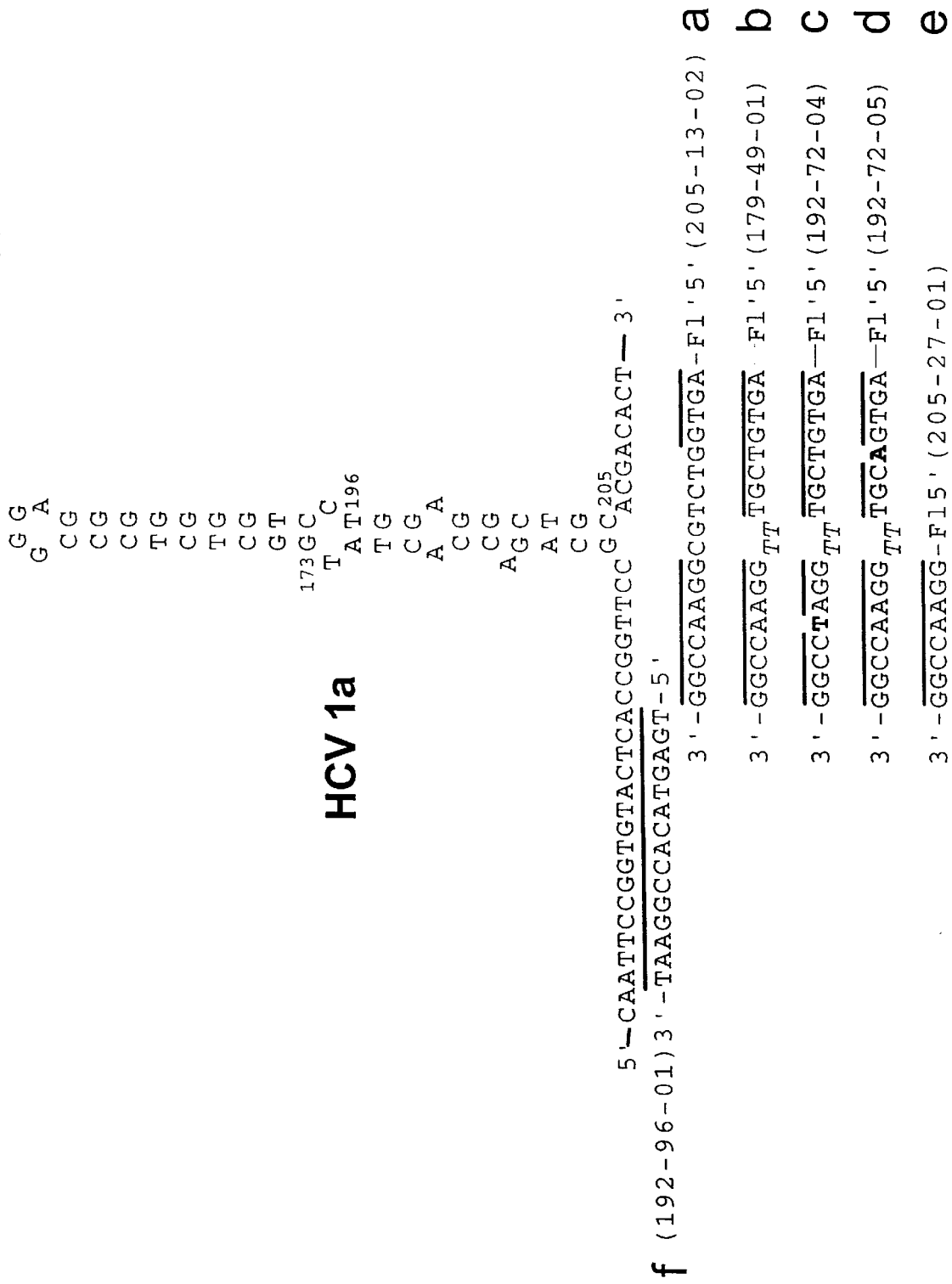
FIG. 24 shows a schematic diagram of a structure in the amplicon derived from HCV type 1a aligned with non-bridging probes "a" and "e" and bridging probes "b"–"d" and ligation oligonucleotide "f" (SEQ ID NOS:52, 59, 53, 57, 58, and 62, respectively). The regions that are complementary as aligned to the target are indicated by a black line between the strands.

To examine the effect of a neighboring oligonucleotide, hybridization capture tests were used on the bridging oligonucleotides and neighbor oligonucleotides designed for the ligation assay. The oligonucleotides were tested either alone, or in the pairs as they would be used in the enzymatic assays. For these tests the capture probes (SEQ ID NOS:52, 53, 60, and 66) were synthetically labeled with fluorescein at their 5' end and purified by gel electrophoresis. These probes are among those shown schematically in FIG. 24, identified by lower case letter. The HCV target DNA was amplified by PCR as described in Example 3, but the 5' end of the antisense strand was labeled with biotin, instead of fluorescein. The primers employed for the amplification of HCV target DNAs were: 5' primer: 5'-B-CTCGCAAGCACCCTATCA (SEQ ID NO:24)—and 3' primer: 5'-GCAGAAAGCGTCTAGCCATGG (SEQ ID NO:25). The PCR reactions were performed as described in Example 3, and the resulting 244 bp PCR products (SEQ ID NOS:20–23) for types 1a, 1b, 2c and 3a, respectively) were purified using "High Pure PCR Product Purification Kit" (Boehringer Mannheim) and eluted in dH$_2$O according to the manufacturer's instructions. The same amount of DNA was used for each sample in the capture assay.

Figure 25:
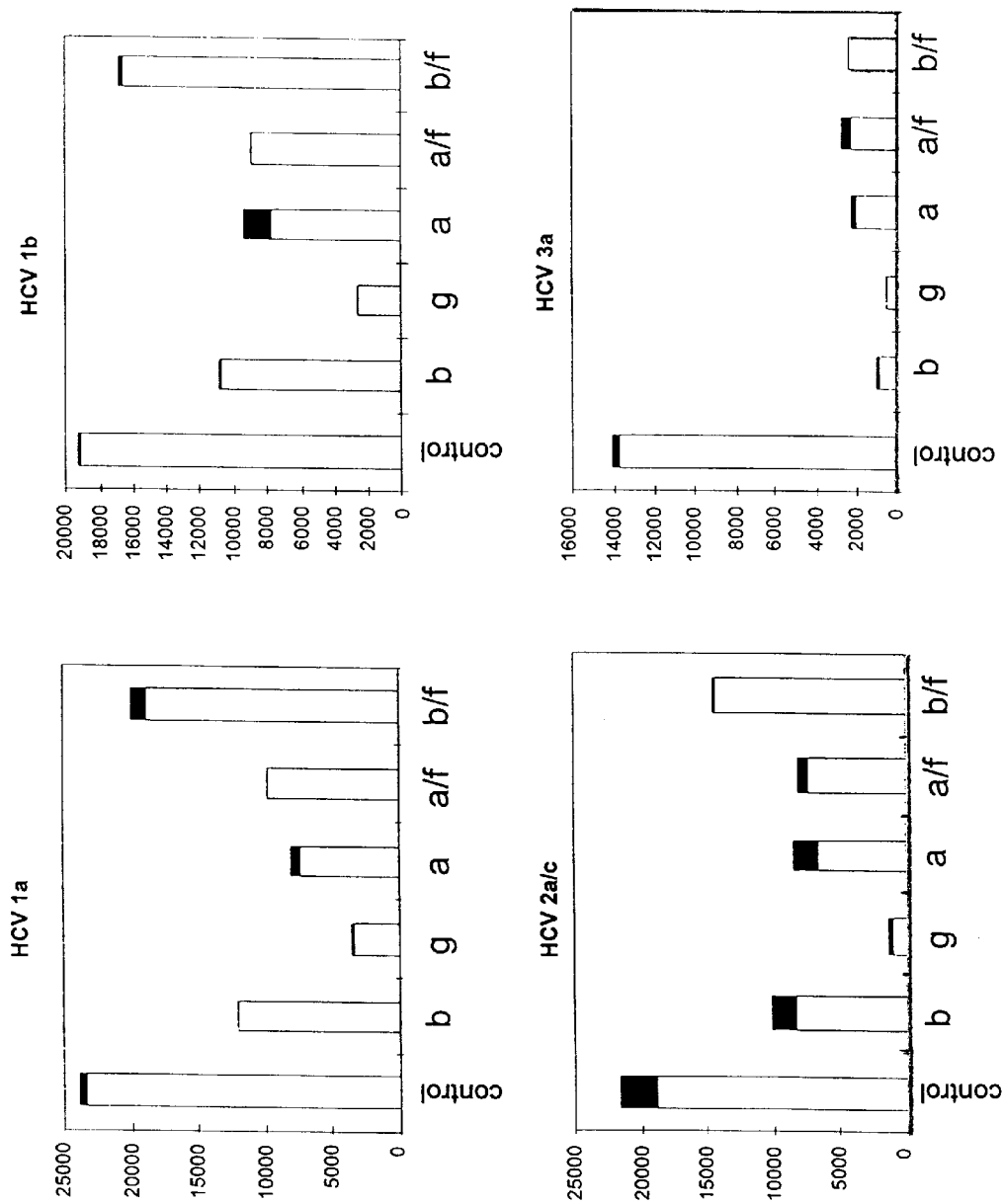
FIGS. 25 shows graphs depicting the fluorescence signal measured after the solid support capture of the amplicons derived from HCV types 1a, 1b, 2a/c and 3a by the indicated probes and combinations of probes. The letters identifying the probes used in each capture test are indicated below each bar, and the signal in arbitrary fluorescence units is shown on the left of each panel.

The hybridization analyses were similar to these described in previous examples. For each test, a hybridization mixture was assembled containing 20 fmoles of heat-denatured, 244 bp HCV PCR product, 1 pmole each of the fluorescein-labeled bridge oligonucleotides and the ligation oligonucleotide probe depicted in FIG. 24 ("b," "a," and "f", SEQ ID NO:53, 52, and 62, respectively), and 10 mg/ml tRNA, in 100 µl of a solution of 0.2% acetylated BSA, 4.5×SSPE. After incubating the mixture at room temperature for 30 min., the mixtures were transferred into wells of a streptavidin-coated 96-well plate (Boehringer Mannheim) and incubated at room temperature for 30 min. The plate was then washed three times with 1×PBS, with 0.01% Tween®-20 non-ionic detergent, containing 0.2% I-Block (Tropix, Bedford, Mass.). A 1:5000 dilution of 0.75 u/ml anti-fluorescein antibody conjugated with alkaline-phosphatase in 0.2% I-block buffer was added to each well. After 20 min at room temperature, the plate was washed three times with TBS (25 mM Tris-Cl, 0.15 M NaCl, pH 7.2). One hundred microliters of Attophos® fluorescent substrate (JBL) was added to each well and the plate was incubated at room temperature for 1 hour before fluorescence readings were taken using a Perkin-Elmer Cytofluor-4000 set to excite at 450/50 nm and to and detect emission at 580/50 nm. Each assay was performed in duplicate, and the standard deviation is represented by the black bar at the top of each column in FIG. 25. In this Figure, the fluorescence intensity is indicated in arbitrary fluorescence units, shown on the left side of each chart panel. The probes included in each capture reaction are indicated below each graph column. A control probe not shown in the schematic diagram ("49-3"; 5' Fl-GCGAAAGGCCTTGTGG; SEQ ID NO:66) that hybridizes to all HCV variants was used with each target to verify the presence and amount of DNA in each reaction. The leftmost column in each panel shows the signal from the control reaction.

In addition, a comparison of bridging and non-bridging oligonucleotides for HCV capture was conducted. It can be seen by comparing the signals from the "a" (non-bridging) and "b" probes (SEQ ID NO:52 and 53, respectively), that the bridge oligonucleotide, having only 8 nts of uninterrupted complementarity to the target, binds to the targets with nearly the same affinity as the 18 nt, fully complementary oligonucleotide, demonstrating the efficacy of the bridge design. Each of the oligonucleotides binds most strongly to HCV type 1a, slightly less efficiently to types 1b and 2a/c, and not very strongly to type 3a. The degree to which this differential binding is out of proportion to variations seen with the control oligonucleotide, particularly evident with type 3a, further illustrated the ability of these probes to differentiate types based on folding of the target nucleic acid.

Figure 29A:
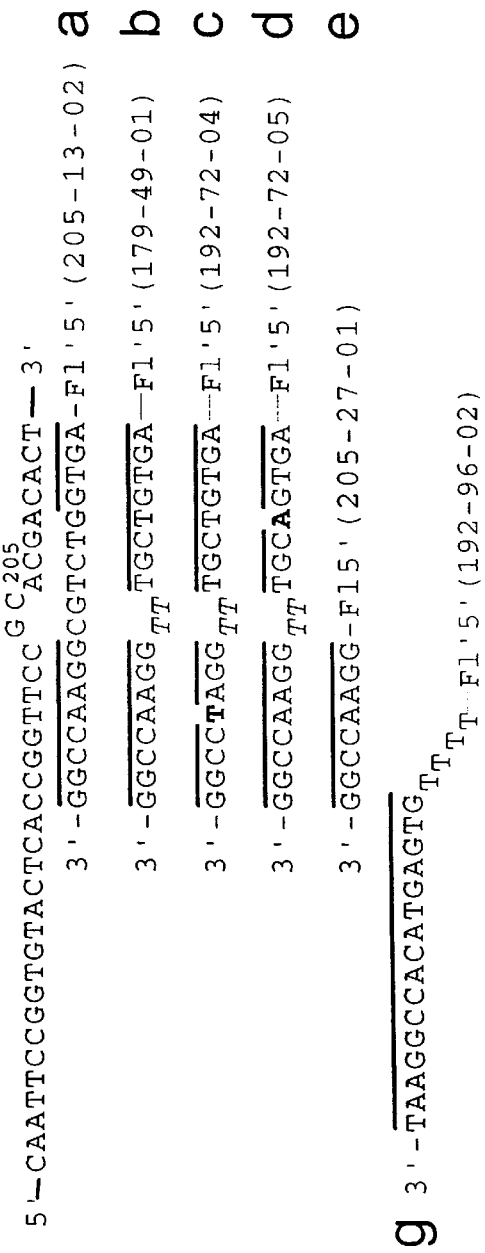

Effect of a neighboring oligonucleotide on the bridge binding signal. The Probe "g" (SEQ ID NO:60), a probe used in an Invader ™ cleavage assay and diagrammed in FIG. 29, was included because it has the same target-complementary sequence as the "f" probe (SEQ ID NO:62), but it also has a 5' fluorescein label to allow it to serve as a capture probe, whereas "f" does not, because it is intended for ligation. The "g" probe (SEQ ID NO:60) also comprises a short 5' tail of 4 T residues that are not included in "f" (SEQ ID NO:62). While not identical in composition, the capture signal from "g" (SEQ ID NO:60) should be a good indicator of the strength of the interaction between the HCV targets and the "f" (SEQ ID NO:62) oligonucleotide. The base signal from each of the capture oligonucleotides (columns marked underneath as "b" and "a"), and the effect of the addition of a neighboring oligonucleotide can be seen by examining the signal in reactions that included the ligation probe "f" (SEQ ID NO:62). It can be seen by comparing "a" to "a/f" that the presence of the second oligonucleotide has little or no effect on the capture of these HCV targets with the non-bridging "a" probe (SEQ ID NO:52). In contrast, in all cases the addition of the "f" oligonucleotide (SEQ ID NO:62) substantially increases the binding by the bridging "b" (SEQ ID NO:53) oligonucleotide. Because "f" (SEQ ID NO:62) is unlabeled and does not contribute to either the plate binding or the signal generation, the additional signal seen in these columns must come from increased binding of "b" (SEQ ID NO:53). This increased stability of binding using a flanking oligonucleotide may be used to enhance the performance of the bridge oligonucleotides in capturing all types of a target. Conversely, the increased stability must be considered in the design of the bridge oligonucleotides only if the goal is to create a system that is maximally sensitive to subtle structural changes, as described in Example 7. When maximum discrimination is desired in an assay that requires the binding of an adjacent oligonucleotide, it may be desirable to shorten or otherwise reduce the stability of the contact segment of the bridge that is nearest to the neighboring oligonucleotide. Common methods of reducing oligonucleotide binding affinity , such as through the use of base analogs or mismatches are well known in the art.

EXAMPLE 11

Target Dependent Ligation of a Bridging Oligonucleotide to an Adjacent Oligonucleotide.

To examine the mismatch effect on the ligation between a bridging oligonucleotide and the ligation oligonucleotides, a linear (i.e., non-folded) oligonucleotide target having appropriately oriented regions of complementarity was synthesized for use as a control target (SEQ ID NO:63)(i.e., to examine the effect of ligation in the presence of a stem). This control target aligned with the ligation and bridging oligonucleotides is depicted in FIG. 26. The PCR conditions to prepare 244 bp ds HCV target DNA were the same as described above.

Figure 27:
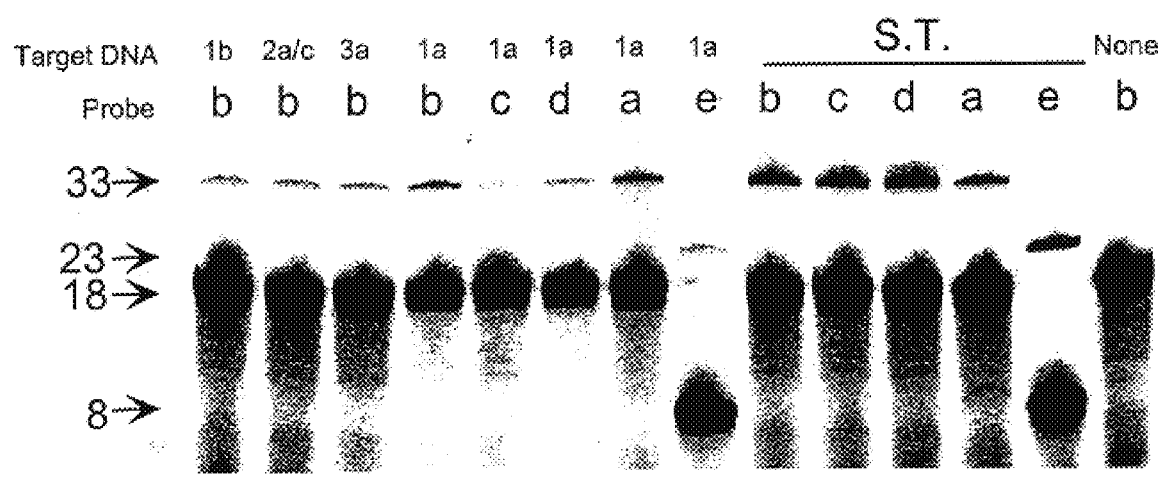
FIG. 27 shows a fluorescence imager scan of the products of ligation reactions using the probes and targets depicted in FIGS. 24 and 26. The unreacted probes are indicated at 8 and 18 nt by arrows on the left. Arrows indicates the 33 nt product of ligation between the probe "f" and "a", "b", "c" or "d", and the 23 nt product of ligation between "f" and "e".

Each ligation reaction contained 200 fmole of the target DNA, 1 pmole each of the bridging and ligation oligonucleotides, 100 units of Ampli-ligase® (Epicenter) in 10 μl of 1×Ampli-ligase® buffer (Epicenter). A control reaction was performed without target DNA. Reactions were assembled with all components except the enzyme and the enzyme buffer, heated to 95° C. for 3 minutes, then cooled to the reaction temperature of 45° C. The ligation reactions were started with the addition of the enzyme and the enzyme buffer, and incubated for 1 hour. The reactions were terminated by the addition of 4 ml of 95% formamide with 10 mM EDTA and 0.02% Methyl Violet. The products were heated at 90° C. for 1 minute, and aliquots were resolved by electrophoresis through 15% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the panel of FIG. 27. The sizes in nucleotides of each band is indicated on the left side of the panel.

The labeled, unreacted probes are visible as either an 18 nt band (a–d; i.e., probes corresponding to SEQ ID NOS:52, 53, 57, and 58) or an 8 nt band (e; i.e., probe corresponding to SEQ ID NO:59). The product of ligation between oligonucleotide "f" (SEQ ID NO:62) and bridge probes "a" through "c" (SEQ ID NOS:52, 53, and 57, respectively), is visible as a 33 nt band near the top of the panel, while the product of ligation between "f" (SEQ ID NO:62) and "e" (SEQ ID NO:59) is indicated as a 23 nt band. It can be seen from these data that all of the bridge oligonucleotides are able to use the folded target at a template to correctly align for ligation. The efficiency of the ligation can be assessed by comparing the product intensity in each lane to the intensity from ligation of the non-bridging oligonucleotide "a" (SEQ ID NO:52). Probe "b" (SEQ ID NO:53), which is fully complementary in both contact sequences shows the strongest signal on the HCV type 1a, which is consistent with the binding seen in the capture tests of these oligonucleotides. The ligation of the shortest oligonucleotide, "e" (SEQ ID NO:59) shows that even an 8 nt probe is sufficiently stable in this assay to be ligated at some level. The least amount of ligation is seen with the bridge probe having the mismatch closest to the site of ligation, reflecting a decrease in hybridization for this portion of the oligonucleotide or a decrease in activity of the ligase enzyme near a mismatch, or a combination of these effects.

As described above for the primer extension of the bridging oligonucleotide, at elevated ligation temperatures the folded structures denature, reducing the binding efficiency of the bridging oligonucleotide relative to the non-bridging oligonucleotide. To examine this effect in a ligation reaction, and to examine the effect of the folding on the discrimination of the amplicons by HCV type, additional experiments were performed on all four amplicon types, at a range of temperatures. Because the thermostable ligase activity intended for use under high-stringency conditions (e.g., at temperatures above about 45° C.), T4 DNA ligase, commonly used at 10 to 30° C., was used in the ligations performed at lower temperature.

Figure 28:
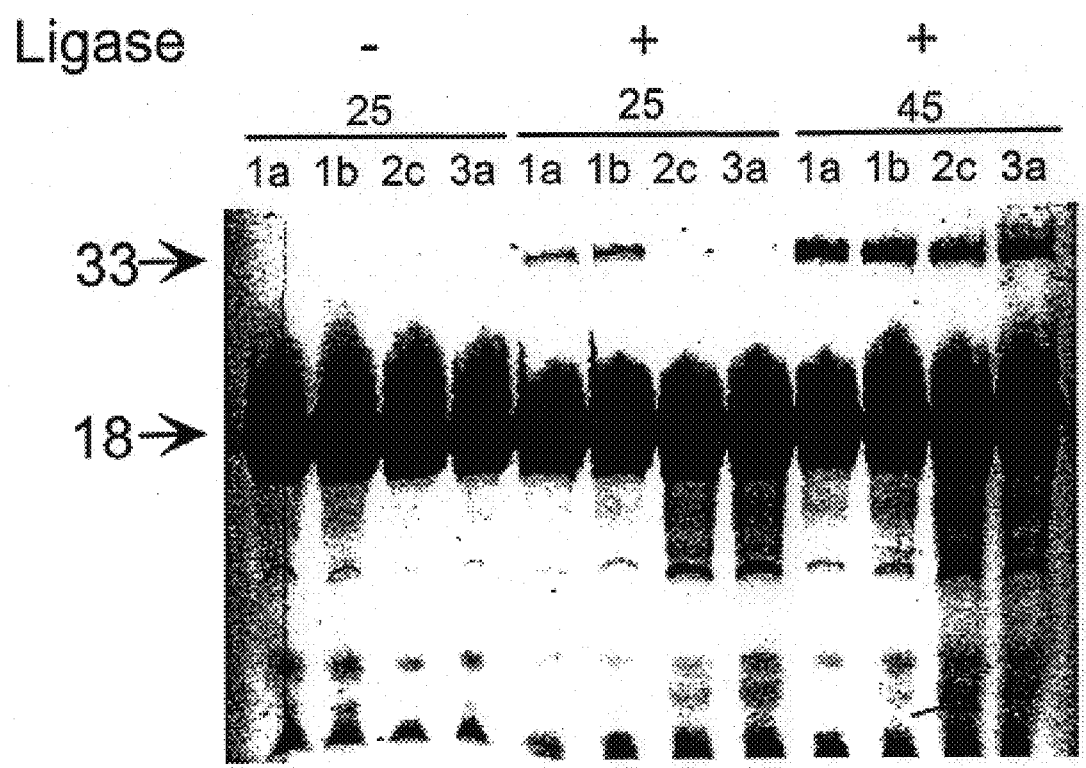
FIG. 28 shows a fluorescence imager scan of the products of ligation reactions using the ligation probe "f" and the bridging probe "b" in reactions performed at various temperatures, using target amplicons derived from HCV types 1a, 1b, 2a/c and 3a. Arrows on the left indicate the unreacted probe at 18 nt the product of ligation at 33 nt.

Each ligation reaction contained 200 fmole of the target DNA, 1 pmole of the fluorescein-labeled bridge oligonucleotide, 1 pmole of the ligation oligonucleotide and 3 units of T4 Ligase (Promega) in 10 μl of 1×T4 Ligase® buffer (Promega). Reactions were assembled with all components except the enzyme and the concentrated enzyme buffer, heated to 95° C. for 3 minutes, then cooled to the reaction temperature of either 25° C. or 45° C. The ligation reactions were started by the addition of the enzyme and the concentrated buffer to bring each of those components to the final concentrations listed above, and incubated for 1 hour. The reactions were terminated by the addition of 4 μl of 95% formamide with 10 mM EDTA and 0.02% Methyl Violet. The products were heated at 90° C. for 1 minute, and aliquots were resolved by electrophoresis through 15% denaturing polyacrylamide (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the panel of FIG. 28. The reaction temperatures are indicated at the top of the panel, and the control reactions lacking the ligase enzyme are indicated. The labeled, unreacted probes are visible as an 18 nt band . The product of ligation is visible as a 33 nt band near the top of the panel.

Examination of the product bands at the two temperatures confirms the expected increase in discrimination at the lower temperature. The signals from the 1a and 1b types are very similar, while the signals from 2a/c and 3a are much lower. While the 3a result is consistent with the capture data using the combination of the "b" and "f" probes (SEQ ID NO:53 and 62, respectively) shown in FIG. 25, the signal from 2a/c is relatively lower than in the capture. Without limitation to any particular mechanism, this effect may be attributable to the substrate specificity of the ligase at this temperature (e.g., the assumed structure may have a loop or bulge situated in a manner that inhibits the enzyme). Nonetheless, this example demonstrates that these viral types may be distinguished using ligation reactions performed under non-stringent conditions. At slightly elevated temperature, the product bands are of approximately equal, and stronger intensity. The uniformity of the signal may be attributed to the partial or complete disruption of the structure at this temperature. It was observed in the FIG. 27 that even the 8 nt "e" (SEQ ID NO:59) control molecule could be efficiently ligated to the "f" ligation oligonucleotide (SEQ ID NO:62) on the linear synthetic target ("S.T."; SEQ ID NO:63). This indicates that the ligase can join rather short oligonucleotides, even at temperatures above their estimated Tm. As the structure is unfolded in the 45° C. reaction in FIG. 28, the bridging oligonucleotide may be participating in the ligation in this manner (i.e., only its 3' end is binding), eliminating the ability to discriminate between types under these conditions. The strength of the signal may reflect increased activity of the enzyme at this temperature, the preference for the enzyme for this structure over the bridge conformation, or a combination of these or other factors.

The ligation under the lower temperature conditions demonstrates that bridging oligonucleotides can be used to identify folded target molecules in this type of a reaction. Since the contact sequence on the 3' terminus of the bridging oligonucleotides of these examples is clearly stabilized in these reactions (i.e., a mismatch in this portion, as in oligonucleotide "c" (SEQ ID NO:57), has less effect on the bridge activity of the probe than in the capture, primer extension and cleavage assays shown in other examples) it may be desirable to provide a less stable contact sequence in this region. Means for reducing oligonucleotide Tm are well known in the art, and a few methods are discussed above, in the context of PCR primer design.

Figure 35:
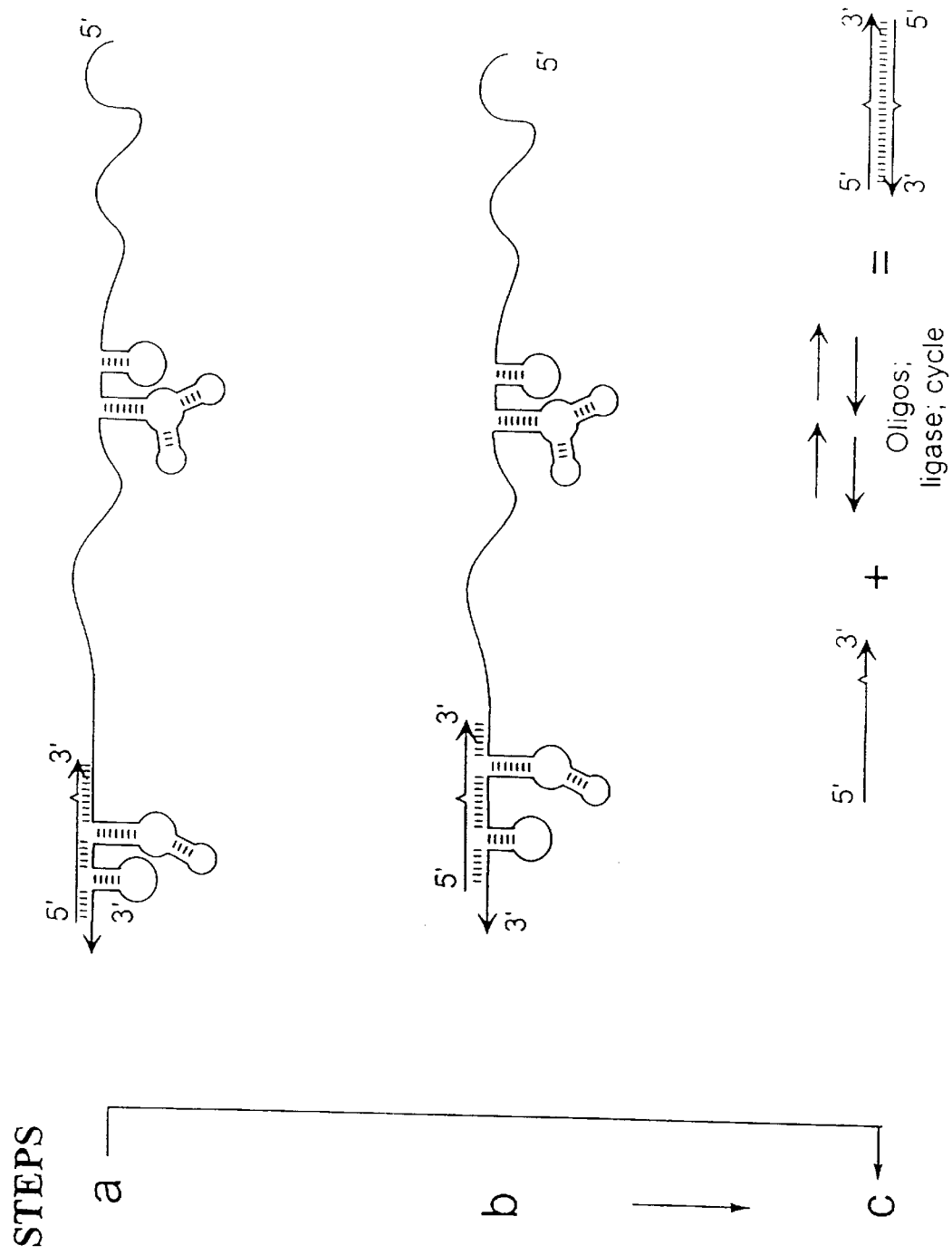
FIG. 35 is a schematic diagram showing two examples of target-dependent ligation of bridging oligonucleotides, with subsequent detection of the bridged ligation product by a ligase chain reaction. The "a–c" designations in this Figure are used to indicate the steps in the reaction, with either step a or b being followed by step c (i.e., b does not follow a in the progression of the steps).

Just as the conditions for bridge oligonucleotide primer extension can be adapted to the polymerase chain reaction for amplification of signal, the ligation of the bridge oligonucleotides can be adapted to the ligase chain reaction. The target-specific ligation event can be viewed as creating a unique molecule to be detected, even if the ligation point in not centered, as it is in the LCR. Two possible configurations are depicted schematically in FIG. 35. In all panels of this Figure, the ligation junction is represented by a carat point on the ligated nucleic acid. In the first panel, FIG. 35a, the bridging oligonucleotide would be extended by addition of a short sequence, such as a hexamer or an octamer. Ligation of short oligonucleotides that are stabilized by coaxial stacking is known in the art (Kaczorowski and Szybalski, Gene 179:189 [1996]), and is demonstrated by ligation of the "e" oligonucleotides (SEQ ID NO:59) shown in FIG. 27. The configuration shown in 35b instead shows the ligation of two longer probes, each of which bridges in a structure. It is contemplated that other configurations within the scope of the present invention would be apparent to those skilled in the art, including but not limited to ligation of a non-bridging oligonucleotide to the 5' end of a bridging oligonucleotide, or ligation of more that two oligonucleotides assembled on a single folded target.

In each of the embodiments and configurations listed above, the ligation event would create a unique contiguous sequence not found in the target nucleic acid. This unique sequence may then itself be detected by a number of means, including, but not limited to the ligase chain reaction. Practice of the ligase chain reaction for the detection of specific sequences is well known in the art, and the means of adapting the bridging ligation to this amplification method are easily ascertainable from the literature (See e.g., Barany, PCR Meth. App. 1:5 [1991], and U.S. Pat. No. 5,494,810, herein incorporated by reference). The bridging oligonucleotides may also be used in modified LCR assays, such as gap-filling LCR (See e.g., U.S. Pat. No. 5,427,930, herein incorporated by reference), or other variants of the method. By combining the bridging oligonucleotides of the present invention with the ligase chain reaction an investigator can derive the benefits of structure characterization discussed above, but performed directly on samples of interest, without intervening culture or PCR amplification.

EXAMPLE 12

Target Dependent Cleavage of a Probe, Directed by an Invasive Bridging Oligonucleotide The previous examples demonstrated the ability of the bridging oligonucleotides to serve as substrate in reactions that produced a maximum of one event for each copy of a folded target. There are many applications based on the use of oligonucleotides in which the reactions are configured to produce many signals for each copy of a target nucleic acid. Such reactions include, but are not limited to ligase chain reaction, polymerase chain reaction, cycle sequencing, and nuclease detection assays such as the cycling probe reaction. We show here that such reactions can be configured to make use of noncontiguous probe binding. The use of bridging probes may in some embodiments allow the kind of structure-based typing described above to be used in a reaction that can also amplify the signal from the target. It is also well known that even single-stranded nucleic acid targets can fold such that very little sequence is actually available for probe binding for detection or for antisense applications. The ability of probes to bind to non-contiguous sites facilitates the design of probes that interact only with the outer surface of the target nucleic acid, thus allowing detection or typing of targets that could not previously be characterized by hybridization methods.

Figure 31:
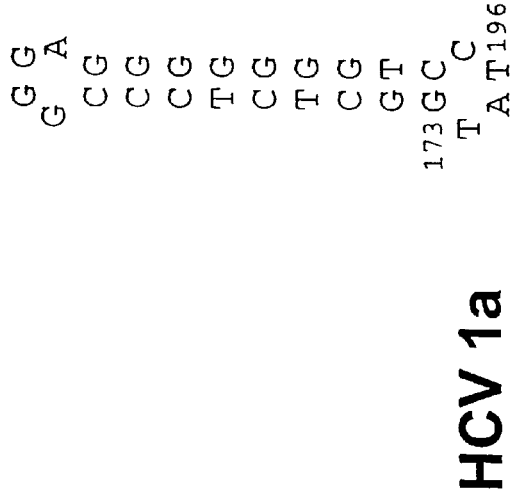
FIG. 31 shows a schematic diagram of a structure in the amplicon derived from HCV type 1a aligned with bridging probe "b" (SEQ ID NO:53) and invasive cleavage probe "h" (SEQ ID NO:61). The regions that are complementary as aligned to the target are indicated by a black line between the strands.

The Invader™ reaction involves the contacting of a target nucleic acid with a pair of oligonucleotides to create a cleavage structure as described above. The signal probes can leave the structure after cleavage, to be replaced by an uncleaved copy, thus starting the cycle again, and allowing each target to create many copies of the cleaved probe during the course of the reaction. The probes and targets used for this assay are diagrammed in FIGS. 29A, 29B and 31. The effects of the signal probe ("g"; SEQ ID NO:60) on the stability of the bridge oligonucleotides was described in Example 9.

In the experiments in this Example, all invasive cleavage reactions included a mixture of 10 fmole of either the 244 bp target DNA or the synthetic linear target, 10 pmole each of a fluorescein-labeled bridge oligonucleotide and the fluorescein-labeled probe ("g" or "h" SEQ ID:60 or 61), 10 mM MOPS, 7.5 mM MgCl2, 20 ng of the 5' nuclease AfuFEN1 (i.e., a FEN1 from *Archaeoglobus fulgidus*, PCT/US97/21783, herein incorporated herein by reference), and water to a fmol volume of 10 μl. Reactions were assembled with all components except the enzyme and 7.5 mM MgCl$_2$, heated to 95° C. for 2 minutes. The reactions were then cooled to the indicated reaction temperatures, started with the addition of enzyme and 7.5 mM MgCl$_2$, and incubated for 1 hour. The reactions were then terminated by the addition of 10 μl of 95% formamide with 10 mM EDTA and 0.02% Methyl Violet. The products were heated at 90° C. for 1 minute, and aliquots were resolved by electrophoresis through 20% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi).

Figure 30:
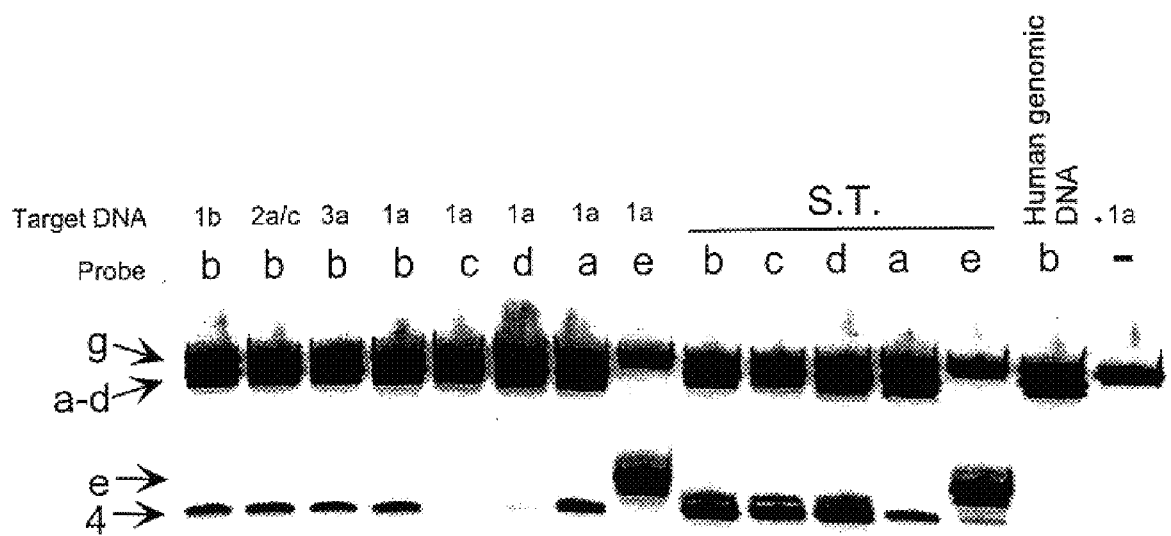
FIG. 30 shows a fluorescence imager scan of the products of invasive cleavage reactions using the probes and targets depicted in FIGS. 29A and 29B. The identities of the target DNA and probes used in each reaction (in addition to the cleavage probe "g"; SEQ ID NO:60) are indicted above each lane, and the unreacted probes are indicated by arrows and their letters on the left. An arrow indicates the 4 nucleotide (nt) product of cleavage.

The first assay tested the ability of both the HCV variants and a synthetic non-folded target to serve as a target in this assay. All reactions used the "g" signal probe (SEQ ID NO:60), and were incubated at 55° C. The resulting image is shown in FIG. 30. The type target DNA and the bridging probe used in each assay are identified above each line. In this Figure, the unreacted probes are indicated with arrows and their letters to the left of the panel, in addition, the 4-nt product of the cleavage is also indicated by arrow.

Examination of the intensity of the 4 nt band in each lane shows that on each type of folded target (1a, 1b, 2a/c and 3a) the bridging probe "b" (SEQ ID NO:53) performed nearly as well as the linear probe "a" (SEQ ID NO:52) at directing cleavage of the signal probe "g" (SEQ ID NO:60). In contrast, the bridging probes either having a mismatch in one contact sequence ("c" and "d"; SEQ ID NOS:57 and 58) or missing one contact sequence ("e"; SEQ ID NO:59) were not able to complete the cleavage structure to any significant extent. This demonstrates not only that a bridging oligonucleotide having no more than 8 bases of contiguous complementarity in any contact sequence can nonetheless specifically detect this HCV sequence, it also shows that both of the contact sequences in the probe are important to this function.

The signal generated from the non-folded synthetic target shown the maximum product yield that can be expected from these probes when essentially perfectly bound. As expected based on previous experiments conducted during the development of the present invention, the signal is stronger, although not astoundingly so. Also as expected based on previous experiments conducted during the development of the present invention, the half molecule, which does not cross a structure on the folded target, does not improve much in performance when the structure is removed, while the non bridging probe performance is decreased because has a number of mismatches to this target (See, FIG. 29B).

Figure 32:
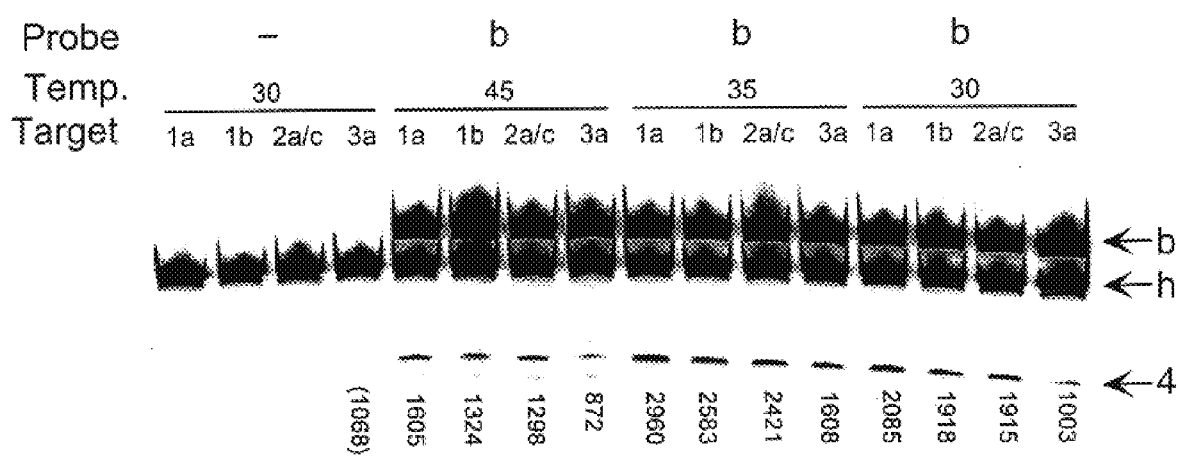
FIG. 32 shows a fluorescence imager scan of the products of invasive cleavage reactions using the probes and target depicted in FIG. 31, in reactions performed over a range of temperatures, as indicated above the lanes. The identities of the target DNA and probes used in each reaction (in addition to the cleavage probe "h"; SEQ ID NO:61) are indicted above each lane, and the unreacted probes are indicated by arrows and their letters on the right. An arrow indicates the 4 nucleotide (nt) product of cleavage.

As described above for the primer extension and ligation of the bridging oligonucleotides, at elevated temperatures the folded structures denature, reducing the binding efficiency of the bridging oligonucleotide relative to the non-bridging oligonucleotide. To examine this effect in an Invader™ reaction, additional experiments were performed at a range of temperatures. Because the Invader™ assay is performed near the Tm of the signal probe to allow turnover without thermal cycling, a shorter probe molecule ("h"; SEQ ID NO:61) was made for use at the lower temperatures. This is shown schematically in FIG. 31. The Invader™ reactions were performed as described above, using the bridging probe "b" (SEQ ID NO:53) and the "h" signal probe (SEQ ID NO:61), with incubations done at 30°, 35° and 40 ° C. All four HCV amplicon types were tested. The resulting image is shown in the panel of FIG. 32. The probes and targets used in each reaction, and the temperatures of the incubation are indicated above the panel. The arrow on the right indicate the unreacted probes by their letters, and the 4 nt cleavage product. The fluorescence, in arbitrary fluorescence units, measured for each of the 4 nt bands is shown below each lane; the same location in a no-probe reaction lane was counted to determine the background level (in parentheses), which was subtracted from the product count for each lane.

Examination of these data show that while the "b" (SEQ ID NO:53) bridge functions in the invasive cleavage at all temperatures, the lower temperature reactions show a greater signal differential between the HCV type 3a lane and the other types. This is consistent with the data from the capture experiments described in Examples 8 and 10, showing that the 3a type amplicon does not have the same structure in this region as the other 3 types tested. This also demonstrates that discrimination of subtle sequence differences by this method is most easily done at temperatures that encourage folding in the target molecules.

Figure 33:
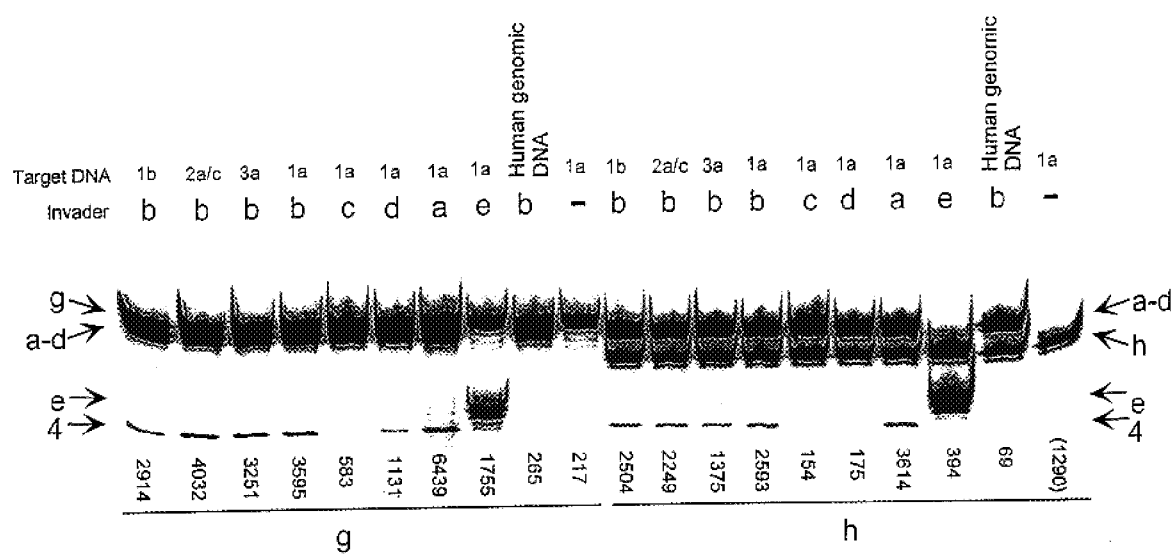
FIG. 33 shows a fluorescence imager scan of the products of invasive cleavage reactions using the probes and targets depicted in 29A and 31. The identities of the target DNA and probes used in each reaction are indicted above each lane, and the cleavage probes used ate indicated below the lanes. The unreacted probes are indicated by arrows and their letters on either side and arrows indicate the 4 nucleotide (nt) product of cleavage.

This is further supported by examination of the reactions data shown in FIG. 33. This panel compares the signals generated at two temperatures, 55° C. and 35° C., using the whole array of bridging and non-bridging probes, on a number of targets. The identities of the target DNAs and probes used in each reaction are indicted above each lane, and the cleavage probes used are indicated below the lanes. The unreacted probes are indicated by arrows and their letters on either side of the panel, and arrows indicate the 4 nucleotide (nt) product of cleavage. The fluorescence, in arbitrary fluorescence units, measured for each of the 4 nt bands is shown below each lane; the same location in a no-probe reaction lane was counted to determine the background level (in parentheses), which was subtracted from the product count for each lane.

The data shown in FIG. 33 shows the same profile of detection signal for the HCV samples as in the previous example, and further demonstrated that the mismatched bridge probes ("c" and "d"; SEQ ID NO:57 and 58) and the half probe ("e"; SEQ ID NO:59) have limited function in this assay. Similarly, the probe is not detectably cleaved when the bridging oligonucleotide is altogether omitted. Furthermore, reactions using human genomic DNA in place of the HCV target exhibit no signal that can be seen above background, demonstrating the specificity of this assay in both "stringent" and "non-stringent" conditions.

It is also clear from the above that the present invention provides methods for the analysis of secondary structure within nucleic acids, without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within genes obtained from various organisms, including humans.

All publications and patents mentioned in the above specification are herein incorporated by reference. Various modifications and variations of the described method and system of the invention will be apparent to those skilled in the art without departing from the scope and spirit of the

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
      (A) LENGTH: 391 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

```
AGCTCGTATG GCACCGGAAC CGGTAAGGAC GCGATCACCA GCGGCATCGA GGTCGTATGG     60

ACGAACACCC CGACGAAATG GGACAACAGT TTCCTCGAGA TCCTGTACGG CTACGAGTGG    120

GAGCTGACGA AGAGCCCTGC TGGCGCTTGG CAATACACCG CCAAGGACGG CGCCGGTGCC    180

GGCACCATCC CGGACCCGTT CGGCGGGCCA GGGCGCTCCC CGACGATGCT GGCCACTGAC    240

CTCTCGCTGC GGGTGGATCC GATCTATGAG CGGATCACGC GTCGCTGGCT GGAACACCCC    300

GAGGAATTGG CCGACGAGTT CGCCAAGGCC TGGTACAAGC TGATCCACCG AGACATGGGT    360

CCCGTTGCGA GATACCTTGG GCCGGTGGTC C                                    391
```

(2) INFORMATION FOR SEQ ID NO:2:

(i) SEQUENCE CHARACTERISTICS:
      (A) LENGTH: 391 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:2:

```
AGCTCGTATG GCACCGGAAC CGGTAAGGAC GCGATCACCA CCGGCATCGA GGTCGTATGG     60

ACGAACACCC CGACGAAATG GGACAACAGT TTCCTCGAGA TCCTGTACGG CTACGAGTGG    120

GAGCTGACGA AGAGCCCTGC TGGCGCTTGG CAATACACCG CCAAGGACGG CGCCGGTGCC    180

GGCACCATCC CGGACCCGTT CGGCGGGCCA GGGCGCTCCC CGACGATGCT GGCCACTGAC    240

CTCTCGCTGC GGGTGGATCC GATCTATGAG CGGATCACGC GTCGCTGGCT GGAACACCCC    300

GAGGAATTGG CCGACGAGTT CGCCAAGGCC TGGTACAAGC TGATCCACCG AGACATGGGT    360

CCCGTTGCGA GATACCTTGG GCCGCTGGTC C                                    391
```

(2) INFORMATION FOR SEQ ID NO:3:

(i) SEQUENCE CHARACTERISTICS:
      (A) LENGTH: 391 base pairs
      (B) TYPE: nucleic acid
      (C) STRANDEDNESS: single
      (D) TOPOLOGY: linear (ii) MOLECULE TYPE: other nucleic acid invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

(A) DESCRIPTION: /desc = "DNA"

(xi) SEQUENCE DESCRIPTION: SEQ ID NO:3:

AGCTCGTATG GCACCGGAAC CGGTAAGGAC GCGATCACCA GCGGCATCGA GGTCGTATGG      60

ACGAACACCC CGACGAAATG GGACAACAGT TTCCTCGAGA TCCTGTACGG CTACGAGTGG     120

GAGCTGACGA AGAGCCCTGC TGGCGCTTGG CAATACACCG CCAAGGACGG CGCCGGTGCC     180

GGCACCATCC CGGACCCGTT CGGCGGGCCA GGGCGCTCCC CGACGATGCT GGCCACTGAC     240

CTCTCGCTGC GGGTGGATCC GATCTATGAG CGGATCACGC GTCGCTGGCT GGAACACCCC     300

GAGGAATTGG CCGACGAGTT CGCCAAGGCC TGGTACAAGC TGATCCACCG AGACATGGGT     360

CCCGTTGCGA GATACCTTGG GCCGCTGGTC C                                    391

(2) INFORMATION FOR SEQ ID NO:4:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

AGCTCGTATG GCACCGGAAC CGGTAAGGAC GCGATCACCA CCGGCATCGA GGTCGTATGG      60

ACGAACACCC CGACGAAATG GGACAACAGT TTCCTCGAGA TCCTGTACGG CTACGAGTGG     120

GAGCTGACGA AGAGCCCTGC TGGCGCTTGG CAATACACCG CCAAGGACGG CGCCGGTGCC     180

GGCACCATCC CGGACCCGTT CGGCGGGCCA GGGCGCTCCC CGACGATGCT GGCCACTGAC     240

CTCTCGCTGC GGGTGGATCC GATCTATGAG CGGATCACGC GTCGCTGGCT GGAACACCCC     300

GAGGAATTGG CCGACGAGTT CGCCAAGGCC TGGTACAAGC TGATCCACCG AGACATGGGT     360

CCCGTTGCGA GATACCTTGG GCCGGTGGTC C                                    391

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

AGCTCGTATG GCACCGGAAC                                                  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

TTGACCTCCC ACCCGACTTG                                                  20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

AGCTCGTATG GCACCGGAAC C                                      21

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

GGACCAGCGG CCCAAGGTAT                                       20

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

GGACCACCGG CCCAAGGTAT CT                                   22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

TTTTTGCCGC TGGTGATCGC G                                      21

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

GGAGAGCCAT AG                                                  12

(2) INFORMATION FOR SEQ ID NO:12:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

TGGTCTGCGG A                                          11

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

GGACGACCGG G                                          11

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

GGAGATTTGG G                                          11

(2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

CCGCGAGACT G                                          11

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

CTAGCCGAGT AG                                         12

(2) INFORMATION FOR SEQ ID NO:17:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

TGTTGGGTCG C                                                            11

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

CCGCGAGACC G                                                            11

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

CCGCAAGACC G                                                            11

(2) INFORMATION FOR SEQ ID NO:20:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

GATTCTGTCT TCACGCAGAA AGCGTCTAGC CATGGCGTTA GTATGAGTGT CGTGCAGCCT        60

CCAGGACCCC CCCTCCCGGG AGAGCCATAG TGGTCTGCGG AACCGGTGAG TACACCGGAA       120

TTGCCAGGAC GACCGGGTCC TTTCTTGGAT CAACCCGCTC AATGCCTGGA GATTTGGGCG       180

TGCCCCCGCA AGACTGCTAG CCGAGTAGTG TTGGGTCGCG AAAGGCCTTG TGGTACTGCC       240

TGATAGGGTG CTTGCGAGTG CCCCGGGAGG TCTCGTAGAC CGTGCAATC                  289

(2) INFORMATION FOR SEQ ID NO:21:

(i) SEQUENCE CHARACTERISTICS:
        (A) LENGTH: 286 base pairs
        (B) TYPE: nucleic acid (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:21:

GATTCTGTCT TCACGCAGAA AGCGTCTAGC CATGGCGTTA GTATGAGTGT CGTGCAGCCT      60

CCAGGTCCCC CCCTCCCGGG AGAGCCATAG TGGTCTGCGG AACCGGTGAG TACACCGGAA     120

TTGCCAGGAC GACCGGGTCC TTTCTTGGAT CAACCCGCTC AATGCCTGGA GATTTGGGCG     180

TGCCCCCGCG AGACTGCTAG CCGAGTAGTG TTGGGTCGCG AAAGGCCTTG TGGTACTGCC     240

TGATAGGGTG CTTGCGAGTG CCCCGGGAGG TCTCGTAGAC CGTGCA                    286

(2) INFORMATION FOR SEQ ID NO:22:

(i) SEQUENCE CHARACTERISTICS:
            (A) LENGTH: 289 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:22:

GATTCTGTCT TCACGCAGAA AGCGTCTAGC CATGGCGTTA GTATGAGTGT CGTACAGCCT      60

CCAGGCCCCC CCCTCCCGGG AGAGCCATAG TGGTCTGCGG AACCGGTGAG TACACCGGAA     120

TTGCCGGGAA GACTGGGTCC TTTCTTGGAT AAACCCACTC TATGCCCGGC CATTTGGGCG     180

TGCCCCCGCA AGACTGCTAG CCGAGTAGCG TTGGGTTGCG AAAGGCCTTG TGGTACTGCC     240

TGATAGGGTG CTTGCGAGTA CCCCGGGAGG TCTCGTAGAC CGTGCAATC                 289

(2) INFORMATION FOR SEQ ID NO:23:

(i) SEQUENCE CHARACTERISTICS:
            (A) LENGTH: 289 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:23:

GATTCTGTCT TCACGCAGAA AGCGCCTAGC CATGGCGTTA GTACGAGTGT CGTGCAGCCT      60

CCAGGACCCC CCCTCCCGGG AGAACCATAG TGGTCTGCGG AACCGGTGAG TACACCGGAA     120

TCGCTGGGGT GACCGGGTCC TTTCTTGGAG CAACCCGCTC AATACCCAGA AATTTGGGCG     180

TGCCCCCGCG AGATCACTAG CCGAGTAGTG TTGGGTCGCG AAAGGCCTTG TGGTACTGCC     240

TGATAGGGTG CTTGCGAGTG CCCCGGGAGG TCTCGTAGAC CGTGCAATC                 289

(2) INFORMATION FOR SEQ ID NO:24:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:24:

CTCGCAAGCA CCCTATCA                                               18

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:25:

GCAGAAAGCG TCTAGCCATG G                                           21

(2) INFORMATION FOR SEQ ID NO:26:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:26:

GCAGAAAGCG TCTAGCCATG GCGTTAGTAT GAGTGTCGTG CAGCCTCCAG GACCCCCCCT    60

CCCGGGAGAG CCATAGTGGT CTGCGGAACC GGTGAGTACA CCGGAATTGC CAGGACGACC   120

GGGTCCTTTC TTGGATCAAC CCGCTCAATG CCTGGAGATT TGGGCGTGCC CCCGCAAGAC   180

TGCTAGCCGA GTAGTGTTGG GTCGCGAAAG GCCTTGTGGT ACTGCCTGAT AGGGTGCTTG   240

CGAG                                                              244

(2) INFORMATION FOR SEQ ID NO:27:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:27:

GCAGAAAGCG TCTAGCCATG GCGTTAGTAT GAGTGTCGTG CAGCCTCCAG GTCCCCCCCT    60

CCCGGGAGAG CCATAGTGGT CTGCGGAACC GGTGAGTACA CCGGAATTGC CAGGACGACC   120

GGGTCCTTTC TTGGATCAAC CCGCTCAATG CCTGGAGATT TGGGCGTGCC CCCGCGAGAC   180

TGCTAGCCGA GTAGTGTTGG GTCGCGAAAG GCCTTGTGGT ACTGCCTGAT AGGGTGCTTG   240

CGAG                                                              244

(2) INFORMATION FOR SEQ ID NO:28:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:28:

GCAGAAAGCG TCTAGCCATG GCGTTAGTAT GAGTGTCGTA CAGCCTCCAG GCCCCCCCCT    60

CCCGGGAGAG CCATAGTGGT CTGCGGAACC GGTGAGTACA CCGGAATTGC CGGGAAGACT    120

GGGTCCTTTC TTGGATAAAC CCACTCTATG CCCGGCCATT TGGGCGTGCC CCCGCAAGAC    180

TGCTAGCCGA GTAGCGTTGG GTTGCGAAAG GCCTTGTGGT ACTGCCTGAT AGGGTGCTTG    240

CGAG    244

(2) INFORMATION FOR SEQ ID NO:29:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:29:

GCAGAAAGCG CCTAGCCATG GCGTTAGTAC GAGTGTCGTG CAGCCTCCAG GACCCCCCCT    60

CCCGGGAGAA CCATAGTGGT CTGCGGAACC GGTGAGTACA CCGGAATCGC TGGGGTGACC    120

GGGTCCTTTC TTGGAGCAAC CCGCTCAATA CCCAGAAATT TGGGCGTGCC CCCGCGAGAT    180

CACTAGCCGA GTAGTGTTGG GTCGCGAAAG GCCTTGTGGT ACTGCCTGAT AGGGTGCTTG    240

CGAG    244

(2) INFORMATION FOR SEQ ID NO:30:

(i) SEQUENCE CHARACTERISTICS:
        (A) LENGTH: 216 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:30:

CAGAAAGGGT TTAGCCATGG GGTTAGTATG AGTGTCGTAC AGCCTCCAGG CCCCCCCCTC    60

CCGGGAGAGC CATAGTGGTC TGCGGAACCG GTGAGTACAC CGGAATTGCC GGGAAGACTG    120

GGTCCTTTCT TGGATAAACC CACTCTATGC CCGGCCATTT GGGCGTGCCC CGCAAGACT    180

GCTAGCCGAG TAGCGTTGGG TTGCGAAAGG CCTTGT    216

(2) INFORMATION FOR SEQ ID NO:31:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:31:

CAGAAAGGGT TTAGCCATGG CGTTAGTATG AGTGTCGTGC AGCCTCCAGG ACCCCCCCTC    60

CCGGGAGAGC CATAGTGGTC TGCGGAACCG GTGAGTACAC CGGAATTGCC AGGACGACCG    120

GGTCCTTTCT TGGATAAAAC CCGCTCAATG CCTGGAGATT TGGGCGTGCC CCCGCAAGAC    180

TGCTAGCCGA GTAGTGTTGG GTCGCGAAAG GCCTTGTGGT ACTGCCTGAT AGGGTGCTTG    240

CAAG                                                                    244

(2) INFORMATION FOR SEQ ID NO:32:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:32:

GCAGAAAGGT TTAGCCATGG GTTAGTATGA GTGTCGTGCA GCCTCCAGGA CCCCCCCTCC         60

CGGGAGAGCC ATAGTGGTCT GCGGAACCGG TGAGTACACC GGAATTGCCA GGACGACCGG        120

GTCCTTTCTT GGATTAACCC GCTCAATGCC TGGAGATTTG GGCGTGCCCC CGCAAGACTG        180

CTAGCCGAGT AGTGTTGGGT CGCGAAAGGC CTTGTGGTAC TGCCTGATAG GGTGCTTGC        239

(2) INFORMATION FOR SEQ ID NO:33:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:33:

GCAGAAAGGT TTAGCCATGG GGTTAGTATG AGTGTCGTAC AGCCTCCAGG ACCCCCCCTC        60

CCGGGAGAGC CATAGTGGTC TGCGGAACCG GTGAGTACAC CGGAATTGCC AGGACGACCG       120

GGTCCTTTCT TGGATAAACC CGCTCAATGC CTGGAGATTT GGGCGTGCCC CCGCAAGACT       180

GCTAGCCGAG TAGTGTTGGG TCGCGAAAGG CCTTGTGGTA CTGCCTGATA GGGTGCTTGC       240

(2) INFORMATION FOR SEQ ID NO:34:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:34:

GCAGAAAGGG TTTAGCCATG GCGTTAGTAT GAGTGTCGTA CAGCCTCCAG GCCCCCCCCT        60

CCCGGGAGAG CCATAGTGGT CTGCGGAACC GGTGAGTACA CCGGAATTAC CGGAAAGACT       120

GGGTCCTTTC TTGGATAAAC CCACTCTATG TCCGGTCATT TGGGCGTGCC CCCGCAAGAC       180

TGCTAGCCGA GTAGCGTTGG GTTGCAAAGG CCTTGTGGTA CTGCCTGATA GGGTGCTTGC       240

(2) INFORMATION FOR SEQ ID NO:35:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "DNA"

(xi) SEQUENCE DESCRIPTION: SEQ ID NO:35:

CAGAAAGGGT TTAGCCATGG GGTTAGTACG AGTGTCGTGC AGCCTCCAGG CCCCCCCCTC     60

CCGGGAGAGC CATAGTGGTC TGCGGAACCG GTGAGTACAC CGGAATCGCT GGGGTGACCG    120

GGTCCTTTCT TGGAGCAACC CGCTCAATAC CCAGAAATTT GGGCGTGCCC CCGCGAGATC    180

ACTAGCCGAG TAGTGTTGGG TCGCGAAAGG CCTTGTGGTA CTGCCTGATA GGGTGCTTGC    240

(2) INFORMATION FOR SEQ ID NO:36:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:36:

AGAAAGCGTT TAGCCATGGC GTTAGTATGA GTGTTGTGCA GCCTCCAGGA CCCCCCCTCC     60

CGGGAGAGCC ATAGTGGTCT GCGGAACCGG TGAGTACACC GGAATTGCCA GGACGACCGG    120

GTCCTTTCTT GGATCAACCC GCTCAATGCC TGGAGATTTG GGCGTGCCCC CGCAAGACTG    180

CTAGCCGAGT AGTGTTGGGT CGCGAAAGGC CTTGTGGTAC TGCCTGATAG GGTGCTTGC    239

(2) INFORMATION FOR SEQ ID NO:37:

(i) SEQUENCE CHARACTERISTICS:
        (A) LENGTH: 232 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:37:

GTTTAGCCAT GGCGTTAGTA TGAGTGTCGT GCAGCCTCCA GGACCCCCCC TCCCGGGAGA     60

GCCATAGTGG TCTGCGGAAC CGGTGAGTAC ACCGGAATTG CCAGGACGAC CGGGTCCTTT    120

CTTGGATCAA CCCGCTCAAT GCCTGGAGAT TTGGGCGTGC CCCCGCGAGA CCGCTAGCCG    180

AGTAGTGTTG GGTCGCGAAA GGCCTTGTGG TACTGCCTGA TAGGGTGCTT GC            232

(2) INFORMATION FOR SEQ ID NO:38:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:38:

GCAGAAAGCG TTTAGCCATG GCGTTAGTAC GAGTGTCGTG CAGCCTCCAG GACCCCCCCT     60

CCCGGGAGAG CCATAGTGGT CTGCGGAACC GGTGAGTACA CCGGAATCGC TGGGGTGACC    120

GGGTCCTTTC TTGGAACAAC CCGCTCAATA CCCAGAAATT TGGGCGTGCC CCCGCGAGAT    180

CACTAGCCGA GTAGTGTTGG GTCGCGAAAG GCCTTGTGGT ACTGCCTGAT AGGGTGCTTG    240

(2) INFORMATION FOR SEQ ID NO:39:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:39:

TGCTCTCTGG TCGCTGTCTG AAAGACAGCG TGGTCTCTCG TAAT    44

(2) INFORMATION FOR SEQ ID NO:40:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:40:

TGCTCTCTGG TCGCTGTCTG AAAGACTCCG TGGTCTCTCG TAAT    44

(2) INFORMATION FOR SEQ ID NO:41:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

TGCTCTCTGG TCGCTGTCTG AATTTTTTTT TGGTCTCTCG TAAT    44

(2) INFORMATION FOR SEQ ID NO:42:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

AGACCATTAC CAGA    14

(2) INFORMATION FOR SEQ ID NO:43:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

GAGACCATTA CCAGAG    16

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

AGAGACCATT ACCAGAGA                                            18

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

AGAGACCATT ACAAGCGA                                            18

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

AGCGAACATT ACCAGAGA                                            18

(2) INFORMATION FOR SEQ ID NO:47:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

AGAGACCAAC CAGAGA                                                16

(2) INFORMATION FOR SEQ ID NO:48:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:48:

AGAGACCAT                                                            9

(2) INFORMATION FOR SEQ ID NO:49:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:49:

TACCAGAGA      9

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:50:

ACCAGAGAGC      10

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:51:

TCAGACAGCG      10

(2) INFORMATION FOR SEQ ID NO:52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:52:

AGTGGTCTGC GGAACCGG      18

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:53:

```
AGTGTCGTTT GGAACCGG                                                     18

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:54:

AGTGTCGTAA GGAACCGG                                                     18

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:55:

AGTGTCGTCA GGAACCGG                                                     18

(2) INFORMATION FOR SEQ ID NO:56:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:56:

AGTGTCGTGG AACCGG                                                       16

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:57:

AGTGTCGTTT GGATCCGG                                                     18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:58:
```

```
AGTGACGTTT GGAACCGG                                                          18
```

(2) INFORMATION FOR SEQ ID NO:59:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:59:

```
GGAACCGG                                                                      8
```

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:60:

```
TTTTGTGAGT ACACCGGAAT                                                        20
```

(2) INFORMATION FOR SEQ ID NO:61:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:61:

```
TTTTGTGAGT ACAC                                                              14
```

(2) INFORMATION FOR SEQ ID NO:62:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:62:

```
TGAGTACACC GGAAT                                                             15
```

(2) INFORMATION FOR SEQ ID NO:63:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:63:

ATTCCGGTGT ACTCACCGGT TCCAAACGAC ACT                                    33

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:64:

CAGCCTCCCC TTCTTGGA                                                     18

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:65:

AGTGTCGTTT GGAATTAATT                                                   20

(2) INFORMATION FOR SEQ ID NO:66:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:66:

GCGAAAGGCC TTGTGG                                                       16

(2) INFORMATION FOR SEQ ID NO:67:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:67:

ACAGCCTCCA GGACCC                                                       16

(2) INFORMATION FOR SEQ ID NO:68:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

-continued (xi) SEQUENCE DESCRIPTION: SEQ ID NO:68:

GCAGCCTCCA GGACCC                                                           16

We claim:

1. A method, comprising:
   a) providing:
      i) target nucleic acid comprising first and second non-contiguous single-stranded regions separated by an intervening region comprising a double-stranded region;
      ii) a bridging oligonucleotide capable of binding to said first and second non-contiguous single-stranded regions;
      iii) a second oligonucleotide capable of binding to a portion of said first non-contiguous single-stranded region; and
      iii) a cleavage means;
   b) mixing said target nucleic acid, said bridging oligonucleotide, said second oligonucleotide, and said cleavage means under conditions such that a cleavage structure is formed and either said second oligonucleotide or said bridging oligonucleotide is cleaved.

2. The method of claim 1, wherein said cleavage means comprises a nuclease.

3. The method of claim 2, wherein said nuclease comprises a thermostable 5' nuclease.

4. The method of claim 3, wherein said thermostable 5' nuclease comprises an altered polymerase derived from a native polymerases of Thermus species.

5. The method of claim 1, wherein said conditions of said mixing allow for hybridization of said bridging oligonucleotide and said second oligonucleotide to said target nucleic acid so as to define a region of overlap of said oligonucleotides.

6. The method of claim 5, wherein said region of overlap comprises one base.

7. The method of claim 5, wherein said region of overlap comprises more than one base.

8. The method of claim 1, wherein said target nucleic acid is DNA.

9. The method of claim 8, wherein said DNA is viral DNA.

10. The method of claim 9, wherein said viral DNA is derived from a virus which virus is selected from the group consisting of Parvoviridae, Papovaviridae, Adenoviridae, Hepadnaviridae, Herpesviridae, Iridoviridae, and Poxviridae.

11. The method of claim 1, wherein said target nucleic acid is RNA.

12. The method of claim 11, wherein said RNA is viral RNA.

13. The method of claim 12, wherein said viral DNA is derived from a virus which virus is selected from the group consisting of Picornaviridae, Caliciviridae, Reoviridae, Togaviridae, Flaviviridae, Orthomyxoviridae, Paramyxoviridae, Arenaviridae, Rhabdoviridae, Coronaviridae, Bunyaviridae, and Retroviridae.

* * * * *